United States Patent [19]

Murata et al.

[11] Patent Number: 4,923,857
[45] Date of Patent: May 8, 1990

[54] 3-ALKENYL-1-AZABICYCLO(3.2.0)HEPT-2-ENE-2-CARBOXYLIC ACID COMPOUNDS

[75] Inventors: Masayoshi Murata; Toshiyuki Chiba, both of Osaka; Akira Yamada, Fujiidera, all of Japan

[73] Assignee: Fujisawa Pharmaceutical Company, Ltd., Osaka, Japan

[21] Appl. No.: 312,061

[22] Filed: Feb. 17, 1989

[30] Foreign Application Priority Data

Feb. 22, 1988 [GB] United Kingdom ............... 8804058

[51] Int. Cl.$^5$ ..................... C07D 487/01; A61R 31/40
[52] U.S. Cl. ..................................... 514/210; 540/302
[58] Field of Search ......................... 540/302; 214/210

[56] References Cited

U.S. PATENT DOCUMENTS

| | | | |
|---|---|---|---|
| 4,260,627 | 4/1981 | Christensen et al. | 514/210 |
| 4,267,188 | 5/1981 | Cama et al. | 514/210 |
| 4,348,320 | 9/1982 | Bouffard et al. | 514/210 |
| 4,465,632 | 8/1984 | Christensen et al. | 514/210 |
| 4,543,257 | 9/1985 | Cama et al. | 514/210 |
| 4,729,993 | 3/1988 | Christensen | 514/210 |

FOREIGN PATENT DOCUMENTS

| | | | |
|---|---|---|---|
| 0072710 | 5/1983 | European Pat. Off. | 514/210 |
| 0010316 | 12/1983 | European Pat. Off. | 514/210 |
| 0010317 | 12/1983 | European Pat. Off. | 514/210 |

Primary Examiner—Robert Gerstl
Attorney, Agent, or Firm—Oblon, Spivak, McClelland, Maier & Neustadt

[57] ABSTRACT

The invention relates to an antimicrobial compound of the formula:

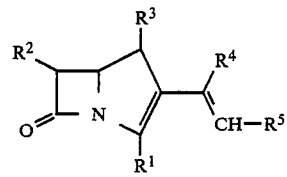

in which
$R^1$ is carboxy or protected carboxy,
$R^2$ is hydroxy(lower)alkyl or protected hydroxy(lower)alkyl,
$R^3$ and $R^4$ are each hydrogen or lower alkyl, and
$R^5$ is saturated 4 to 6-membered heteromonocyclic group containing 1 to 4 nitrogen atom(s), saturated 5 or 6-membered heteromonocyclic group containing 1 to 2 oxygen atom(s) and 1 to 3 nitrogen atom(s) or saturated 5 or 6-membered heteromonocyclic group containing 1 to 2 sulfur atom(s) and 1 to 3 nitrogen atom(s), wherein said aliphatic heterocyclic group may be substituted by one or more suitable substituent(s) selected from a group consisting of hydroxy, protected hydroxy, hydroxy(lower)alkyl, protected hydroxy(lower)alkyl, halogen, lower alkoxy, lower alkyl, lower alkoxy(lower)alkyl, imino, protected imino, lower alkylamino, protected lower alkylamino, mono(or di)-(lower)alkylcarbamoyloxy, lower alkylidene, lower alkanimidoyl and imino-protective group, or pharmaceutically acceptable salts thereof.

8 Claims, No Drawings

3-ALKENYL-1-AZABICYCLO(3.2.0)HEPT-2-ENE-2-CARBOXYLIC ACID COMPOUNDS

The present invention relates to novel 3-alkenyl-1-azabicyclo[3.2.0]hept-2-ene-2-carboxylic acid compounds and pharmaceutically acceptable salts thereof.

More particularly, it relates to novel 3-alkenyl-1-azabicyclo[3.2.0]hept-2-ene-2-carboxylic acid compounds and pharmaceutically acceptable salts thereof, which have antimicrobial activity, to processes for the preparation thereof, to a pharmaceutical composition comprising the same, and to a use of the same as a medicament and in the treatment of infectious diseases caused by pathogenic microorganisms in human being or animal.

Accordingly, one object of the present invention is to provide novel 3-alkenyl-1-azabicyclo[3.2.0]hept-2-ene-2-carboxylic acid compounds and pharmaceutically acceptable salts thereof, which are highly active against a number of pathogenic microorganisms and are useful as antimicrobial agents.

Another object of the present invention is to provide processes for the preparation of novel 3-alkenyl-1-azabicyclo[3.2.0]hept-2-ene-2-carboxylic acid compounds and salts thereof.

A further object of the present invention is to provide a pharmaceutical composition comprising, as an active ingredient, said 3-alkenyl-1-azabicyclo[3.2.0]hept-2-ene-2-carboxylic acid compounds and pharmaceutically acceptable salts thereof.

Still further object of the present invention is to provide a use of said 3-alkenyl-1-azabicyclo[3.2.0]hept-2-ene-2-carboxylic acid compounds and pharmaceutically acceptable salts thereof as a medicament and in the treatment of infectious diseases caused by pathogenic microorganisms in human being or animal.

The object 3-alkenyl-1-azabicyclo[3.2.0]hept-2-ene-2-carboxylic acid compounds are novel and can be represented by the following general formula:

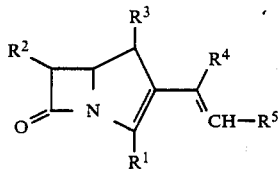

in which
$R^1$ is carboxy or protected carboxy,
$R^2$ is hydroxy(lower)alkyl or protected hydroxy(lower)alkyl,
$R^3$ and $R^4$ are each hydrogen or lower alkyl, and
$R^5$ is aliphatic heterocyclic group, which may be substituted by suitable substituent(s),
and pharmaceutically acceptable salts thereof.

In the object compound (I) and the intermediary compounds mentioned below, it is to be understood that there may be one or more stereo-isomeric pair(s) such as optical and/or geometrical isomers due to asymmetric carbon atom(s) and/or double bond(s), and such isomers are also included within the scope of the present invention.

Suitable salts of the object compound (I) are conventional non-toxic, pharmaceutically acceptable salts and may include a salt with a base such as an inorganic base salt, for example, an alkali metal salt (e.g. sodium salt, potassium salt, etc.), an alkaline earth metal salt (e.g. calcium salt, magnesium salt, etc.), an ammonium salt, an organic base salt, for example, an organic amine salt (e.g. triethylamine salt, pyridine salt, picoline salt, ethanolamine salt, triethanolamine salt, dicyclohexylamine salt, N,N'-dibenzylethylenediamine salt, etc.); a salt with an acid such as an inorganic acid addition salt (e.g. hydrochloride, hydrobromide, sulfate, phosphate, etc.), an organic acid addition salt (e.g. formate, acetate, trifluoroacetate, maleate, tartrate, methanesulfonate, benzenesulfonate, etc.); a salt with a basic or acidic amino acid (e.g. arginine, aspartic acid, glutamic acid, etc.); intramolecular quarternary salt and the like.

According to the present invention, the object compound (I) and pharmaceutically acceptable salts thereof can be prepared by the processes as illustrated by the following reaction schemes.

Process 1:

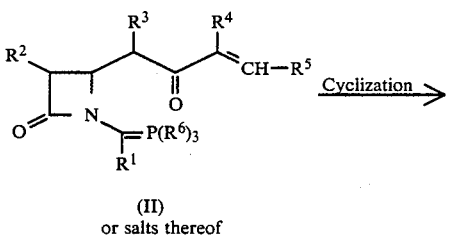

(II)
or salts thereof

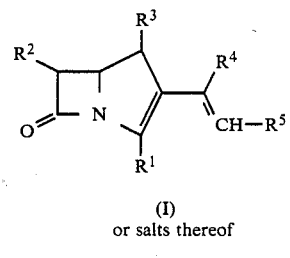

(I)
or salts thereof

Process 2:

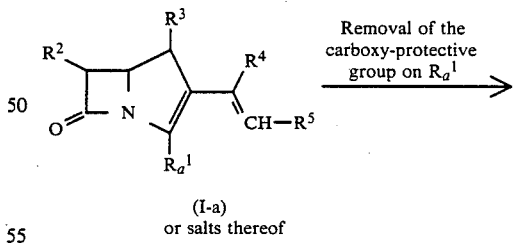

(I-a)
or salts thereof

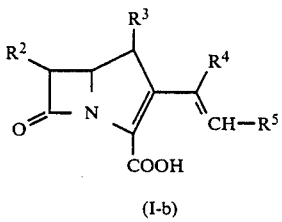

(I-b)
or salts thereof

Process 3:

-continued

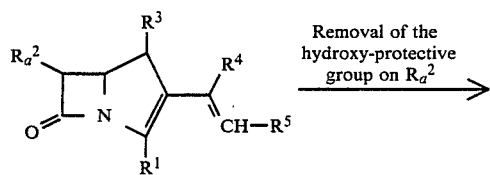

(I-c)
or salts thereof

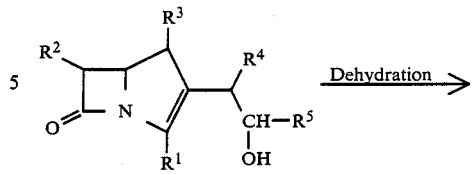

(III)
or a reactive derivative
at the hydroxy group
thereof, or salts thereof

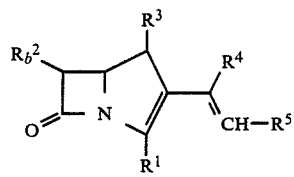

(I-d)
or salts thereof

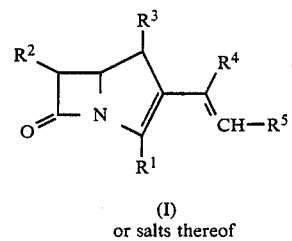

(I)
or salts thereof

Process 4:

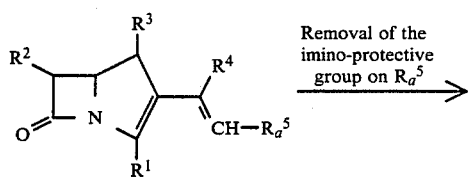

(I-e)
or salts thereof

Process 7:

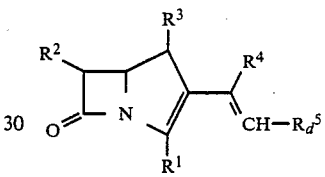

(I-h)
or salts thereof

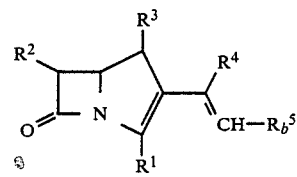

(I-f)
or salts thereof

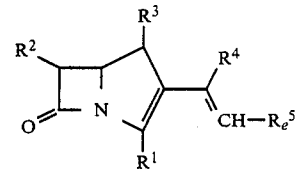

(I-i)
or salts thereof

Process 5:

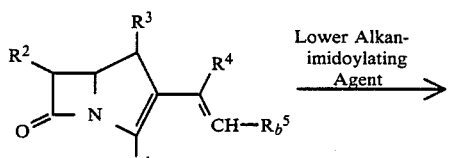

(I-f)
or salts thereof

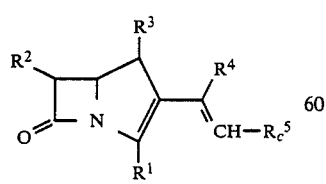

(I-g)
or salts thereof

Process 6:

in which
$R^1$, $R^2$, $R^3$, $R^4$ and $R^5$ are each as defined above,
$R_a^1$ is protected carboxy,
$R_a^2$ is protected hydroxy(lower)alkyl,
$R_b^2$ is hydroxy(lower)alkyl,
$R_a^5$ is aliphatic heterocyclic group containing protected imino-moiety(ies), which may be substituted by suitable substituent(s),
$R_b^5$ is aliphatic heterocyclic group containing imino-moiety(ies), which may be substituted by suitable substituent(s),
$R_c^5$ is aliphatic heterocyclic group containing lower alkanimidoylimino-moiety(ies), which may be substituted by suitable substituent(s),
$R_d^5$ is aliphatic heterocyclic group, which is substituted by protected hydroxy, protected hydroxy(lower)alkyl, protected lower alkylamino or protected imino,
$R_e^5$ is aliphatic heterocyclic group, which is substituted by hydroxy, hydroxy(lower)alkyl, lower alkylamino or imino, and
$R^6$ is aryl or lower alkoxy.

The starting compounds (II) and (III) used in the processes 1 and 6 are new and can be prepared, for example, by the methods as shown in the following.

Method A:

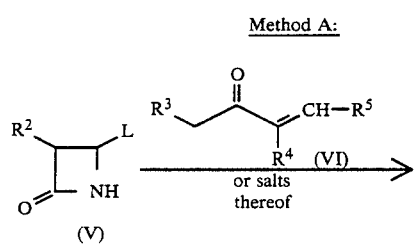

(V)

(VI) or salts thereof (VII) or salts thereof

Method B:

(VII) or salts thereof

CHO—R¹ (VIII) or its reactive equivalents (IX) or salts thereof

Method C:

(IX) or a reactive derivative at the hydroxy group thereof, or salts thereof

P(R⁶)₃ (X)

(II) or salts thereof

Method D:

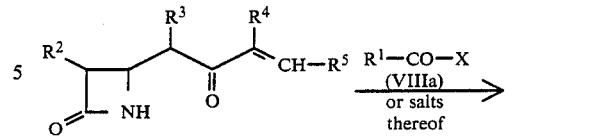

(VII) or a salt thereof

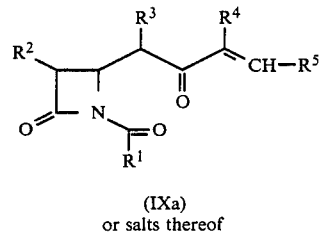

(IXa) or salts thereof

Method E:

(IXa) or salts thereof

P(R⁶)₃ (X)

(II) or salts thereof

Method F:

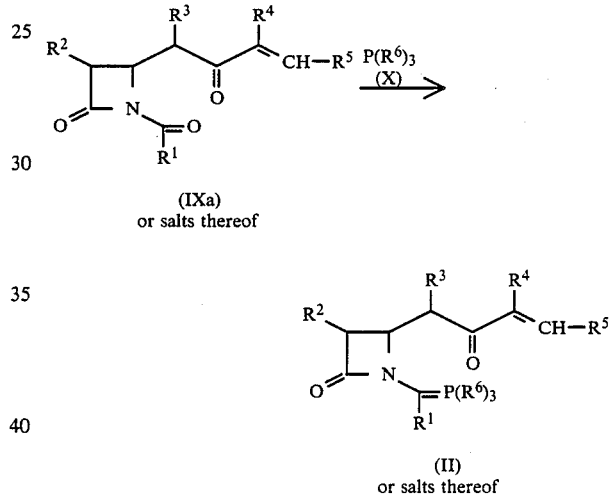

(XI) or salts thereof

CHO—R⁵ (XII) or salts thereof (II) or salts thereof

Method G:

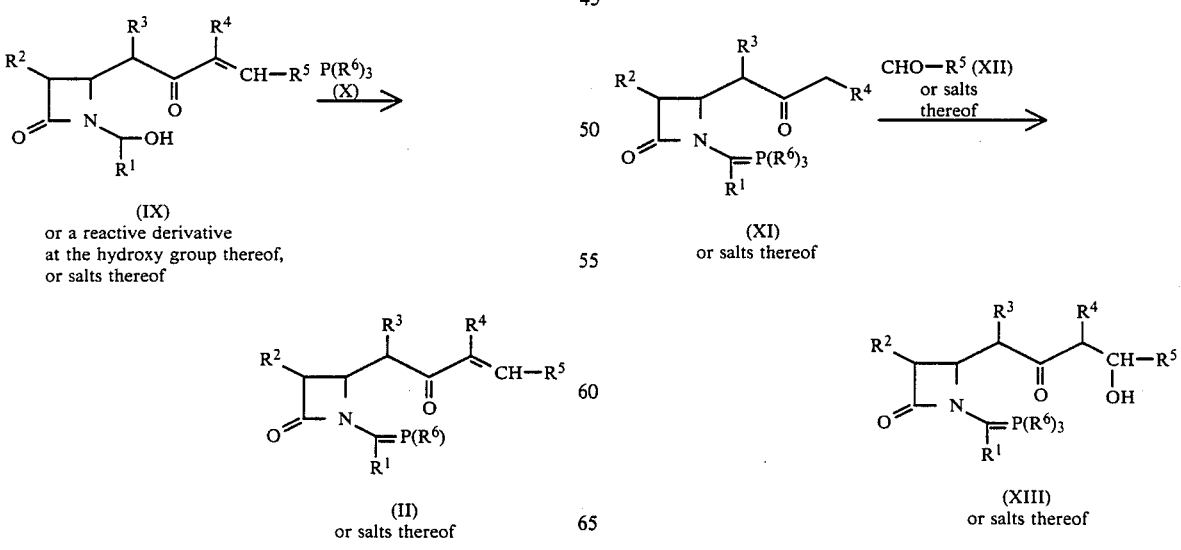

(XIII) or salts thereof

-continued

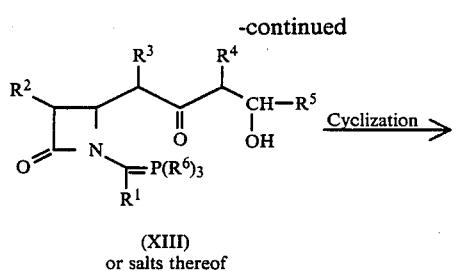

(XIII)
or salts thereof

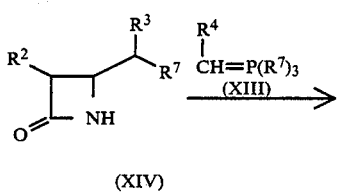

(III)
or salts thereof

Method H:

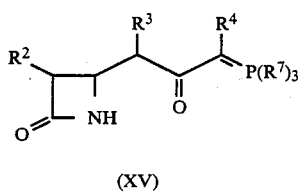

(XIV)

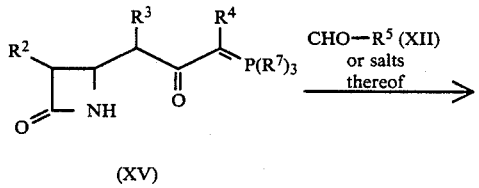

(XV)

Method I:

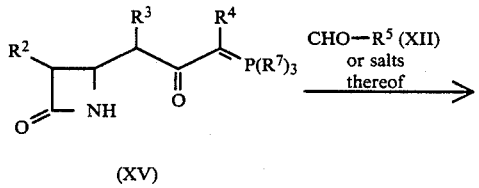

(XV)

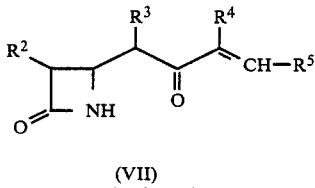

(VII)
or salts thereof in which
$R^1$, $R^2$, $R^3$, $R^4$, $R^5$ and $R^6$ are each as defined above,
$R^7$ is protected carboxy,
L is a leaving group, and
X is an acid residue.

In the above and subsequent descriptions of the present specification, suitable examples and illustrations of the various definitions which the present invention includes within the scope thereof are explained in detail as follows.

The term "lower" is intended to mean 1 to 6 carbon atom(s), unless otherwise indicated.

Suitable "protected carboxy" may include esterified carboxy, wherein "esterified carboxy" can be referred to the ones as mentioned below.

Suitable examples of the ester moiety of an esterified carboxy may be the ones such as lower alkyl ester (e.g. methyl ester, ethyl ester, propyl ester, isopropyl ester, butyl ester, isobutyl ester t-butyl ester, pentyl ester, hexyl ester, etc.), which may have at least one suitable substituent(s), for example, lower alkanoyloxy(lower)alkyl ester (e.g. acetoxymethyl ester, propionyloxymethyl ester, butyryloxymethyl ester, valeryloxymethyl ester, pivaloyloxymethyl ester, hexanoyloxymethyl ester, 1-(or 2-)acetoxyethyl ester, 1-(or 2- or 3-)acetoxypropyl ester, 1-(or 2- or 3- or 4-)acetoxybutyl ester, 1-(or 2-)propionyloxyethyl ester, 1-(or 2- or 3-)propionyloxpropyl ester, 1-(or 2-)-butyryloxyethyl ester, 1-(or 2-)isobutyryloxyethyl ester, 1-(or 2-)pivaloyloxyethyl ester, 1-(or 2-)hexanoyloxyethyl ester, isobutyryloxymethyl ester, 2-ethylbutyryloxymethyl ester, 3-3-dimethylbutyryloxymethyl ester, 1-(or 2-)-pentanoyloxyethyl ester, etc.), lower alkanesulfonyl(lower)alkyl ester (e.g. 2-mesylethyl ester, etc.), mono(or di or tri)halo(lower)alkyl ester (e.g. 2-iodoethyl ester, 2,2,2-trichloroethyl ester, etc.); lower alkoxycarbonyloxy(lower)alkyl ester (e.g. methoxycarbonyloxymethyl ester, ethoxycarbonyloxymethyl ester, propoxycarbonyloxymethyl ester, t-butoxycarbonyloxymethyl ester, 1-(or 2-)methoxycarbonyloxyethyl ester, 1-(or 2-)ethoxycarbonyloxyethyl ester, 1-(or 2-)isopropoxycarbonyloxyethyl ester, etc.), phthalidylidene(-lower)alkyl ester, or (5-lower alkyl-2-oxo-1,3-dioxol-4-yl)(lower)alkyl ester (e.g. (5-methyl-2-oxo-1,3-dioxol-4-yl)methyl ester, (5-ethyl-2-oxo-1,3-dioxol-4-yl)methyl ester, (5-propyl-2-oxo-1,3-dioxol-4-yl)ethyl ester, etc.); lower alkenyl ester (e.g. vinyl ester, allyl ester, etc.); lower alkynyl ester (e.g. ethynyl ester, propynyl ester, etc.); ar(lower)alkyl ester which may have at least one suitable substituent(s) (e.g. benzyl ester, 4-methoxybenzyl ester, 4-nitrobenzyl ester, phenethyl ester, trityl ester, benzhydryl ester, bis(methoxyphenyl)methyl ester, 3,4-dimethoxybenzyl ester, 4-hydroxy-3,5-di-t-butylbenzyl ester, etc.); aryl ester which may have at least one suitable substituent(s) (e.g. phenyl ester, 4-chlorophenyl ester, tolyl ester, t-butylphenyl ester, xylyl ester, mesityl ester, cumenyl ester, etc.); phthalidyl ester; and the like.

More preferable example of the protected carboxy thus defined may be $C_2$-$C_4$ alkenyloxycarbonyl and phenyl (or nitrophenyl)($C_1$-$C_4$)alkoxycarbonyl for $R^1$ or $R_a^1$, and $C_1$-$C_4$ alkoxycarbonyl for $R^7$, and the most preferable one may be allyloxycarbonyl for $R^1$ or $R_a^1$, and methoxycarbonyl for $R^7$.

Suitable "hydroxy(lower)alkyl" may include straight or branched lower alkyl substituted by hydroxy group such as hydroxymethyl, hydroxyethyl, hydroxypropyl, 1-(hydroxymethyl)ethyl, 1-hydroxy-1-methylethyl, hydroxybutyl, hydroxypentyl, hydroxyhexyl, and the like, in which more preferable example may be hydroxy($C_1$-$C_4$)alkyl and the most preferable one may be 1-hydroxyethyl.

Suitable "protected hydroxy(lower)alkyl" may include aforementioned hydroxy(lower)alkyl, in which the hydroxy group is protected by a conventional hydroxy-protective group such as those mentioned in the explanation of imino-protective group as mentioned below preferably, lower alkenyloxycarbonyl and phenyl(or nitrophenyl)-(lower)alkoxycarbonyl; and further C$_6$-C$_{10}$ ar(lower)alkyl such as mono- or di- or triphenyl(lower)alkyl (e.g. benzyl, benzhydryl, trityl, etc.), etc.; trisubstituted silyl such as tri(lower)alkylsilyl (e.g. trimethylsilyl, triethylsilyl, isopropyldimethylsilyl, t-butyldimethylsilyl, diisopropylmethylsilyl, etc.), tri(C$_6$-C$_{10}$)arylsilyl (e.g. triphenylsilyl, etc.), tris[(-C$_6$-C$_{10}$)ar(lower)alkyl]silyl, for example, tris[phenyl(-lower)alkyl]silyl (e.g. tribenzylsilyl, etc.), etc.; and the like.

More preferable example of "protected hydroxy(lower)alkyl" thus defined may be {phenyl(or nitrophenyl)(-C$_1$-C$_4$)alkoxy}carbonyloxy(C$_1$-C$_4$)alkyl, C$_2$-C$_4$ {tri(C$_1$-C$_4$)alkylsilyl}oxy(C$_1$-C$_4$)alkyl, and the most preferable one may be 1-trimethylsilyloxyethyl and 1-t-butyldimethylsilyloxyethyl.

Suitable "lower alkyl" may include straight or branched one such as methyl, ethyl, propyl, isopropyl, butyl, t-butyl, pentyl, hexyl, and the like, in which more preferable example may be C$_1$-C$_4$ alkyl and the most preferable one may be methyl.

Suitable "aliphatic heterocyclic group" moiety in the term of "aliphatic heterocyclic group, which may be substituted by suitable substituent(s)" means saturated, monocyclic or polycyclic heterocyclic group containing at least one hetero-atom such as an oxygen, sulfur, nitrogen atom and the like.

Preferable aliphatic heterocyclic group, which may be substituted by suitable substituent(s) may be:

saturated 3 to 8-membered, more preferably 4 to 6-membered heteromonocyclic group containing 1 to 4 nitrogen atom(s), for example, azetidinyl, pyrrolidinyl, imidazolidinyl, piperidinyl, pyrazolidinyl, piperazinyl, etc.;

saturated 3 to 8-membered, more preferably 5 or 6-membered heteromonocyclic group containing 1 to 2 oxygen atom(s) and 1 to 3 nitrogen atom(s), for example, morpholinyl, etc.;

saturated 3 to 8-membered, more preferably 5 or 6-membered heteromonocyclic group containing 1 to 2 sulfur atom(s) and 1 to 3 nitrogen atom(s), for example, thiazolidinyl, etc.; and the like, wherein said aliphatic heterocyclic group may be substituted by one or more, preferably one or two suitable substituent(s) such as:

hydroxy;

protected hydroxy, in which the hydroxy group is protected by a conventional hydroxy-protective group as mentioned in the explanation of protected hydroxy(lower)alkyl, more preferably tri(C$_1$-C$_4$)alkylsilyloxy (e.g. t-butyldimethylsilyloxy, etc.);

hydroxy(lower)alkyl or protected hydroxy(lower)alkyl as mentioned above, more preferably hydroxy(C$_1$-C$_4$)alkyl (e.g. hydroxymethyl, etc.) or tri(C$_1$-C$_4$)alkylsilyloxy-(C$_1$-C$_4$)alkyl (e.g. t-butyldimethylsilyloxymethyl, etc.);

halogen (e.g. chlorine, bromine, iodine or fluorine, preferably fluorine);

lower alkoxy as mentioned below, more preferably C$_1$-C$_4$ alkoxy (e.g. methoxy, etc.);

lower alkyl as mentioned above, more preferably C$_1$-C$_4$ alkyl (e.g. methyl, etc.);

lower alkoxy(lower)alkyl, in which the lower alkoxy and lower alkyl moieties may be respectively the same as those for lower alkoxy and lower alkyl as mentioned above, more preferably C$_1$-C$_4$ alkoxy(C$_1$-C$_4$)alkyl (e.g. methoxymethyl, etc.);

imino;

protected imino, in which the imino group is protected by a conventional imino-protective group as mentioned below, more preferably C$_2$-C$_4$ alkenyloxycarbonylimino (e.g. allyloxycarbonylimino, etc.);

lower alkylamino, in which the lower alkyl moiety may be the same as those for lower alkyl as mentioned above, more preferably C$_1$-C$_4$ alkylamino (e.g. methylamino, etc.);

protected lower alkylamino, which is the lower alkylamino group as mentioned above, in which the amino group is protected by a conventional amino-protective group such as those for the imino-protective group mentioned below, more preferably N-(C$_2$-C$_4$alkenyloxycarbonyl)-N-(C$_1$-C$_4$)alkylamino (e.g. N-allyloxycarbonyl-N-methylamino, etc.);

mono(or di)(lower)alkylcarbamoyloxy, in which the lower alkyl moiety may be the same as those for lower alkyl as mentioned above, more preferably mono(or di)-(C$_1$-C$_4$)alkylcarbamoyloxy (e.g. methylcarbamoyloxy, dimethylcarbamoyloxy, etc.);

lower alkylidene, more preferably C$_1$-C$_4$ alkylidine (e.g. methylene, etc.); and the like.

And further when said aliphatic heterocyclic group has imino-moiety(ies) in its ring, the imino-moiety(ies) may be substituted by suitable substituent(s) such as:

lower alkyl as mentioned above, lower alkanimidoyl, which may be straight or branched one such as formimidoyl, acetimidoyl, propionimidoyl, butyrimidoyl, isovalerimidoyl, pentanimidoyl, hexanimidoyl, etc., more preferably C$_1$-C$_4$ alkanimidoyl (e.g. formimidoyl, acetimidoyl, etc.);

imino-protective group as mentioned below, preferably, lower alkenyloxycarbonyl, more preferably C$_2$-C$_4$ alkenyloxycarbonyl (e.g. allyloxycarbonyl, etc.); and the like.

Preferable example of "aliphatic heterocyclic group, which may be substituted by suitable substituent(s)" may be:

pyrrolidinyl (e.g. pyrrolidin-2-yl, pyrrolidin-3-yl, etc.);

N-protected pyrrolidinyl such as 1-(lower)alkenyloxycarbonylpyrrolidinyl, preferably 1-(C$_2$-C$_4$)alkenyloxycarbonylpyrrolidinyl (e.g. 1-allyloxycarbonylpyrrolidin-2-yl, 1-allyloxycarbonylpyrrolidin-3-yl, etc.);

1-(lower)alkanimidoylpyrrolidinyl, preferably 1-(C$_1$-C$_4$)alkanimidoylpyrrolidinyl (e.g. 1-formimidoylpyrrolidin-2-yl, 1-acetimidoylpyrrolidin-2-yl, etc.);

hydroxypyrrolidinyl (e.g. 4-hydroxypyrrolidin-2-yl, etc.);

N-protected hydroxypyrrolidinyl such as 1-(lower alkenyloxycarbonyl)(hydroxy)pyrrolidinyl, preferably 1-(C$_2$-C$_4$ alkenyloxycarbonyl)(hydroxy)pyrrolidinyl (e.g. 1-allyloxycarbonyl-4-hydroxypyrrolidin-2-yl, etc.);

N-protected (protected hydroxy)pyrrolidinyl such as 1-(lower alkenyloxycarbonyl)[tri(lower)alkylsilyloxy]pyrrolidinyl, preferably 1-(C$_2$-C$_4$ alkenyloxycarbonyl)[tri(C$_1$-C$_4$)alkylsilyloxy]pyrrolidinyl (e.g. 1-allyloxycarbonyl-4-t-butyldimethylsilyloxypyrrolidin-2-yl, etc.);

lower alkoxypyrrolidinyl, preferably C$_1$-C$_4$ alkoxypyrrolidinyl (e.g. 4-methoxypyrrolidin-2-yl, etc.);

N-protected (lower alkoxy)pyrrolidinyl such as 1-(lower alkenyloxycarbonyl)(lower alkoxy)pyrrolidinyl, preferably 1-(C$_2$-C$_4$ alkenyloxycarbonyl)(C$_1$-C$_4$ alkoxy)pyrrolidinyl (e.g. 1-allyloxycarbonyl-4-methoxypyrrolidin-2-yl, etc.);

[di(lower)alkylcarbamoyloxy]pyrrolidinyl, preferably [di($C_1$–$C_4$)alkylcarbamoyloxy]pyrrolidinyl [e.g. 4-(dimethylcarbamoyloxy)pyrrolidin-2-yl, etc.];

N-protected [di(lower)alkylcarbamoyloxy]pyrrolidinyl such as 1-(lower alkenyloxycarbonyl)[di(lower)alkylcarbamoyloxy]pyrrolidinyl, preferably 1-($C_2$–$C_4$ alkenyloxycarbonyl)[di($C_1$–$C_4$)alkylcarbamoyloxy]pyrrolidinyl [e.g. 1-allyloxycarbonyl-4-(dimethylcarbamoyloxy)pyrrolidin-2-yl, etc.);

(lower alkylcarbamoyloxy)pyrrolidinyl, preferably ($C_1$–$C_4$ alkylcarbamoyloxy)pyrrolidinyl [e.g. 4-(methylcarbamoyloxy)pyrrolidin-2-yl, etc.];

N-protected (lower alkylcarbamoyloxy)pyrrolidinyl such as 1-(lower alkenyloxycarbonyl)(lower alkylcarbamoyloxy)pyrrolidinyl, preferably 1-($C_2$–$C_4$ alkenyloxycarbonyl)($C_1$–$C_4$ alkylcarbamoyloxy)pyrrolidinyl [e.g. 1-allyloxycarbonyl-4-(methylcarbamoyloxy)-pyrrolidin-2-yl, etc.];

(lower alkylamino)pyrrolidinyl, preferably ($C_1$–$C_4$ alkylamino)pyrrolidinyl [e.g. 4-(methylamino)pyrrolidin-2-yl, etc.];

N-protected (protected lower alkylamino)pyrrolidinyl such as 1-(lower alkenyloxycarbonyl)[(N-(lower)alkenyloxycarbonyl)-N-(lower)alkylamino]pyrrolidinyl, preferably 1-($C_2$–$C_4$ alkenyloxycarbonyl)[N-(C )alkenyloxycarbonyl-N-($C_1$–$C_4$)alkylamino]pyrrolidinyl [e.g. 1-allyloxycarbonyl-4-(N-allyloxycarbonyl-N-methylamino)-pyrrolidin-2-yl, etc.];

halopyrrolidinyl (e.g. 4-fluoropyrrolidin-2-yl, etc.);

N-protected halopyrrolidinyl such as 1-(lower alkenyloxycarbonyl)halopyrrolidinyl, preferably 1-($C_2$–$C_4$ alkenyloxycarbonyl)fluoropyrrolidinyl (e.g. 1-allyloxycarbonyl-4-fluoropyrrolidin-2-yl, etc.);

[lower alkoxy(lower)alkyl]pyrrolidinyl, preferably [$C_1$–$C_4$ alkoxy($C_1$–$C_4$)alkyl]pyrrolidinyl [e.g. 4-(methoxymethyl)pyrrolidin-2-yl, etc.);

N-protected [lower alkoxy(lower)alkyl]pyrrolidinyl such as 1-(lower alkenyloxycarbonyl)[lower alkoxy(lower)alkyl]pyrrolidinyl, preferably 1-($C_2$–$C_4$ alkenyloxycarbonyl)[$C_1$–$C_4$ alkoxy(C )alkyl]pyrrolidinyl [e.g. 1-allyloxycarbonyl-4-(methoxymethyl)pyrrolidin-2-yl, etc.);

[hydroxy(lower)alkyl]pyrrolidinyl, preferably [hydroxy($C_1$–$C_4$)alkyl]pyrrolidinyl [e.g. 5-(hydroxymethyl)-pyrrolidin-2-yl, etc.];

N-protected [hydroxy(lower)alkyl]pyrrolidinyl such as 1-(lower alkenyloxycarbonyl)[hydroxy(lower)alkyl]pyrrolidinyl, preferably 1-($C_2$–$C_4$ alkenyloxycarbonyl)-[hydroxy($C_1$–$C_4$)alkyl]pyrrolidinyl [e.g. 1-allyloxycarbonyl-5-(hydroxymethyl)pyrrolidin-2-yl, etc.];

[lower alkylamino(lower)alkanoyl]pyrrolidinyl, preferably 1-[$C_1$–$C_4$ alkylamino($C_1$–$C_4$)alkanoyl]pyrrolidinyl [e.g. 1-(methylaminoacetyl)pyrrolidin-2-yl, etc.];

[protected (lower)alkylamino(lower)alkanoyl]pyrrolidinyl such as 1-[N-(lower)alkenyloxycarbonyl-N-(lower)alkylamino(lower)alkanoyl]pyrrolidinyl, preferably 1-{N-( )alkenyloxycarbonyl-N-($C_1$–$C_4$)alkylamino($C_1$–$C_4$)-alkanoyl]pyrrolidinyl [e.g. 1-(N-allyloxycarbonyl-N-methylaminoacetyl)pyrrolidin-2-yl, etc.];

(lower alkyl)(imino)pyrrolidinyl, preferably 1-[($C_1$–$C_4$)alkyl]iminopyrrolidinyl (e.g. 1-methyl-5-iminopyrrolidin-2-yl, etc.);

(lower alkyl)(protected imino)pyrrolidinyl such as 1-(lower alkyl)(lower alkenyloxycarbonylimino)pyrrolidinyl, preferably 1-($C_1$–$C_4$ alkyl)($C_2$–$C_4$ alkenyloxycarbonylimino)-pyrrolidinyl [e.g. 1-methyl-5-(allyloxycarbonylimino)pyrrolidin-2-yl, etc.];

piperidinyl (e.g. piperidin-2-yl, etc.);

N-protected piperidinyl such as 1-(lower alkenyloxycarbonyl)piperidinyl, preferably 1-($C_2$–$C_4$)alkenyloxycarbonylpiperidinyl (e.g. 1-allyloxycarbonylpiperidin-2-yl, etc.);

azetidinyl (e.g. azetidin-3-yl, etc.);

N-protected azetidinyl such as 1-(lower)alkenyloxycarbonyl)azetidinyl, preferably 1-($C_2$–$C_4$)alkenyloxycarbonylazetidinyl (e.g. 1-allyloxycarbonylazetidin-3-yl, etc.);

morpholinyl (e.g. morpholin-3-yl, etc.);

N-protected morpholinyl such as 4-(lower)alkenyloxycarbonylmorpholinyl, preferably 4-($C_2$–$C_4$)alkenyloxycarbonylmorpholinyl (e.g. 4-allyloxycarbonylmorpholin-3-yl, etc.);

lower alkylidenepyrrolidinyl, preferably $C_1$–$C_4$ alkylidenepyrrolidinyl (e.g. 4-methylenepyrrolidin-2-yl, etc.);

protected (lower alkylidene)pyrrolidinyl such as 1-(lower alkenyloxycarbonyl)(lower alkylidene)pyrrolidinyl, preferably 1-($C_2$–$C_4$ alkenyloxycarbonyl($C_1$–$C_4$ alkylidene)pyrrolidinyl (e.g. 1-allyloxycarbonyl-4-methylenepyrrolidin-2-yl, etc.).

"Aliphatic heterocyclic group containing imino-moiety(ies), which may be substituted by suitable substituent(s)" means the "aliphatic heterocyclic group, which may be substituted by suitable substituent(s)" mentioned above, in which the aliphatic heterocyclic ring contains at least one imino-moiety.

"Aliphatic heterocyclic group containing protected imino-moiety(ies), which may be substituted by suitable substituent(s)" means the "aliphatic heterocyclic group, which may be substituted by suitable substituent(s)" mentioned above, in which the aliphatic heterocyclic ring contains at least one protected imino-moiety.

"Aliphatic heterocyclic group containing lower alkanimidoylimino-moiety(ies), which may be substituted by suitable substituent(s)" means the "aliphatic heterocyclic group, which may be substituted by suitable substituent(s)" mentioned above, in which the aliphatic heterocyclic ring contains at least one lower alkanimidoylimino-moiety.

"Aliphatic heterocyclic group, which is substituted by protected hydroxy, protected hydroxy(lower)alkyl, protected lower alkylamino or protected imino" means the "aliphatic heterocyclic group, which may be substituted by suitable substituent(s)" mentioned above, in which the aliphatic heterocyclic ring possesses protected hydroxy, protected hydroxy(lower)alkyl, protected lower alkylamino or protected imino as the substituent.

"Aliphatic heterocyclic group, which is substituted by hydroxy, hydroxy(lower)alkyl, lower alkylamino or imino" means the "aliphatic heterocyclic group, which may be substituted by suitable substituent(s)" mentioned above, in which the aliphatic heterocyclic ring possesses hydroxy, hydroxy(lower)alkyl, lower alkylamino or imino as the substituent.

Suitable "lower alkoxy" may include straight or branched one such as methoxy, ethoxy, propoxy, isopropoxy, butoxy, isobutoxy, pentyloxy, isopentyloxy hexyloxy, etc., in which more preferable example may be $C_1$–$C_4$ alkoxy and the most preferable one may be methoxy.

Suitable "acid residue" may include an inorganic acid residue such as azide, halogen (e.g. chlorine, bromine, fluorine or iodine), and the like, an organic acid residue such as acyloxy (e.g. benzenesulfonyloxy, tosyloxy, methanesulfonyloxy, acetoxy, etc.), and the like, in which more preferable example may be halogen and the most preferable one may be iodine.

Suitable "aryl" may include $C_6$–$C_{10}$ aryl such as phenyl, tolyl, xylyl, cumenyl, mesithyl, naphthyl and the like, in which more preferable example may be phenyl.

Suitable "leaving group" may include acid residue as mentioned above, in which more preferable example may be lower alkanoyloxy and the most preferable one may be acetoxy.

Suitable example of imino-protective group may include acyl such as carbamoyl, aliphatic acyl, aromatic acyl, heterocyclic acyl and aliphatic acyl substituted by aromatic or heterocyclic group(s) derived from carboxylic, carbonic, sulfonic and carbamic acids.

The aliphatic acyl may include saturated or unsaturated, acyclic or cyclic ones, for example, alkanoyl such as lower alkanoyl (e.g. formyl, acetyl, propionyl, butyryl, isobutyryl, valeryl, isovaleryl, pivaloyl, hexanoyl, etc.), alkylsulfonyl such as lower alkylsulfonyl (e.g. mesyl, ethylsulfonyl, propylsulfonyl, isopropylsulfonyl, butylsulfonyl isobutylsulfonyl, pentylsulfonyl, hexylsulfonyl, etc.), carbamoyl, N-alkylcarbamoyl (e.g. methylcarbamoyl, ethylcarbamoyl, etc.), alkoxycarbonyl such as lower alkoxycarbonyl (e.g. methoxycarbonyl, ethoxycarbonyl, propoxycarbonyl, butoxycarbonyl, t-butoxycarbonyl, etc.), alkenyloxycarbonyl such as lower alkenyloxycarbonyl (e.g. vinyloxycarbonyl, allyloxycarbonyl, etc.), alkenoyl such as lower alkenoyl (e.g. acryloyl, methacryloyl, crotonoyl, etc.), cycloalkanecarbonyl such as cyclo(lower)alkanecarbonyl (e.g. cyclopropanecarbonyl, cyclopentanecarbonyl, cyclohexanecarbonyl, etc.), and the like.

The aromatic acyl may include aroyl (e.g. benzoyl, toluoyl, xyloyl, etc.), N-arylcarbamoyl (e.g. N-phenylcarbamoyl, N-tolylcarbamoyl, N-naphthylcarbamoyl, etc.), arenesulfonyl (e.g. benzenesulfonyl, tosyl, etc.), and the like.

The heterocyclic acyl may include heterocycliccarbonyl (e.g. furoyl, thenoyl, nicotinoyl, isonicotinoyl, thiazolylcarbonyl, thiadiazolylcarbonyl, tetrazolylcarbonyl, etc.), and the like.

The aliphatic acyl substituted by aromatic group(s) may include aralkanoyl such as phenyl(lower)alkanoyl (e.g. phenylacetyl, phenylpropionyl, phenylhexanoyl, etc.), aralkoxycarbonyl such as phenyl(lower)alkoxycarbonyl (e.g. benzyloxycarbonyl, phenethyloxycarbonyl, etc.), aryloxyalkanoyl such as phenoxy(lower)alkanoyl (e.g. phenoxyacetyl, phenoxypropionyl, etc.), and the like.

The aliphatic acyl substituted by heterocyclic group(s) may include heterocyclic-alkanoyl such as heterocyclic(lower)alkanoyl (e.g. thienylacetyl, imidazolylacetyl furylacetyl, tetrazolylacetyl, thiazolylacetyl, thiadiazolylacetyl, thienylpropionyl, thiadiazolylpropionyl, etc.), and the like.

These acyl groups may be further substituted by one or more suitable substituents such as lower alkyl (e.g. methyl ethyl, propyl, isopropyl, butyl, pentyl, hexyl, etc.), halogen (e.g. chlorine, bromine, iodine, fluorine), lower alkoxy (e.g. methoxy, ethoxy, propoxy, isopropoxy, butoxy, pentyloxy, hexyloxy, etc.), lower alkylthio (e.g. methylthio, ethylthio, propylthio, isopropylthio, butylthio, pentylthio, hexylthio, etc.), nitro, lower alkylamino (e.g. methylamino, ethylamino, propylamino, isopropylamino, etc.), protected lower alkylamino (e.g. N-allyloxycarbonyl-N-methylamino, etc.), and the like, and preferable acyl having such substituent(s) may be mono(or di or tri)haloalkanoyl (e.g. chloroacetyl, bromoacetyl, dichloroacetyl, trifluoroacetyl, etc.), mono(or di or tri)haloalkoxycarbonyl (e.g. chloromethoxycarbonyl, dichloromethoxycarbonyl, 2,2,2-trichloroethoxycarbonyl, etc.), nitro-(or halo-or lower alkoxy)aralkoxycarbonyl (e.g. nitrobenzyloxycarbonyl, chlorobenzyloxycarbonyl, methoxybenzyloxycarbonyl, etc.), mono(or di or tri)halo(lower)alkylsulfonyl (e.g. fluoromethylsulfonyl difluoromethylsulfonyl, trifluoromethylsulfonyl, trichloromethylsulfonyl, etc.), and the like.

More preferable examples of imino-protective group thus defined may be ($C_2$–$C_4$)alkenyloxycarbonyl, phenyl(or nitrophenyl)($C_1$–$C_4$)alkoxycarbonyl, $C_1$–$C_4$ alkylamino($C_1$–$C_4$)alkanoyl and N-($C_2$–$C_4$)alkenyloxycarbonyl-N-($C_1$–$C_4$)alkylamino-($C_1$–$C_4$)alkanoyl, and the most preferable one may be allyloxycarbonyl, (methylamino)acetyl and N-allyloxycarbonyl-N-methylaminoacetyl.

The processes for the preparation of the object compound (I) of the present invention are explained in detail in the following.

(1) Process 1:

The compound (I) or salts thereof can be prepared by cyclizing the compound (II) or salts thereof.

Suitable salts of the compound (II) may be the same as those for the compound (I).

This reaction is preferably carried out by heating the compound (II) in a conventional solvent which does not adversely influence the reaction such as dioxane, hexamethylphosphoramide, benzene, toluene, xylene, dimethyl sulfoxide, N,N-dimethylformamide, pyridine, etc., or a mixture thereof.

This reaction can also be carried out in the presence of hydroquinone.

The reaction temperature of this reaction is not critical and the reaction is usually carried out under from warming to heating.

(2) Process 2:

The compound (I-b) or salts thereof can be prepared by subjecting the compound (I-a) or salts thereof to removal reaction of the carboxy-protective group on $R_a^1$.

Suitable salts of the compounds (I-a) and (I-b) may be the same as those for the compound (I).

The present reaction is usually carried out by a conventional method such as hydrolysis, reduction, and the like.

(i) Hydrolysis:

Hydrolysis is preferably carried out in the presence of a base or an acid. Suitable base may include an alkalimetal hydroxide (e.g. sodium hydroxide, potassium hydroxide, etc.), an alkaline earth metal hydroxide (e.g. magnesium hydroxide, calcium hydroxide, etc.;, alkali metal hydride (e.g. sodium hydride, potassium hydride, etc.), alkaline earth metal hydride (e.g. calcium hydride, etc.), alkali metal alkoxide (e.g. sodium methoxide, sodium ethoxide, potassium t-butoxide, etc.), an alkali metal carbonate (e.g. sodium carbonate, potassium carbonate, etc.), and alkaline earth metal carbonate (e.g. magnesium carbonate, calcium carbonate, etc.), an alkali metal bicarbonate (e.g. sodium bicarbonate, potassium bicarbonate, etc.), and the like.

Suitable acid may include an organic acid (e.g. formic acid, acetic acid, propionic acid, trifluoroacetic acid, benzenesulfonic acid, p-toluenesulfonic acid, etc.) and an inorganic acid (e.g. hydrochloric acid, hydrobromic acid, sulfuric acid, phosphoric acid, etc.). The acidic hydrolysis using trifluoroacetic acid is usually accelerated by addition of cation trapping agent (e.g. phenol, anisole, etc.).

In case that the hydroxy-protective group is tri(-lower)alkylsilyl, the hydrolysis can be carried out in the presence of tri(lower)alkylammonium halide (e.g. tributylammonium fluoride, etc.).

This reaction is usually carried out in a conventional solvent which does not adversely influence the reaction such as water, dichloromethane, alcohol (e.g. methanol, ethanol, etc.), tetrahydrofuran, dioxane, acetone, etc., or a mixture thereof. A liquid base or acid can be also used as the solvent.

The reaction temperature is not critical and the reaction is usually carried out under from cooling to heating.

(ii) Reduction:

The reduction method applicable for this removal reaction may include, for example, reduction by using a combination of a metal (e.g. zinc, zing amalgam, etc.) or a salt of chrome compound (e.g. chromous chloride, chromous acetate, etc.) and an organic or inorganic acid (e.g. acetic acid, propionic acid, hydrochloric acid, sulfuric acid, etc.); and conventional catalytic reduction in the presence of a conventional metallic catalyst such as palladium catalysts (e.g. spongy palladium, palladium black, palladium oxide, palladium on carbon, colloidal palladium, palladium on barium sulfate, palladium on barium carbonate, palladium hydroxide on carbon, etc.), nickel catalysts (e.g. reduced nickel, nickel oxide, Raney nickel, etc.), platinum catalysts (e.g. platinum plate, spongy platinum, platinum black, colloidal platinum, platinum oxide, platinum wire, etc.), and the like.

In case that the catalytic reduction is applied, the reaction is preferably carried out around neutral condition.

This reaction is usually carried out in a conventional solvent which does not adversely influence the reaction such as water, alcohol (e.g. methanol, ethanol, propanol, etc.), dioxane, tetrahydrofuran, acetic acid, buffer solution (e.g. phosphate buffer, acetate buffer, etc.), and the like, or a mixture thereof.

The reaction temperature is not critical and the reaction is usually carried out under from cooling to warming.

In case that the carboxy-protective group is allyl group, it can be deprotected by hydrogenolysis using a palladium compound.

Suitable palladium compound used in this reaction may be palladium on carbon, palladium hydroxide on carbon, palladium chloride, a palladium-ligand complex such as tetrakis(triphenylphosphine)palladium(0), bis(-dibenzylideneacetone)palladium(0), di[1,2-bis(diphenyl phosphino)ethane]palladium(0), tetrakis(triphenyl phosphite)palladium(0), tetrakis(triethyl phosphite)palladium(0), and the like.

The reaction can preferably be carried out in the presence of a scavenger of allyl group generated in situ, such as amine (e.g. morpholine, N-methylaniline, etc.), an activated methylene compound (e.g. dimedone, benzoyl acetate, 2-methyl-3-oxovaleric acid, etc.), a cyanohydrin compound (e.g. α-tetrahydropyranyloxybenzyl cyanide, etc.), lower alkanoic acid or a salt thereof (e.g. formic acid, acetic acid, ammonium formate, sodium acetate, etc.), N-hydroxysuccinimide, and the like.

This reaction can be carried out in the presence of a base such as lower alkylamine (e.g. butylamine, triethylamine, etc.), pyridine, and the like.

When palladium-ligand complex is used in this reaction, the reaction can preferably be carried out in the presence of the corresponding ligand (e.g. triphenylphosphine, triphenyl phosphite, triethyl phosphite, etc.).

This reaction is usually carried out in a conventional solvent which does not adversely influence the reaction such as water, methanol, ethanol, propanol, dioxane, tetrahydrofuran, acetonitrile, chloroform, dichloromethane, dichloroethane, ethyl acetate, etc., or a mixture thereof.

The removal reaction can be selected according to the kind of carboxy-protective group to be removed.

The present process includes within the scope thereof a case that the hydroxy-protective group on $R^2$, and/or imino- and/or hydroxy-protective group(s) on $R^5$ are removed at the same time during the reaction.

(3) Process 3:

The compound (I-d) or salts thereof can be prepared by subjecting the compound (I-c) or salts thereof to removal reaction of the hydroxy-protective group on $R_a^2$.

Suitable salts of the compounds (I-c) and (I-d) may be the same as those for the compound (I).

This reaction is usually carried out by a conventional method such as hydrolysis, reduction and the like.

The method of hydrolysis and reduction, and the reaction conditions (e.g. reaction temperature, solvent, etc.) are substantially the same as those illustrated for removal reaction of the carboxy-protective group of the compound (I-a) in Process 2, and therefore are to be referred to said explanation.

In case that the hydroxy-protective group is tri(-lower)alkylsilyl, the removal of this protective group can also be carried out in the presence of tetra(lower)alkylammonium fluoride (e.g. tetrabutylammonium fluoride, etc.).

The present process includes within the scope thereof a case that the carboxy-protective group on $R^1$ and/or imino- and/or hydroxy-protective group(s) on $R^5$ are removed at the same time during the reaction.

(4) Process 4:

The compound (I-f) or salts thereof can be prepared by subjecting the compound (I-e) or salts thereof to removal reaction of the imino-protective group on $R_a^5$.

Suitable salts of the compound (I-e) may be salts with bases such as those given for the compound (I).

Suitable salts of the compound (I-f) may be the same as those for the compound (I).

This reaction is usually carried out by a conventional method such as hydrolysis, reduction, and the the like.

The method of hydrolysis and reduction, and the reaction conditions (e.g. reaction temperature, solvent, etc.) are substantially the same as those illustrated for removal reaction of the carboxy-protective group of the compound (I-a) in Process 2, and therefore are to be referred to said explanation.

The present process includes within the scope thereof a case that the carboxy- and/or hydroxy-protective group(s) on $R^1$ and/or $R^2$, and/or hydroxy-protective group on $R^5$ are removed at the same time during the reaction.

(5) Process 5:

The compound (I-g) or salts thereof can be prepared by reacting the compound (I-f) or salts thereof with lower alkanimidoylating agent.

Suitable salts of the compound (I-g) may be the same as those for the compound (I).

Suitable lower alkanimidoylating agent may be conventional ones which can introduce the lower alkanimidoyl group as mentioned above into the compound (I-f), and said preferable agent may be lower alkyl (lower)alkanimidate (e.g. methyl formimidate, ethyl formimidate, methyl acetimidate, ethyl acetimidate, ethyl propionimidate, ethyl butyrimidate, ethyl isovalerimidate, ethyl pentanimidate, ethyl hexanimidate, etc.), (lower)alkanimidoyl halide (e.g. formimidoyl chloride, formimidoyl bromide, acetimidoyl chloride, acetimidoyl bromide, propionimidoyl chloride, butyrimidoyl chloride, isovalerimidoyl, chloride, pentanimidoyl chloride, hexanimidoyl chlordide, etc.), and the like, or an acid addition salt thereof.

This reaction is usually carried out in a conventional solvent which does not adversely influence the reaction such as tetrahydrofuran, dioxane, water, methanol, ethanol, buffer solution (e.g. phosphate buffer, etc.), etc., or a mixture thereof.

This reaction can be carried out in the presence of an organic or inorganic base such as those given in the explanation of Process 2.

The reaction temperature is not critical, and the reaction is usually carried out under from cooling to warming.

(6) Process 6:

The compound (I) or salts thereof can be prepared by dihydrating the compound (III) or a reactive derivative at the hydroxy group thereof, or salts thereof.

Suitable salts of the compound (III) may be the same as those for the compound (I).

Suitable reactive derivative at the hydroxy group of the compound (III) may include a conventional one such as halide (e.g. chloride, bromide, iodide, etc.), sulfonate (e.g. methanesulfonate, benzenesulfonate, toluenesulfonate, etc.), and the like, in which more preferable example may be sulfonate.

This dehydration can be carried out, for example, by reacting the compound (III) or a reactive derivative at the hydroxy group thereof, or salts thereof with a base.

Suitable base used in this reaction may be an organic base such as trialkylamine (e.g. trimethylamine, triethylamine, etc.), pyridine, picoline, lutidine, N-methylpyrrolidine, N-methylmorpholine, 1,5-diazabicyclo[4.3.0]non-5-one, 1-4-diazabicyclo[2.2.2]octane, 1,5-diazabicyclo[5.4.0]undecene-5, or the like.

This reaction is usually carried out in a conventional solvent which does not adversely influence the reaction such as water, dichloromethane, alcohol (e.g. methanol, ethanol, etc.), tetrahydrofuran, dioxane, acetone, etc., or a mixture thereof. A liquid base or can be also used as the solvent.

The reaction temperature is not critical and the reaction is usually carried out under from cooling to heating.

(7) Process 7:

The compound (I-i) or salts thereof can be prepared by subjecting the compound (I-h) or salts thereof to removal reaction of the hydroxy-, amino- or imino-protective group on $R_d^5$.

Suitable salts of the compounds (I-h) and (I-i) may be the same as those for the compound (I).

This reaction is usually carried out by a conventional method such as hydrolysis, reduction, and the like.

The method of hydrolysis and reduction, and the reaction conditions (e.g. reaction temperature, solvent, etc.) are substantially the same as those illustrated for removal reaction of the carboxy-protective group of the compound (I-a) in Process 2, and therefore are to be referred to said explanation.

The present process includes within the scope thereof a case that the imino-protective group, if any, in the aliphatic heterocyclic group is removed at the same time during the reaction.

Methods for preparing the new starting compound (III) or salts thereof are explained in detail in the following.

(A) Method A:

The compound (VII) or salts thereof can be prepared by reacting the compound (V) with the compound (VI) or salts thereof.

Suitable salts of the compound (VI) and (VII) may be the same acid addition salts as those for the compound (I).

The compound (VI) or salts thereof can be prepared from the known compounds by a conventional manner or that described in the Preparations of the present specification.

This reaction can be carried out in the presence of a base such as alkali metal hydroxide (e.g. sodium hydroxide, potassium hydroxide, etc.), alkaline earth metal hydroxide (e.g. magnesium hydroxide, calcium hydroxide, etc.), alkali metal hydride (e.g. sodium hydride, potassium hydride, etc.), alkaline earth metal hydride (e.g. calcium hydride etc.), alkali metal alkoxide (e.g. sodium methoxide, sodium ethoxide, potassium t-butoxide, etc.), alkali metal carbonate (e.g. sodium carbonate, potassium carbonate, etc.), alkaline earth metal carbonate (e.g. magnesium carbonate, calcium carbonate, etc.), alkali metal bicarbonate (e.g. sodium bicarbonate, potassium bicarbonate, etc.), and the like.

This reaction can preferably be carried out in the presence of an enolizating agent. Suitable enolizating agent may include tri(lower)alkylsilyl trihalo(lower)alkanesulfonate, preferably tri($C_1$–$C_4$)alkylsilyl trihalo-($C_1$–$C_4$)alkanesulfonate (e.g. trimethylsilyl trifluoromethanesulfonate, etc.), tin compound such as stannous (lower)alkylsulfonate which may have halogen(s), preferably stannous polyhalo($C_1$–$C_4$)alkylsulfonate (e.g. stannous trifluoromethanesulfonate, etc.), and the like.

This reaction is usually carried out in a conventional solvent which does not adversely influence the reaction such as water, dichloromethane, alcohol (e.g. methanol, ethanol, etc.), tetrahydrofuran, dioxane, acetone, etc., or a mixture thereof. A liquid base can be also used as the solvent.

The reaction temperature is not critical and the reaction is usually carried out under from cooling to warming.

(B) Method B:

The compound (IX) or salts thereof can be prepared by reacting the compound (VII) or salts thereof with the compound (VIII) or its reactive equivalents.

Suitable salts of the compound (IX) may be the same as those for the compound (I).

Suitable example of the compound (VIII) may be glyoxylic acid, in which the carboxy group may be protected by a conventional carboxy-protective group to form esterified carboxy as mentioned above.

Suitable reactive equivalents of the compound (VIII) may include monohydrate thereof.

This reaction can preferably be carried out with azeotropic removal of water produced in situ. The azeotropic removal of the water can be carried out by a conventional method (e.g. azeotropic distillation, etc.).

This reaction is usually carried out in a conventional solvent which does not adversely influence the reaction such as water, dichloromethane, alcohol (e.g. methanol, ethanol, etc.), tetrahydrofuran, dioxane, acetone, benzene, toluene, xylene, etc., or a mixture thereof.

The reaction temperature is not critical and the reaction is usually carried out under from warming to heating.

(C) Method C:

The compound (II) or salts thereof can be prepared by reacting the compound (IX) or a reactive derivative at the hydroxy group thereof, or salts thereof with the compound (X).

Suitable reactive derivative at the hydroxy group of the compound (IX) may include a conventional one such as halide (e.g. chloride, bromide, iodide, etc.), sulfonate (e.g. methanesulfonate, benzenesulfonate, toluenesulfonate, etc.) and the like, in which more preferable example may be halide.

Preferable example of the compound (X) may be triphenylphosphine, tri($C_1$–$C_4$)alkyl phosphite (e.g. triethyl phosphite, etc.), and the like.

This reaction can be carried out in the presence of an inorganic or organic base such as an alkali metal bicarbonate (e.g. sodium bicarbonate, potassium bicarbonate, etc.), alkali metal carbonate (e.g. sodium carbonate, potassium carbonate, etc.), alkaline earth metal carbonate (e.g. magnesium carbonate, calcium carbonate, etc.), tri(lower)alkylamine (e.g. trimethylamine, triethylamine, N,N-diisopropyl-N-ethylamine, etc.), pyridine compounds [e.g. pyridine, picoline, lutidine, N,N-di(lower)alkylaminopyridine such as N,N-dimethylaminopyridine, etc.], quinoline, imidazole, N-lower alkylmorphorine (e.g. N-methylmorphorine, etc.), N-lower alkylpiperidine (e.g. N-ethylpiperidine, etc.), N,N-di(lower)alkylbenzylamine (e.g. N,N-dimethylbenzylamine, etc.), and the like.

This reaction is usually carried out in a conventional solvent which does not adversely influence the reaction such as dioxane, acetonitrile, chloroform, dichloromethane, hexamethylphosphoramide, dichloroethane, tetrahydrofuran, ethyl acetate dimethyl sulfoxide, N,N-dimethylformamide, pyridine, etc., or a mixture thereof.

The reaction temperature of this reaction is not critical and the reaction is usually carried out under from cooling to warming.

(D) Method D:

The compound (IXa) or salts thereof can be prepared by reacting the compound (VII) or salts thereof with the compound (VIIIa) or salts thereof.

Suitable salts of the compound (IXa) may be the same as those for the compound (I).

Suitable salts of the compound (VIIIa) may be the same as those for the compound (I-e).

Suitable example of the compound (VIIIa) may be oxalyl halide, in which the carboxy group may be protected by a conventional carboxy-protective group as mentioned above.

This reaction can be carried out in the presence of a base as mentioned in Method C.

This reaction is usually carried out in a conventional solvent which does not adversely influence the reaction such as dioxane, acetonitrile, chloroform, dichloromethane, hexamethylphosphoramide, dichloroethane, tetrahydrofuran, ethyl acetate, dimethyl sulfoxide, N,N-dimethylformamide, pyridine, etc., or a mixture thereof.

The reaction temperature of this reaction is not critical and the reaction is usually carried out under from cooling to warming.

(E) Method E:

The compound (II) or salts thereof can be prepared by reacting the compound (IXa) or salts thereof with the compound (X).

This reaction is usually carried out in a conventional solvent which does not adversely influence the reaction such as dioxane, acetonitrile, chloroform, dichloromethane, hexamethylphosphoramide, dichloroethane, tetrahydrofuran, ethyl acetate, dimethyl sulfoxide, N,N-dimethylformamide, pyridine, benzene, toluene, xylene, etc., or a mixture thereof.

The reaction temperature of this reaction is not critical and the reaction is usually carried out under from warming to hating.

(F) Method F:

The compound (XIII) or salts thereof can be prepared by reacting the compound (XI) or salts thereof with the compound (XII) or salts thereof.

Suitable salts of the compounds (XI) and (XIII) may be the same as those for the compound (I).

Suitable salts of the compound (XII) may be salts with acids such as those given for the compound (I).

This reaction is preferably carried out in the presence of a base such as alkali metal di(lower)alkylamide, preferably lithium di($C_1$–$C_4$)alkylamide (e.g. lithium diisopropylamide, etc.), alkali metal hydroxide (e.g. sodium hydroxide, potassium hydroxide, etc.), alkaline earth metal hydroxide (e.g. magnesium hydroxide, calcium hydroxide, etc.) alkali metal hydride (e.g. sodium hydride, potassium hydride, etc.), alkaline earth metal hydride (e.g. calcium hydride, etc.), alkali metal alkoxide (e.g. sodium methoxide, sodium ethoxide, potassium t-butoxide, etc.), alkali metal carbonate (e.g. sodium carbonate, potassium carbonate, etc.), alkaline earth metal carbonate (e.g. magnesium carbonate, calcium carbonate, etc.), alkali metal bicarbonate (e.g. sodium bicarbonate, potassium bicarbonate, etc.), and the like.

This reaction is usually carried out in a conventional solvent which does not adversely influence the reaction such as water, dichloromethane, alcohol (e.g. methanol, ethanol, etc.), hexane, tetrahydrofuran, dioxane, acetone, benzene, toluene, xylene, etc., or a mixture thereof.

The reaction temperature is not critical and the reaction is usually carried out under from cooling to warming.

The compound (XI) can be prepared according to a conventional method as shown, for example in U.S. Pat. No. 4,348,320.

(G) Method G:

The compound (III) or salts thereof can be prepared by cyclizing the compound (XIII) or salts thereof.

This reaction is preferably carried out by heating the compound (XIII) in a conventional solvent which does not adversely influence the reaction such as dioxane, hexamethylphosphoramide, benzene, toluene, xylene, dimethyl sulfoxide, N,N-dimethylformamide, pyridine, etc., or a mixture thereof.

The reaction temperature of this reaction is not critical and the reaction is usually carried out under warming to heating.

(H) Method H:

The compound (XV) can be prepared by reacting the compound (XIV) with the compound (XIII).

This reaction is usually carried out in a conventional solvent which does not adversely influence the reaction such as dioxane, acetonitrile, chloroform, dichloromethane, hexane, hexamethylphosphoramide, dichloroethane, tetrahydrofuran, ethyl acetate, dimethyl sulfoxide, N,N-dimethylformamide, pyridine, benzene, toluene, xylene, etc., or a mixture thereof.

The reaction temperature of this reaction is not critical and the reaction is usually carried out under from cooling to warming.

(I) Method I:

The compound (VII) or salts thereof can be prepared by reacting the compound (XV) with the compound (XII) or salts thereof.

This reaction is preferably carried out by heating the compound (XV) and (XII) in a conventional solvent which does not adversely influence the reaction such as dioxane, hexamethylphosphoramide, benzene, toluene, xylene, dimethyl sulfoxide, N,N-dimethylformamide, pyridine, etc., or a mixture thereof.

This reaction can also be carried out in the presence of hydroquinone.

The reaction temperature of this reaction is not critical and the reaction is usually carried out under from warming to heating.

The object compounds obtained according to the processes 1 to 7, can be isolated and purified in a conventional manner, for example, extraction, precipitation, fractional crystallization, recrystallization, chromatography, and the like.

The object compound (I) and pharmaceutically acceptable salts thereof of the present invention are novel and exhibit high antimicrobial activity, inhibiting the growth of a wide variety of pathogenic microorganisms including Gram-positive and Gram-negative microorganisms, and further, are very stable against dehydropeptidase and show high urinary excretion, therefore have high potential for the treatment of various infectious diseases.

In the present invention, the object compound (I) having lower alkyl as $R^4$ possesses more potent antimicrobial activity and higher stability against dehydropeptidase.

Now in order to show the utility of the object compound (I), the test data on antimicrobial activity of the representative compound of the compound (I) of this invention is shown in the following.

in vitro Antimicrobial Activity

Test Method:

in vitro Antimicrobial Activity was determined by the two-fold agar-plate dilution method as described below.

One loopful of an overnight culture of a test strain in Trypticase-soy broth ($10^6$ viable cells per ml) was streaked on heart infusion agar (HI-agar) containing graded concentrations of the test compound, and the minimal inhibitory concentration (MIC) was expressed in terms of $\mu$ml after incubation at 37° C. for 20 hours.

Test Compound:

(5R,6S)-6-[(1R)-1-Hydroxyethyl]-7-oxo-3-[(E)-2-{(2S)-pyrrolidin-2-yl}-1-methylethenyl]-1-azabicyclo[3.2.0]hept-2-ene-2-carboxyic acid Test Result:

| Test Strain | MIC ($\mu$g/ml) |
|---|---|
| S. aureus 209P JC-1 | ≦ 0.025 |

For therapeutic administration, the object compound (I) and the pharmaceutically acceptable salts thereof of the present invention are used in the form of conventional pharmaceutical preparation which contains said compound, as an active ingredient, in admixture with pharmaceutically acceptable carriers such as an organic or inorganic solid or liquid excipient which is suitable for oral, parenteral and external administration. The pharmaceutical preparations may be in solid form such as tablet, granule, powder, capsule, or liquid form such as solution, suspension, syrup, emulsion, lemonade, and the like.

If needed, there may be included in the above preparations auxiliary substances, stabilizing agents, wetting agents and other commonly used additives such as lactose, stearic acid, magnesium stearate, terra alba, sucrose, corn starch, talc, gelatin, agar, pectin, peanut oil, olive oil, cacao butter, ethylene glycol, tartaric acid, citric acid, fumaric acid, and the like.

While the dosage of the compound (I) may vary from and also depend upon the age, conditions of the patient, a kind of diseases, a kind of the compound (I) to be applied, etc. In general, amount between 1 mg and about 4,000 mg or even more per day may be administered to a patient. An average single dose of about 1 mg, 10 mg, 50 mg, 100 mg, 250 mg, 500 mg, 1000 mg, 2000 mg of the object compound (I) of the present invention may be used in treating diseases infected by pathogenic microorganisms.

The following Preparations and Examples are given for the purpose of illustrating this invention in more detail.

Preparation 1-(1)

To a solution of oxalyl chloride (5.45 ml) in dichloromethane (100 ml) was added dropwise a solution of dimethyl sulfoxide (9.67 ml) in dichloromethane (10 ml) at −78° C. After stirring at −78° C. for 10 minutes, to the mixture was added dropwise a solution of (2S)-1-allyloxycarbonyl-2-hydroxymethylpyrrolidine (10.41 g) in dichloromethane (20 ml). After stirring at −78° C. for 10 minutes, to the mixture was added dropwise triethylamine (39.6 ml) and the resulting mixture was allowed to warm to 0° C. and diluted with ethyl acetate (400 ml) and brine (200 ml). After adjusting pH to around 5 with 4N hydrochloric acid, the organic layer was separated, washed with brine and dried over magnesium sulfate. Evaporation of the solvent gave an oil of 1-allyloxycarbonyl-2-formylpyrrolidine (8.72 g), which was dissolved in toluene (100 ml). To this solution was added 3-triphenylphosphoranylidenebutan-2-one (17.4 g) and the mixture was allowed to stand at ambient temperature for 5 days. Evaporation of the solvent gave a residue which was taken up into ethyl acetate. The resulting precipitate was removed by filtration and the filtrate was evaporated in vacuo. The residue was chromatographed on silica gel (300 ml) eluting with a mixture of n-hexane and ethyl acetate (9:1–6:4 V/V) to give (2S)-1-allyloxycarbonyl-2-(2-methyl-3-oxo-1-butenyl)-pyrrolidine (9.00 g).

IR (CH$_2$Cl$_2$): 1690, 1670 cm$^{-1}$

NMR (CDCl$_3$, δ): 1.83 (3H, d, J=1Hz), 1.50–2.43 (4H, m), 2.27 (3H, s), 3.34–3.75 (2H, m), 4.40–4.80 (3H, m), 5.00–5.43 (2H, m), 5.59–6.20 (1H, m), 6.45 (1H, dq, J=1, 8Hz)

Preparation 1-(2)

(2S,4R)-1-Allyloxycarbonyl-4-t-butyldimethylsilyloxy-2-(2-methyl-3-oxo-1-butenyl)pyrrolidine (8.66 g) was obtained in substantially the same manner as that of Preparation 1-(1).

IR (CH$_2$Cl$_2$): 1690, 1665 cm$^{-1}$
NMR (CDCl$_3$, δ): 0.10 (6H, s), 0.90 (9H, s), 1.83 (3H, d, J=1Hz), 2.30 (3H, s), 1.44–2.40 (2H, m), 3.55 (2H, d, J=3Hz), 4.20–5.00 (4H, m), 5.00–5.43 (2H, m), 5.60–6.13 (1H, m), 6.47 (1H, dq, J=1, 8Hz)

Preparation 2-(1)

To a solution of (2S)-1-allyloxycarbonyl-2-(2-methyl-3-oxo-1-butenyl)pyrrolidine (9.00 g) and triethylamine (6.3 ml) in dichloromethane (200 ml) was added trimethylsilyl trifluoromethanesulfonate (11.7 ml) at −20° C. After stirring at 0° C. for 1 hour, a solution of (3R,4R)-4-acetoxy-3-[(1R)-1-t-butyldimethylsilyloxyethyl]-2-azetidinone (10.9 g) and zinc bromide (11.9 g) in ethyl acetate (70 ml) was added to the mixture and the resultant mixture was stirred at 0° C. for 45 minutes. The reaction mixture was taken up into a mixture of ethyl acetate (600 ml) and water (600 ml). After adjusting pH to 4 with aqueous sodium hydrogen carbonate, the organic layer was separated, washed with brine, dried over magnesium sulfate and evaporated. The residue was chromatographed on silica gel (400 ml) eluting with a mixture of n-hexane and ethyl acetate (9:1–5:5 V/V) to give (3S,4R)-4-[(E)-4-{(2S)-1-allyloxycarbonylpyrrolidin-2-yl}-3-methyl-2-oxo-3-butenyl]-3[(1R)-1-t-butyldimethylsilyloxyethyl]-2-oxoazetidine (9.96 g).

IR (CH$_2$Cl$_2$): 3420, 1760, 1695, 1670 cm$^{-1}$
NMR (CDCl$_3$, δ): 0.10 (6H, s), 0.90 (9H, s), 1.23 (3H, d, J=6Hz), 1.50–2.44 (4H, m), 1.87 (3H, d, J=1Hz), 2.61–3.30 (3H, m), 3.40–3.74 (2H, m), 3.80–4.40 (2H, m), 4.47–4.86 (3H, m), 5.05–5.46 (2H, m), 5.63–6.30 (1H, m), 6.08 (1H, br s), 6.48 (1H, dq, J=1, 8Hz)

Preparation 2-(2)

(3S,4R)-4-[4-{(2S,4R)-1-Allyloxycarbonyl-4-t-butyldimethylsilyloxypyrrolidin-2-yl}-3-methyl-2-oxo-3-butenyl]-3-[(1R)-1-t-butyldimethylsilyloxyethyl]-2-oxoazetidine (10.30 g) was obtained in substantially the same manner as that of Preparation 2-(1).

IR (CH$_2$Cl$_2$): 3420, 1760, 1690, 1660 cm$^{-1}$
NMR (CDCl$_3$, δ): 0.07 (12H, s), 0.88 (18H, s), 1.19 (3H, d, J=6Hz), 1.84 (3H, s), 1.45–2.30 (2H, m), 2.60–3.27 (3H, m), 3.52 (2H, d, J=3Hz), 3.80–4.96 (6H, m), 4.96–5.40 (2H, m), 5.40–6.15 (1H, m), 6.07 (1H, br s), 6.30–6.54 (1H, m)

Preparation 3-(1)

To a solution of (3S,4R)-4-[(E)-4-{(2S)-1-allyloxycarbonylpyrrolidin-2-yl}-3-methyl-2-oxo-3-butenyl]-3-[(1R)-1-t-butyldimethylsilyloxyethyl]-2-oxoazetidine (9.96 g) in toluene (150 ml) was added allyl glyoxylate monohydrate (3.68 g). The resulting mixture was heated to reflux with azeotropic removal of water for hours. Evaporation of the solvent gave a residue of allyl 2-[(3S,4R)-4-[(E)-4-{(2S)-1-allyloxycarbonylpyrrolidin-2-yl}-3-methyl-2-oxo-3-butenyl]-3-{(1R)-1-t-butyldimethylsilyloxyethyl}-2-oxoazetidin-1-yl]glyoxylate, which was dissolved in xylene. After evaporation of the solvent in vacuo, the residue was dissolved in dichloromethane (150 ml). To this solution were added successively 2,6-lutidine (2.75 ml) and thionyl chloride (1.95 ml) at −20° C. After stirring at −20° C. for 15 minutes, the reaction mixture was poured into a mixture of ethyl acetate (500 ml) and water (500 ml) at 5° C. After adjusting pH to around 6.5 with aqueous sodium hydrogen carbonate, the organic layer was separated, washed with brine, dried over magnesium sulfate and evaporated. The residue was dissolved in degassed N,N-dimethylformamide (80 ml), and to the solution were added 2,6-lutidine (2.75 ml) and triphenylphosphine (1.29 g). After standing for 6 hours at ambient temperature, the reaction mixture was poured into a mixture of ethyl acetate (400 ml) and water (400 ml). The separated organic layer was washed in turn with water, cold 1N hydrochloric acid, aqueous sodium hydrogen carbonate and brine, and dried over magnesium sulfate. Evaporation of the solvent gave a residue, which was chromatographed on silica gel (200 ml) eluting with a mixture of n-hexane and ethyl acetate (9:1–4:6 V/V) to give allyl 2-[(3S,4R)-4-[(E)-4-{(2S)-1-allyloxycarbonylpyrrolidin-2-yl}-3-methyl-2-oxo-3-20 butenyl]-3 -{(1R)-1-t-butyl-dimethylsilyloxyethyl}-2-oxoazetidin-1-yl]-2-triphenylphosphoranylideneacetate (9.78 g).

IR (CH$_2$Cl$_2$): 1740, 1690, 1660 cm$^{-1}$
NMR (CDCl$_3$, δ): −0.20–0.10 (6H, m), 0.50–0.90 (9H, m), 0.90–1.32 (3H, m), 1.50–2.35 (7H, m), 2.35–3.15 (3H, m), 3.15–3.65 (2H, m), 3.92–4.72 (7H, m), 4.90–5.48 (4H, m), 5.58–6.15 (2H, m), 6.30–6.73 (1H, m), 7.20–7.95 (15H, m)

Preparation 3-(2)

Allyl 2-[(3S,4R)-4-[4-{(2S,4R)-1-allyloxycarbonyl-4-t-butyldimethylsilyloxypyrrolidin-2-yl}-3-methyl-2-oxo-3-butenyl]-3-{(1R)-1-t-butyldimethylsilyloxyethyl}-2-oxoazetidin-1-yl]-2-triphenylphenylphosphoranylideneacetate (11.39 g) was obtained in substantially the same manner as that of Preparation 3-(1).

IR (CH$_2$Cl$_2$): 1740, 1695, 1660 cm$^{-1}$
NMR (CDCl$_3$, δ): −0.16–0.12 (12H, m), 0.56–0.95 (18H, m), 0.95–1.40 (3 H, m), 1.40–2.32 (5H, m), 2.32–3.22 (3H, m), 3.22–3.88 (2H, m), 3.88–4.98 (8H, m), 4.98–5.58 (4H, m), 5.58–6.33 (2H, m), 6.33–6.80 (1H, m), 7.30–7.95 (15H, m)

Preparation 4

To a solution of diisopropylamine (7.7 ml) in tetrahydrofuran (60.0 ml) was added dropwise a 1.55M solution of n-butyllithium in n-hexane (32.3 ml) at −78° C. The mixture was allowed to warm to 0° C., stirred at 0° C. for 30 minutes, and cooled to −78° C. to give ca. 0.5M lithium diisopropylamide solution. To a solution of allyl 2-[(3S,4R)-3-{(1R)-1-t-butyldimethylsilyloxyethyl}-4-{(1R)-1-methyl-2-oxopropyl}-2-oxoazetidin-1-yl]-2-triphenylphosphoranylideneacetate (2.50 g) in tetrahydrofuran (40 ml) was added dropwise the lithium diisopropylamide solution (9.50 ml) obtained above at −78° C. After stirring for 30 minutes at −78° C., to the mixture was added a solution of (2S)-1-allyloxycarbonyl-2-formylpyrrolidine (1.39 g) in tetrahydrofuran (10.0 ml) and the mixture was allowed to warm to −30° C. over a period of 45 minutes. To this mixture was added aqueous ammonium chloride (50 ml) and diluted with ethyl acetate (200 ml). The organic layer was separated, washed in turn with water, aqueous sodium hydrogen carbonate and brine, and dried over magnesium sulfate. Evaporation of the solvent gave a residue which was chromatographed on silica gel (150 ml) eluting with a mixture of dichloromethane and acetone (9:1–8:2 V/V) to give allyl 2-[(3S,4R)-4-[(1R)-4-{(2S)-1-allyloxycarbonylpyrrolidin-2-yl}-4-hydroxy-1-methyl-2-oxobutyl]-3-{ (1R)-1-t-butyldimethylsilyloxyethyl}-2-oxoazetidin-1-yl]-2-triphenylphosphoranylideneacetate (2.36 g).

NMR (CDCl$_3$, δ): −0.1–0.17 (6H, m), 0.87 (9H, s), 0.98–1.52 (6H, m), 1.52–2.32 (4H, m), 2.32–3.15 (5H, m), 3.15–4.40 (6H, m), 4.40–4.76 (4H, m), 4.95–5.45 (4H, m), 5.73–6.20 (2H, m), 7.26–7.98 (15H, m)

Preparation 5

To a solution of (2S,4R)-1-allyloxycarbonyl-4-t-butyldimethylsilyloxy-2-(2-methyl-3-oxo-1-butenyl)-pyrrolidine (9.9 g) in tetrahydrofuran (99 ml) was added 1M solution of tetrabutylammonium fluoride in tetrahydrofuran (32.3 ml) at 0° C. After stirring at room temperature for 1 hour, the reaction mixture was poured into a mixture of ethyl acetate (200 ml) and water (100 ml). The aqueous layer was separated and extracted with ethyl acetate. The combined organic layer was washed twice with 1N hydrochloric acid (25 ml) and then with saturated aqueous sodium bicarbonate, water and brine successively, dried over magnesium sulfate and evaporated. The residue was chromatographed on silica gel (100 ml) eluting with a mixture of n-hexane and ethyl acetate (1:1–1:2 V/V) to give (2S,4R)-1-allyloxycarbonyl-4-hydroxy-2-(2-methyl-3-oxo-1-butenyl)pyrrolidine (5.65 g).

IR (Neat): 3400, 1670 cm$^{-1}$
NMR (CDCl$_3$, δ): 1.60–2.45 (2H, m), 1.82 (3H, s), 2.28 (3H, s), 3.05 (1H, br. s), 3.40–3.80 (2H, m), 4.40–4.65 (3H, m), 4.85 (1H, dd, J=8Hz) 5.05–5.45 (2H, m), 5.60–6.15 (1H, m), 6.45 (1H, d, J=8Hz)

Preparation 6-(1)

To a solution of (2S,4R)-1-allyloxycarbonyl-4-hydroxy-2-(2-methyl-3-oxo-1-butenyl)pyrrolidine (3.0 g) in iodomethane (15 ml) was added silver oxide (10 g), and the mixture was allowed to stand at ambient temperature for 2 days. The resulting precipitate was removed by filtration and the filtrate was evaporated in vacuo. The residue was chromatographed on silica gel (60 ml) eluting with a mixture of n-hexane and ethyl acetate (6:4 V/V) to give (2S,4R)-1-allyloxycarbonyl-4-methoxy-2-(2-methyl-3-oxo-1-butenyl)pyrrolidine (3.23 g).

IR (Neat): 1665, 1700 cm$^{-1}$
NMR (CDCl$_3$, δ): 1.82 (3H, d, J=1Hz), 2.26 (3H, s), 1.5–2.60 (2H, m), 3.32 (3H, s), 3.20–4.13 (3H, m), 4.28–4.90 (3H, m), 4.92–5.40 (2H, m), 5.50–6.10 (1H, m), 6.42 (1H, dq, J=1, 8Hz)

Preparation 6-(2)

To a mixture of (2S,4R)-1-allyloxycarbonyl-4-hydroxy-2-(2-methyl-3-oxo-1-butenyl)pyrrolidine (1.35 g) and methyl isocyanate (0.31 ml) was added a drop of pyridine. The resulting mixture was allowed to stand at ambient temperature for 2 days. Evaporation of the mixture gave a residue, which was chromatographed on silica gel (60 ml) eluting with a mixture of n-hexane and ethyl acetate (1:1 V/V) to give (2S,4R)-1-allyloxycarbonyl-4-(methylcarbamoyloxy)-2-(2-methyl-3-oxo-1-butenyl)pyrrolidine (1.60 g).

IR (Neat): 3350, 1700, 1665 cm$^{-1}$
NMR (CDCl$_3$, δ): 1.83 (3H, d, J=1Hz), 2.30 (3H, s), 1.45–2.55 (2H, m), 2.65–2.90 (3H, m), 3.50–3.91 (2H, m), 4.35–4.92 (4H, m), 4.95–5.40 (3H, m), 5.57–6.20 (1H, m), 6.40 (1H, dq, J=1, 8Hz)

Preparation 6-3)

To a solution of phosgene (2.5 ml) in toluene (15 ml) were added in turn triethylamine (1.45 ml) and a solution of (2S,4R)-1-allyloxycarbonyl-4-hydroxy-2-(2-methyl-3-oxo-1-butenyl)pyrrolidine (2.50 g) in toluene (10 ml) at 0° C. After stirring at 0° C. for 2 hours, the mixture was evaporated in vacuo and the residue was taken up into toluene (15 ml). Evaporation of the solvent gave a residue, which was dissolved in tetrahydrofuran (5 ml). This solution was added dropwise to a solution of dimethylamine (0.89 g) in a mixture of water (50 ml) and tetrahydrofuran (50 ml) under stirring at 0° C., and the stirring was continued for additional 10 minutes at 0° C. After adjusting pH to 7 with 1N hydrochloric acid, the mixture was diluted with ethyl acetate (200 ml). The organic layer was separated, washed with brine, dried over magnesium sulfate and evaporated. The residue was chromatographed on silica gel (100 ml) eluting with a mixture of n-hexane and ethyl acetate (6:4 V/V) to give (2S,4R)-1-allyloxycarbonyl-4-(dimethylcarbamoyloxy)-2 -(2 -methyl-3-oxo-1-butenyl)pyrrolidine (2.65 g). IR (Neat): 1700, 1665 cm$^{-1}$ NMR (CDCl$_3$, δ) : 1.86 (3H, d, J=1 Hz), 2.30 (3H, s), 1.65–2.65 (2 H, m), 2.90 (6H, s), 3.50–3.95 (2H, m), 4.40–4.95 (3H, m), 4.98–5.42 (3H, m), 5.60–6.12 (1H, m), 6.42 (1H, dq, J=1.8 Hz)

Preparation 7

To a suspension of (2S,4R)-2-carboxy-4-hydroxypyrrolidine (300 g) in a mixture of tetrahydrofuran (1.5 l) and water (1.5 l) was added dropwise a solution of allyl chloroformate (292 ml) in tetrahydrofuran (300 ml) at 0° C. while adjusting pH to around 9 with 4N aqueous sodium hydroxide. After stirring at 0° C. for 1 hour at pH 9, the aqueous layer was saturated with sodium chloride, and the mixture was diluted with ethyl acetate (1 l). The aqueous layer was separated, washed with ethyl acetate (1 l). After adjusting pH to around 2 with 12N hydrochloric acid, the emulsion was extracted with two portions of ethyl acetate (1 l×2). The combined extract was dried over magnesium sulfate and evaporated in vacuo to give (2S,4R)-1-allyloxycarbonyl-2-carboxy-4-hydroxypyrrolidine (426.2 g).

NMR (CDCl$_3$+DMSOd$_6$, δ) : 2.05–2.60 (2H, m), 3.63 (2H, d, J=3 Hz), 4.30–4.73 (4H, m), 5.01–6.25 (4H, m)

Preparation 8

To a solution of (2S,4R)-1-allyloxycarbonyl-2-carboxy-4-hydroxypyrrolidine (426 g) in methanol (3 l) was added 36N sulfuric acid (45 ml) at 10° C., and the mixture was allowed to heat to reflux for 2 hours. After cooling to ambient temperature, to this mixture was added triethylamine (430 ml) and the mixture was evaporated in vacuo. The residue was dissolved in ethyl acetate (3 l) and the solution was washed with brine, dried over magnesium sulfate and evaporated to give (2S,4R)-1-allyloxycarbonyl-2-methoxycarbonyl-4-hydroxypyrrolidine (385.6 g).

NMR (CDCl$_3$, δ): 1.60–2.60 (3H, m), 3.60 (2H, d, J=3 Hz), 3.75 (3H, s), 4.37–4.83 (4H, m), 5.10–5.50 (2H, m), 5.60–6.27 (1H, m)

Preparation 9

To a solution of (2S,4R)-1-allyloxycarbonyl-2-methoxycarbonyl-4-hydroxypyrrolidine (210.2 g) and triethylamine (150.2 ml) in dichloromethane (2 l) was added dropwise methanesulfonyl chloride (70.7 ml) at 0° C. After stirring for 1 hour at 0° C., the reaction mixture was washed with brine, dried over magnesium sulfate and evaporated in vacuo to give (2S,4R)-1-allyloxycarbonyl-2-methoxycarbonyl-4-methanesulfonyloxypyrrolidine (281.8 g).

NMR( CDCl$_3$, δ): 1.95–3.00 (2H, m), 3.02 (3H, s), 3.64–3.95 (5H, m), 4.37–4.77 (3H, m), 5.10–5.50 (3H, m), 5.55–6.27 (1H, m)

Preparation 10

To a solution of (2S,4R)-1-allyloxycarbonyl-2-methoxycarbonyl-4-methanesulfonyloxypyrrolidine (281 g) in a mixture of ethanol (0.9 l) and tetrahydrofuran (0.6 l) was added sodium borohydride (69.2 g) at 5° C. and the resulting mixture was allowed to stir for 3.5 hours at 20°–27° C. After cooling to −60° C., the reaction mixture was taken up into a mixture of 12N hydrochloric acid (152.4 ml), water (2.5 l) and ethyl acetate (2.5 l) at 0° C. The organic layer was separated and the aqueous layer was extracted with ethyl acetate (2 l). The organic layer and the extract were combined, washed with 2 portions of brine (500 ml×2), dried over magnesium sulfate and evaporated to give (2S,4R)-1-allyloxycarbonyl-2-hydroxymethyl-4-methanesulfonyloxypyrrolidine (226.9 g).

NMR (CDCl$_3$, δ): 2.00–2.60 (3H, m), 3.03 (3H, s), 3.25–4.30 (5H, m), 4.53–4.73 (2H, m), 5.13–5.50 (3H, m), 5.73–6.27 (1H, m)

Preparation 11

To a solution of (2S,4R)-1-allyloxycarbonyl-2-hydroxymethyl-4-methanesulfonyloxypyrrolidine (20.0 g) in N,N-dimethylformamide (200 ml) were added ammonium chloride (5.74 g) and sodium azide (6.98 g). The resulting mixture was heated at 75° C for 8 hours. After cooling, the mixture was diluted with ethyl acetate (1 l) and aqueous sodium hydrogen carbonate (1 l). The organic layer was separated, washed with brine, dried over magnesium sulfate and evaporated in vacuo to give (2S,4S)-1-allyloxycarbonyl-4-azido-2-hydroxymethylpyrrolidine.

IR (Neat): 2120, 1700 cm$^{-1}$

Preparation 12

To a solution of (2S,4S)-1-allyloxycarbonyl-4-azido-2-hydroxymethylpyrrolidine obtained in Preparation 11 in tetrahydrofuran (120 ml) was added triphenylphosphine (22.5 g) and the resulting mixture was allowed to stand at ambient temperature for 4 hours. To the mixture was added 28% ammonium hydroxide (9.6 ml) and the resulting mixture was allowed to stand at ambient temperature for 12 hours. Evaporation of the solvent gave a residue which was dissolved in toluene, and evaporated in vacuo again. The residue was taken up into a mixture of water (200 ml) and tetrahydrofuran (200 ml). To the mixture was added dropwise allyl chloroformate (9.1 ml) at 0° C. with stirring while adjusting pH to around 8.5 with aqueous potassium carbonate. After stirring at 0° C. for additional 2 hours, the resulting mixture was diluted with ethyl acetate (1 l). The organic layer was separated, washed with brine, dried over magnesium sulfate and evaporated in vacuo. The residue was chromatographed on silica gel (350 ml) eluting with a mixture of n-hexane and ethyl acetate (7:3–1:9 V/V) to give (2S,4S)-1-allyloxycarbonyl-4-(allyloxycarbonyl-amino)-2-hydroxymethylpyrrolidine (11.18 g).

IR (Nujol): 3300, 1700 cm$^{-1}$

NMR (CDCl$_3$, δ): 1.50–2.65 (2H, m), 2.65–4.39 (7H, m), 4.40–4.63 (4H, m), 4.95–5.40 (4H, m), 5.60–6.30 (3H, m)

Preparation 13

To a solution of (2S,4S)-1-allyloxycarbonyl-4-(allyloxycarbonylamino)-2-hydroxymethylpyrrolidine (8.73 g) in N,N-dimethylformamide (40 ml) were added imidazole (6.76 g) and t-butyldimethylsilyl chloride (5.10 g). The resulting mixture was allowed to stand at ambient temperature for 12 hours. The mixture was diluted with ethyl acetate (200 ml), washed in turn with water and brine, dried over magnesium sulfate and evaporated. The residue was chromatographed on silica gel (100 ml) eluting with a mixture of n-hexane and ethyl acetate (7:3 V/V) to give (2S,4S)-1-allyloxycarbonyl-4-(allyloxycarbonylamino)--t-butyldimethylsilyloxymethylpyrrolidine (10.97 g).

IR (Neat): 3330, 1700 cm$^{-1}$

NMR (CDCl$_3$, δ): 0.11 (6H, s), 0.90 (9H, s), 1.50–2.65 (2H, m), 3.13–4.38 (6H, m), 4.40–4.70 (4H, m), 5.00–5.43 (4H, m), 5.55–6.60 (3H, m)

Preparation 14

To a solution of (2S,4S)-1-allyloxycarbonyl-4-(allyloxycarbonylamino)-2-t-butyldimethylsilyloxymethylpyrrolidine (0.97 g) in N,N-dimethylformamide (5.0 ml) was added sodium hydride (0.099 g) at 0° C. After stirring at ambient temperature for 1 hour, the mixture was cooled to 0° C. To the mixture was added methyl iodide (0.31 ml) and the resulting mixture was stirred for additional 4 hours at 0° C. The reaction mixture was diluted with water (50 ml) and ethyl acetate (50 ml). The organic layer was separated, washed with brine, dried over magnesium sulfate and evaporated to give (2S,4S)-1-allyloxycarbonyl-4-(N-allyloxycarbonyl-N-methylamino)-2-t-butyldimethylsilyloxymethylpyrrolidine (1.01 g). IR (Neat): 1700 cm$^{-1}$ NMR (CDCl$_3$, δ): 0.05 (6H, s), 0.90 (9H, s), 1.50–2.30 (2H, m), 2.85 (3H, s), 2.75–4.22 (5H, m), 4.40–4.90 (5H, m), 5.00–5.40 (4H, m), 5.60–6.15 (2H, m)

Preparation 15

To a solution of (2S,4S)-1-allyloxycarbonyl-4-(N-allyloxycarbonyl-N-methylamino)-2-t-butyldimethylsilyloxymethylpyrrolidine (3.73 g) in ethyl acetate (100 ml) was added 12N hydrochloric acid (0.82 ml) at ambient temperature. After stirring at ambient temperature for 30 minutes, to the mixture were added sodium hydrogen carbonate (1.90 g) and cold water (100 ml). The organic layer was separated, washed with brine, dried over magnesium sulfate and evaporated. The residue was chromatographed on silica gel (100 ml) eluting with a mixture of n-hexane and ethyl acetate (7:3–2:8 V/V) to give (2S,4S)-1-allyloxycarbonyl-4-(N-allyloxycarbonyl-N-methylamino)-2-hydroxymethylpyrrolidine (2.04 g).

IR (Neat): 3430, 1680 cm$^{-1}$

NMR (CDCl$_3$, δ): 1.48–2.35 (2H, m), 2.86 (3H, s), 2.80–4.30 (6H, m), 4.40–5.00 (5H, m), 5.00–5.43 (4H, m), 5.67–6.16 (2H, m)

Preparation 16

(2S,4S)-1-Allyloxycarbonyl-4-(N-allyloxycarbonyl-N—methylamino)-2-2. -methyl-3-oxo-1-butenyl)pyrrolidine (2.02 g) was obtained from (2S,4S)-1-allyloxycarbonyl-4-(N-allyloxycarbonyl-N-methylamino)-2-hydroxymethylpyrrolidine (2.04 g) in substantially the same manner as that of Preparation 1—1).

IR (Neat): 1700 cm$^{-1}$

NMR (CDCl$_3$, δ): 1.82 (3H, d, J=1 Hz), 2.30 (3H, s), 1.50–2.70 (2H, m), 2.87 (3H, s), 3.10–4.05 (2H, m), 4.40–4.96 (6H, m), 5.00–5.38 (4H, m), 5.50–6.15 (2H, m), 6.44 (1H, dq, J=1, 8 Hz)

Preparation 17

A solution of the F-propenediethylamine reagent (2.9 ml) in dichloromethane (14 ml) was dropped into a solution of (2S,4R)-1-allyloxycarbonyl-4-hydroxy-2-(2-methyl-3-oxo-1-butenyl)pyrrolidine (3.5 g) in dichloromethane at 0°–5° C. After stirring for 12 hours, the reaction mixture was poured into a stirring mixture of saturated aqueous sodium bicarbonate (50 ml) and ice chips. The mixture was extracted with dichloromethane. The organic layers were washed in turn with water and brine, dried over magnesium sulfate and evaporated under reduced pressure. The oil was purified by column chromatography on silica gel to give (2 S)-1-allyloxycarbonyl-4-fluoro-2-(2-methyl-3-oxo-1-butenyl)pyrrolidine (3.4 g).

IR (Neat): 1670 cm$^{-1}$

NMR (CDCl$_3$, δ): 1.70–2.80 (2H, m), 1.85 (3H, s), 2.30 (3H, s), 3.25–4.05 (2H, m), 4.45–4.70 (2H, d, J=6.0 Hz), 4.70–6.15 (5H, m), 6.50–6.70 (1H, m)

$^{19}$F NMR (CF$_3$CO$_2$H): −92.0 ppm (m)

Preparation 18

To a solution of 1-benzyl-2-t-butyldimethylsilyloxymethyl-5-hydroxymethylpyrrolidine (10 g) in tetrahydrofuran (100 ml) was added portionwise sodium hydride (2.3 g) at 0° C. The mixture was stirred at the same temperature for 30 minutes. And then methyl iodide was added to the mixture. After stirring for an hour at room temperature, water and ethyl acetate was added thereto. The aqueous layer was separated and washed twice with ethyl acetate. The combined organic layer was washed with saturated aqueous sodium hydrogen carbonate, water and brine successively, dried over magnesium sulfate and evaporated under reduced pressure to give 1-benzyl-2-t-butyldimethylsilyloxymethyl-5-methoxymethylpyrrolidine (9.99 g).

IR (Neat): 1495, 1470 cm$^{-1}$

NMR (CDCl$_3$, δ): 0.08 (6H, s), 0.98 (9H, s), 1.30–2.20 (4H, m), 2.70–3.70 (6H, m), 3.35 (3H, s), 3.96 (2H, s), 7.36 (5H, s)

Preparation 19

1-Allyloxycarbonyl-2-t-butyldimethylsilyloxymethyl-methoxymethylpyrrolidine was obtained in 99% yield in substantially the same manner as that of Preparation 24.

IR (Neat): 1705 cm$^{-1}$

NMR (CDCl$_3$, δ): 0.05 (6H, s), 0.90 (9H, s), 1.70–2.20 (4H, m), 3.10–4.20 (6H, m), 3.32 (3H, s), 4.57 (2H, d, J=5 Hz), 5.06–5.47 (2H, m), 5 70–6.20 (1H, m)

Preparation 20

To a solution of 1-allyloxycarbonyl-2-t-butyldimethylsilyloxymethyl-5-methoxymethylpyrrolidine (9.67 g) in tetrahydrofuran (97 ml) was added dropwise a solution of tetrabutylammonium fluoride in tetrahydrofuran (31 ml) at 0° C. The mixture was allowed to warm to room temperature and stirred for an hour. The mixture was poured into water and ethyl acetate, and the aqueous layer was separated and extracted twice with ethyl acetate. The combined organic layer was washed twice with 1N hydrochloric acid, and with saturated aqueous sodium bicarbonate, water and brine successively, dried over magnesium sulfate and evaporated under reduced pressure to give 1-allyloxycarbonyl-2-hydroxymethyl-5-methoxymethylpyrrolidine (5.60 g).

IR (Neat): 3400, 1680 cm$^{-1}$

NMR (CDCl$_3$, δ): 1.50–2.30 (4H, m), 3.32 (3H, s), 3.20–4.40 (7H, m), 4.60 (2H, d, J=6 Hz), 5.10–5.45 (2H, m), 5.70–6.20 (1H, m)

Preparation 21

1-Allyloxycarbonyl-5-methoxymethyl-2-(2-methyl-3-oxo-1-butenyl)pyrrolidine was obtained in 58.8% yield in substantially the same manner as that of Preparation 25.

IR (Neat): 1700, 1670 cm$^{-1}$

NMR (CDCl$_3$, δ): 1.60–2.30 (4H, m), 1.80 (3H, s), 2.26 (3H, s), 3.35 (3H, s), 3.48 (2H, d, J=5 Hz), 4.10 (1H, m), 4.46–4.80 (3H, m), 5.03–5.40 (2H, m), 5.60–6.15 (1H, m), 6.52 (1H, d, J=8 Hz)

Preparation 22

To a suspension of lithium aluminum hydride (10.25 g) in tetrahydrofuran (550 ml) was added dropwise a solution of 1-benzyl-2,5-bis(ethoxycarbonyl)pyrrolidine (55 g) in tetrahydrofuran (100 ml). The reaction mixture was stirred for 30 minutes at 0° C., allowed to warm to room temperature and then stirred at the same temperature for 1 hour. And then water was added carefully until excess lithium aluminum hydride was decomposed. After the precipitate was filtered off, the filtrate was evaporated under reduced pressure to give crude 1-benzyl-2,5-bis(hydroxymethyl)pyrrolidine (38.52 g).

IR (Neat): 3300 cm$^{-1}$

NMR (CDCl$_3$, δ): 1.73–1.85 (4H, m), 2.10 (2H, br. s), 3.00 (2H, m), 3.30–3.45 (4H, m), 3.78 (2H, s), 7.28 (5H, s)

Preparation 23

To a solution of 1-benzyl-2,5-bis(hydroxymethyl)pyrrolidine (30 g) and imidazole (27.8 g) in dimethylformamide (300 ml) was added portionwise t-butyldimethylsilyl chloride (20.4 g) at room temperature. After stirring for 1 hour at room temperature, water (0.9 l) and ethyl acetate (1.4 l) was added to the mixture. After shaking, aqueous layer was separated and extracted twice with ethyl acetate. The combined organic layer was washed with water (3 times) and brine, dried over magnesium sulfate and evaporated under reduced pressure. The residue was column chromatographed on silica gel (eluent:nexane/ethyl acetate, 8:2–7:3 V/V) to give 1-benzyl-5-t-butyldimethylsilyloxymethyl-2-hydroxymethylpyrrolidine (16.8 g).

IR (Neat): 3400 cm$^{-1}$

NMR (CDCl$_3$, δ): 0.10 (6H, s), 0.98 (9H, s), 1.80–2.00 (4H, m), 2.83 (1H, br. s), 3.06 (2H, m), 3.40 (2H, s), 3.45 (2H, s), 3.90 (2H, s), 7.37 (5H, s)

Preparation 24

To a solution of 1-benzyl-5-t-butyldimethylsilyloxymethyl-2-hydroxymethylpyrrolidine (6.3 g) in methanol (63 ml) was added palladium hydroxide on carbon (630 mg) under nitrogen atmosphere. The apparatus was evacuated to remove nitrogen, then filled with hydrogen, and the mixture was stirred under hydrogen atmosphere until 19 mmol of hydrogen was absorbed. The palladium hydroxide on carbon was filtered off and the solvent was removed under reduced pressure to give 5-t-butyldimethylsilyloxymethyl-2-hydroxymethylpyrrolidine (4.0 g). To a solution of this residue in tetrahydrofuran (60 ml) and water (30 ml) were added sodium bicarbonate (4.10 g) and then allyl chloroformate (1.42 ml) at room temperature. After stirring for 2 hours, sodium bicarbonate (2.1 g) and allyloxycarbonyl chloride (1.42 ml) was added. After stirring for an hour, ethyl acetate (100 ml) and water (50 ml) were added and the aqueous layer was separated and extracted twice with ethyl acetate. The combined organic layer was washed with 1N hydrochloric acid, saturated aqueous sodium bicarbonate, water and brine successively, dried over magnesium sulfate and evaporated under reduced pressure. The residue was column chromatographed on silica gel (eluent:hexane/ethyl acetate, 9:1–4:1 V/V) to give 1-allyloxycarbonyl-5-t- butyldimethylsilyloxymethyl-2-hydroxymethylpyrrolidine (4.91 g).

IR (Neat): 3400, 1690 cm$^{-1}$
NMR (CDCl$_3$, δ): 0.08 (6H, s), 0.90 (9H, s), 1.60–2.30 (4H, m), 3.30–4.50 (7H, m), 4.58 (2H, d, J=6 Hz), 5.10–5.50 (2H, m), 5.70–6.20 (1H, m)

Preparation 25

To a solution of 1-allyloxycarbonyl-5-t-butyldimethylsilyloxymethyl- 2-hydroxymethylpyrrolidine (4.9 g) in dimethyl sulfoxide (49 ml) and triethylamine (7.25 ml) was added portionwise pyridine sulfur trioxide (8.29 g) while the reaction temperature was maintained at 25° C. during the addition. After stirring for an hour, the mixture was added to ice-cooled water (245 ml), stirred for appropriate time and extracted three times with a mixture of ethyl acetate and hexane (1:1 v/v). The combined organic layer was washed twice with water, 1N hydrochloric acid, saturated aqueous sodium bicarbonate, water and brine, dried over magnesium sulfate, and evaporated under reduced pressure. To the residue was added toluene (30 ml) and 3-triphenylphosphoranylidenebutan-2-one (5.9 g) at room temperature. The mixture was stirred at 70° C. for 6 hours and evaporated under reduced pressure. Hexane was added to the residue and the mixture was stirred for an hour. The precipitate was filtered off and the filtrate was evaporated under reduced pressure. The residue was column chromatographed on silica gel to give 1-allyloxycarbonyl-5-t-butyldimethylsilyloxymethyl-2 -(2-methyl-3-oxo-1-butenyl)pyrrolidine (4.49 g).

IR (Neat): 1700, 1670 cm$^{-1}$
NMR (CDCl$_3$, δ): 0.06 (3H, s), 0.09 (3H, s), 0.93 (9H, s), 1.82 (3H, s), 1.82–2.20 (4H, m), 2.30 (3H, s), 3.73 (2H, d, J=6 Hz), 3.70–4.20 (2H, m), 4.40–4.80 (2H, m), 5.06–5.43 (2H, m), 5.60–6.13 (1H, m), 6.50 (1H, d, J=9 Hz)

Preparation 26

To a suspension of lithium aluminum hydride (16.2 g) in tetrahydrofuran (1 l) was added 1-benzyl-4-methoxycarbonyl-2-oxopyrrolidine (50 g) under reflux for one hour and the mixture was refluxed for 2 hours. A solution of water (15.5 ml) and tetrahydrofuran (50 ml) was added to the mixture under reflux. After cooling, insoluble material was filtered off and the filtrate was concentrated under reduced pressure to give 1-benzyl-3-hydroxymethylpyrrolidine (43.45 g).

IR (Neat): 3350–3050 cm$^{-1}$
NMR (DMSO-d$_6$, δ): 1.1–1.9 (1H, m), 1.9–2.0 (1H, m), 2.0–2.6 (5H, m), 3.1–3.4 (2H, m), 3.50 (2H, s), 4.3–4.6 (1H, m), 7.23 (5H, s)
MS: 191 (M$^+$), 114 (M$^+$ –77), 100 (M$^+$ –91)

Preparation 27

Imidazole (30.0 g) was added to a solution of 1-benzyl-3-hydroxymethylpyrrolidine (43.45 g) and t-butyldimethylsilyl chloride (48.5 g) in dimethylformamide(150 ml) under ice-cooling. The mixture was stirred at the same temperature for 2 hours and at ambient temperature for 15 hours. The mixture was poured into water (600 ml), extracted twice with ethyl acetate (200 ml and 100 ml), dried over magnesium sulfate and evaporated under reduced pressure to give a syrup. The syrup was subjected to a column chromatography on silica gel (500 g) and eluted with a mixture of methanol and dichloromethane (5:95 V/V) to give 1-benzyl-3-t-butyldimethylsilyloxymethylpyrrolidine (60.15 g).

NMR (CDCl$_3$, δ): 0.03 (6H, s), 0.85 (9H, s), 1.2–1.9 (1H, m), 1.9–2.1 (1H, m), 2.1–2.9 (5H, m), 3.77 (2H, d, J=6 Hz), 3.53 (2H, s), 7.22 (5H, s)

Preparation 28

A solution of 1-benzyl-3-t-butyldimethylsilyloxymethylpyrrolidine (60.10 g) and allyl chloroformate (25.27 ml) in toluene (600 ml) was heated at 60° C for one hour. The mixture was concentrated under reduced pressure to give a syrup. The syrup was subjected to a column chromatography on silica gel (500 g), and eluted with a mixture of ethyl acetate and hexane (1:9–3:7, V/V) to give 1-allyloxycarbonyl-3-t-butyldimethylsilyloxymethylpyrrolidine (30.00 g).

IR (Neat): 1710–1700 cm$^{-1}$
NMR (CDCl$_3$, δ): 0.03 (6H, s), 1.90 (9H, s), 1.5–2.5 (2H, m), 3.0–3.7 (7H, m), 4.5–4.7 (2H, m), 5.0–5.4 (2H, m), 5.7–6.2 (1H, m)

Preparation 29

A solution of 1-allyloxycarbonyl-3-t-butyldimethylsilyloxymethylpyrrolidine (29.95 g) in a mixture of concentrated hydrochloric acid (15 ml) and methanol (150 ml) was stirred at ambient temperature for one hour. A 28% solution of sodium methoxide in methanol (35 ml) was added to the mixture. Insoluble material was filtered off and the filtrate was concentrated under reduced pressure to give a syrup. The syrup was subjected to a column chromatography on silica gel (400 g) and eluted with ethyl acetate to give 1-allyloxycarbonyl-3-hydroxymethylpyrrolidine (19.01 g).

IR (Neat): 3450–3200, 1710–1650 cm$^{-1}$
NMR (CDCl$_3$, δ): 1.5–2.9 (4H, m), 3.0–3.8 (6H, m), 4.4–4.7 (2H, m), 5.0–5.4 (2H, m), 5.7–6.2 (1H, m)
MS: 185 (M$^+$)

Preparation 30

A solution of dimethyl sulfoxide (13.03 ml) in dichloromethane (25 ml) was dropwise added to a solution of oxalyl chloride (9.1 ml) in dichloromethane (100 ml) below –65° C. with stirring. The mixture was stirred at the same temperature for 30 minutes. A solution of 1-allyloxycarbonyl-3-hydroxymethylpyrrolidine (17.0 g) in dichloromethane was added to the mixture at the same temperature. The mixture was stirred below –65° C. for 30 minutes, followed by dropwise addition of triethylamine (38.5 ml) below −65° C. The cooling bath was then removed and the reaction mixture was allowed to warm up to ambient temperature, washed with water (250 ml×2), 1N hydrochloric acid (150 ml), saturated sodium hydrogen carbonate (150 ml) and brine (150 ml) in turn, dried over magnesium sulfate, and concentrated under reduced pressure to give a syrup. The syrup was subjected to a column chromatography on silica gel (200 g) and eluted with a mixture of methanol and dichloromethane (1:99 V/V) to give 1-allyloxycarbonyl-3-formylpyrrolidine (13.50 g).

IR (Neat): 1730–1675 cm$^{-1}$

NMR (CDCl$_3$, δ): 1.7–2.5 (2H, m), 2.9–4.9 (7H, m), 4.5–4.7 (2H, m), 5.1–5.4 (2H, m), 5.7–6.2 (1H, m), 9.65 (1H, s)

Preparation 31

A solution of 1-allyloxycarbonyl-3-formylpyrrolidine (13.45 g) and 3-triphenylphosphoranylidenebutan-2-one (25.60 g) in dichloromethane (15 ml) was refluxed for 20 hours. The mixture was concentrated under reduced pressure to give a syrup. The syrup was subjected to a column chromatography on silica gel (200 g) and eluted with a mixture of ethyl acetate and hexane (4:6 V/V) to give 1-allyloxycarbonyl-3-(2-methyl-3-oxo-1-butenyl)-pyrrolidine (16.52 g).

IR (Neat): 1710–1650 cm$^{-1}$

NMR (CDCl$_3$, δ): 1.82 (3H, s), 2.28 (3H, s), 4.5–4.7 (2H, m), 5.0–5.4 (2H, m), 5.7–6.1 (1H, m)

MS: 237 (M$^+$), 222 (M$^+$−15), 196 (M$^+$−41)

Preparation 32

(2R)-1-Allyloxycarbonyl-2-(2-methyl-3-oxo-1-butenyl)pyrrolidine (2.86 g) was obtained by reacting (2R)-1-allyloxycarbonyl-2-methoxycaronylpyrrolidine (3.60 g) with 3-triphenylphosphoranylidenebutan-2-one (6.18 g) in substantially the same manner as that of Preparation 34.

IR (CH$_2$Cl$_2$): 1690, 1670 cm$^{-1}$

NMR (CDCl$_3$, δ): 1.83 (3H, d, J=1 Hz), 1.50–2.43 (4H, m), 2.27 (3H, s), 3.34–3.75 (2H, m), 4.40–4.80 (3H, m), 5.00–5.43 (2H, m), 5.59–6.20 (1H, m), 6.45 (1H, dq, J=1, 8 Hz)

Preparation 33

A solution of 2-carboxypiperidine (50 g) in tetrahydrofuran (200 ml) and water (200 ml) was adjusted to around pH 9.5 with 20% aqueous sodium hydroxide. To the solution was added dropwise allyl chloroformate (45 ml) at 5° C., while adjusting pH to around 9.5 with 20% aqueous sodium hydroxide. After stirring for 30 minutes at 0° C., the mixture was washed with ethyl acetate. After addition of ethyl acetate (200 ml), the mixture was adjusted to around pH 2.0 with concentrated hydrochloric acid (30 ml) and 1N hydrochloric acid. The mixture was extracted with ethyl acetate (200 ml), washed with brine and dried over magnesium sulfate. Evaporation of the solvent gave an oil of 1-allyloxycarbonyl-2-carboxypiperidine (88.7 g), which was dissolved in methanol (440 ml). To this solution was added dropwise, sulfuric acid (6.9 ml) and the mixture was refluxed for 2 hours. To the mixture was added dropwise triethylamine (29.5 ml) at 20° C. Evaporation of the solvent gave a residue which was taken up into a mixture of ethyl acetate (400 ml) and water (100 ml). The organic layer was separated, washed with water, 1N aqueous hydrochloric acid, brine, 5% aqueous sodium hydrogen carbonate and brine successively, and dried over magnesium sulfate. Evaporation of the solvent gave 1-allyloxycarbonyl-2-methoxycarbonylpiperidine (92.5 g).

IR (Neat): 1740, 1700 cm$^{-1}$

NMR (CHCl$_3$, δ): 1.05–2.40 (6H, m), 3.00 (1H, m), 3.72 (3H, s), 4.50 (1H, br. d, J=13 Hz), 4.58 (2H, d, J=5 Hz), 4.88 (1H, br. s), 5.05–5.40 (2H, m), 5.68–6.17 (1H, m)

Preparation 34

To a solution of 1-allyloxycarbonyl-2-methoxycarbonylpiperidine (10 g) in toluene (60 ml) was added dropwise diisobutylaluminum hydride (1M solution in toluene) (57 ml) at −70° C. After stirring at −70° C. for 30 minutes, the reaction mixture was poured into a mixture of concentrated hydrochloric acid (25 ml) and water (100 ml) at 5° C. After stirring at 5° C. for 15 minutes, the organic layer was separated, washed in turn with 1N hydrochloric acid (20 ml), 25% potassium sodium tartrate (20 ml) and brine (20 ml), dried over magncsium sulfate and filtered. The filtrate was concentrated to a volume of 40 ml. To this solution was added 3-triphenylphosphoranylidenebutan-2-one (16.1 g) and the mixture was stirred at 70° C. for 5 hours. After cooling to ambient temperature, the resulting precipitate was removed by filtration. The filtrate was evaporated to give a residue, which was taken up into ethyl acetate. The resulting precipitate was removed by filtration and the filtrate was evaporated in vacuo. The residue was chromatographed on silica gel (300 ml) eluting with a mixture of n-hexane and ethyl acetate (10:1–5:1 V/V) to give 1-allyloxycarbonyl-2-(2-methyl-3-oxo-1-butenyl)piperidine (10.9 g).

IR (CHCl$_3$): 1680 cm$^{-1}$

NMR (CDCl$_3$, δ): 1.88 (3H, br s), 2.34 (3H, s), 2.80–3.20 (1H, m), 4.00–4.25 (1H, m), 4.50–4.65 (2H, m), 5.05–5.38 (3H, m), 5.70–6.11 (1H, m), 6.74 (1H, br. d, J=9 Hz)

Preparation 35

To a mixture of dimethylformamide (4.2 ml) and tetrahydrofuran (10 ml) was added phosphorus oxychloride (4.2 ml) at 5° C. After stirring at 5° C. for 30 minutes, to the mixture were added successively tetrahydrofuran (60 ml) and N-allyloxycarbonyl-N-methylglycine (8.7 g). The mixture was stirred for 30 minutes at 5° C. (solution A). To a solution of (2S)-1-allyloxycarbonyl-2-(2-methyl-3-oxo-1-butenyl)pyrrolidine (10.0 g) in tetrahydrofuran (160 ml) were added successively triphenylphosphine (5.5 g), 5,5-dimethyl-1,3-cyclohexanedione (dimedone) (5.8 g), acetic acid (4.8 ml) and tetrakis(triphenylphosphine)-palladium(0) (2.4 g). After stirring at ambient temperature for 30 minutes, the mixture was taken up into a mixture of ethyl acetate (100 ml) and water (100 ml). After adjusting to around pH 2 with 1N hydrochloric acid, the aqueous layer was separated, washed with e&hyl acetate and tetrahydrofuran (200 ml) was added thereto. After adjusting to around pH 8.5 with 20% aqueous sodium hydroxide, to the mixture was added dropwise the solution A. After stirring at 5° C. for 1 hour, the mixture was extracted with ethyl acetate. The organic layer was washed with water and dried over magnesium sulfate. Removal of the solvent gave a residue, which was chromatographed on silica gel (300 ml) eluting with a mixture of n-hexane and ethyl acetate (5:5–3:7 V/V) to give (2S)-1-(N-allyloxycarbonyl-N-methylaminoacetyl)-2-(2-methyl-3-oxo-1-butenyl)pyrrolidine (3.4 g).

NMR (CDCl$_3$, δ): 1.90 (3H, br. s), 2.30 (3H, s), 3.05 (3H, s), 3.5–4.1 (4H, m), 4.58 (2H, br. d, J=5 Hz), 4.7–5.0 (1H, m), 5.1–5.4 (2H, m), 5.7–6.2 (1H, m), 6.3–6.6 (1H, m)

Preparation 36

A solution of 1-benzhydryl-3-hydroxymethylazetidine (4.3 g) in methanol (80 ml) containing conc. hydrochloric acid (2.7 ml) was hydrogenated under the pressure of 60 lb/inch$_2$ in the presence of 10% palladium on carbon. The catalyst was removed off and the filtrate was evaporated, and the resulting residue was dissolved in water and extracted with diethyl ether (100 ml). The aqueous solution was adjusted to pH 6.8 using 10% aqueous sodium hydroxide and extracted with ethyl acetate. To the aqueous solution was added tetrahydrofuran (30 ml) and the solution was cooled to 0°–5° C. Allyl chloroformate (1.35 ml) in tetrahydrofuran (5 ml) was dropwise added thereto while keeping pH to 7.5–8.0. After stirring for 1 hour, ethyl acetate (30 ml) was added and the separated organic layer was dried and evaporated. The remained residue was chromatographed on silica gel eluting with a solution of 3–5% methanol in chloroform to give 1-allyloxycarbonyl-3-hydroxymethylazetidine (0.97 g).

IR (Neat): 1680 cm$^{-1}$

NMR (CDCl$_3$, δ): 2.20–2.40 (1H, m), 2.50–2.90 (1H, m), 3.63–4.18 (6H, m), 4.42–4.60 (2H, m), 5.05–5.35 (2H, m), 5.65–6.10 (1H, m)

Preparation 37

To a solution of oxalyl chloride (6.3 g) in methylene chloride (85 ml) was added dimethyl sulfoxide (3.87 g) at −60° C. and stirred was stirred for 15 minutes. A solution of 1-allyloxycarbonyl-3-hydroxymethylazetidine (6.8 g) in methylene chloride (21 ml) was then added thereto and the mixture was stirred at −60° C. for 30 minutes. Triethylamine (20 g) was dropwise added thereto. To the mixture was added water (50 ml) and organic layer was separated washed with water, dried over magnesium sulfate, evaporated and co-evaporated with benzene to give an oily residue. The residue was dissolved in methylene chloride (160 ml) and 3-triphenylphosphoranylidenebutan-2-one (11.8 g) was added thereto and the mixture was stirred overnight at room temperature. The evaporated residue was triturated with ethyl acetate and the insoluble material was filtered. The filtrate was applied on silica gel column using a mixture of n-hexane and ethyl acetate. The main fractions were evaporated to give 1-allyloxycarbonyl-3-(2-methyl-3-oxo-1-butenyl)azetidine (7.06 g).

IR (Neat): 1680 cm$^{-1}$

NMR (CDCl$_3$, δ): 1.75 (3H, d, J=1 Hz), 2.34 (3H, s), 3.40–3.95 (3H, m), 4.17–4.60 (4H, m), 5.06–5.40 (2H, m), 5.70–6.13 (1H, m), 6.63–6.85 (1H, d, J=7 Hz)

Preparation 38

To a solution of (2S)-2-t-butyldimethylsilyloxymethyl 1-methyl-5-pyrrolidone (16 g) in tetrahydrofuran (160 ml) was added Lawesson's Reagent [2,4-bis(4-methoxyphenyl)-1,3-dithia-2,4-diphosphetane-2,4-disulfide] (14.6 g) at ambient temperature. After stirring at 60° C. under nitrogen for 1 hour, the solvent was removed. The residue was chromatographed on silica gel eluting with a mixture of acetone and dichloromethane (1:9 V/V) to give (2S)-2-t-butyldimethylsilyloxymethyl-1-methyl-5-thioxopyrrolidine (17.0 g).

NMR (CDCl$_3$, δ): 0.09 (6H, s), 0.91 (9H, s), 1.6–2.3 (2H, m), 2.8–3.2 (2H, m), 3.26 (3H, s), 3.5–4.1 (3H, m)

Preparation 39

To a solution of (2S)-2-t-butyldimethylsilyloxymethy-1-methyl-5-thioxopyrrolidine (9.0 g) in tetrahydrofuran (180 ml) was added methyl iodide (10 ml). After stirring at ambient temperature under nitrogen for 12 hours, evaporation of the solvent gave a residue, which was taken up into diethyl ether. The obtained solid was washed with diethyl ether and dissolved in 10% ammonia in methanol (100 ml). After stirring at 0° C. for 1 hour, the solvent was evaporated. The residue was dissolved in tetrahydrofuran (100 ml) and to the solution were added triethylamine (7.8 ml) and allyl chloroformate (3.0 ml). After stirring at 0° C. for 1 hour, the solvent was evaporated and the residue was chromatographed on silica gel eluting with a mixture of n-hexane and ethyl acetate (1:1 V/V) to give (2S)-5-allyloxycarbonylimino-2-t-butyldimethylsilyloxymethyl-1-methylpyrrolidine (5.1 g).

IR (CH$_2$Cl$_2$): 1675 cm$^{-1}$

NMR (CDCl$_3$, δ): 0.09 (6H, s), 0.86 (9H, s), 1.8–2.3 (2H, m), 2.8–3.2 (2H, m), 2.99 (3H, s), 3.6–3.9 (3H, m), 4.50 (2H, d, J=6 Hz), 5.0–5.4 (2H, m), 5.7–6.2 (1H, m)

Preparation 40

To a solution of (2S)-5-allyloxycarbonylimino-2-t-butyldimethylsilyloxym,athyl-1-methylpyrrolidine (1.0 g) in methanol (30 ml) was added conc. hydrochloric acid (1 ml) at 0° C. After stirring at ambient temperature for 12 hours, saturated aqueous sodium bicarbonate was added to the mixture and the solvent was evaporated. The residue was dissolved in ethyl acetate and washed in turn with water and brine. The dried solution was evaporated in vacuo to give (2S)-5-allyloxycarbonylimino-2-hydroxymethyl-1-methylpyrrolidine (0.65 g).

IR (Neat): 3300–3400, 1660–1680 cm$^{-1}$

NMR (CDCl$_3$, δ): 3.01 (3H, s), 2.8–3.2 (2H, m), 3.3–3.8 (4H, m), 4.4–4.6 (2H, m), 5.0–5.5 (2H, m), 5.7–6.2 (1H, m)

Preparation 41

To a solution of oxalyl chloride (0.52 ml) in dichloromethane (15 ml) was added dropwise dimethyl sulfoxide (0.60 ml) at −78° C. After stirring at −78° C. for 10 minutes, to the mixture was added dropwise a solution of (2S)-5-allyloxycarbonylimino-2-hydroxymethyl-1-methylpyrrolidine (0.63 g) in dichloromethane (10 ml). After stirring at −78° C. for 10 minutes, to the mixture was added dropwise triethylamine (2.1 ml) and the resulting mixture was allowed to warm to 0° C. The mixture was washed with water and brine, dried over magnesium sulfate, and evaporated. The residue was chromatographed on silica gel eluting with a mixture of acetone and dichloromethane (1:4 V/V) to give (2S)-5-allyloxycarbonylimino-2-formyl-1-methylpyrrolidine (0.46 g).

IR (CH$_2$Cl$_2$): 1650–1680 cm$^{-1}$

NMR (CDCl$_3$, δ): 3.11 (3H, s), 4.0–4.3 (1H, m), 4.4–4.7 (2H, m), 5.0–5.4 (2H, m), 5.7–6.2 (1H, m)

Preparation 42

To a solution of (2S)-5-allyloxycarbonylimino-2-formyl-1-methylpyrrolidine (0.46 g) in toluene (20 ml) was added 3-triphenylphosphoranylidenebutan-2-one and the mixture was stirred at 80° C. for 2 hours. The solvent was evaporated and the residue was chromatographed on silica gel eluting with a mixture of n-hexane and ethyl acetate (1:2 V/V) to give (2S)-5-allyloxycarbonylimino-1-methyl-2-(2-methyl-3-oxo-1-butenyl)pyrrolidine (0.54 g).

IR (CH$_2$Cl$_2$): 1670 cm$^{-1}$

NMR (CDCl$_3$, δ): 1.90 (3H, d, J=1 Hz), 2.32 (3H, s), 2.97 (3H, s), 2.9–3.3 (2H, m), 4.3–4.7 (3H, m), 5.0–5.4 (2H, m), 5.7–6.2 (1H, m), 6.31 (1H, dd, J=8 Hz, 1 Hz)

Preparation 43

The mixture of (3R)-4-benzyl-3-hydroxymethylmorpholine (2.23 g) and 10% palladium on carbon (wet, 1.11 g) and ethanol was stirred under hydrogen atmosphere for 2 hours. The catalyst was filtrated and the filtrate was evaporated. The oily residue was taken up in ethyl acetate (50 ml) and water (50 ml). The mixture was treated with allyl chloroformate (1.23 ml) at pH 9–10 and stirred for 30 minutes. The separated organic layer was washed with brine (50 ml×2) and dried over magnesium sulfate. The solvent was removed in vacuo and the residue was chromatographed on silica gel (40 ml) eluting with ethyl acetate in hexane (5–50%) to give (3R)-4-allyloxycarbonyl-3-hydroxymethylmorpholine (1.22 g).

NMR (CDCl$_3$, δ): 2.75 (1H, br. s), 2.9–4.4 (9H, m), 4.4–4.7 (2H, m), 4.9–5.4 (2H, m), 5.6–6.2 (1H, m)

Preparation 44

To a stirred mixture of (3R)-4-allyloxycarbonyl-3-hydroxymethylmorpholine (1.22 g) and triethylamine (2.96 ml) in dimethyl sulfoxide (12.2 ml) was added sulfur trioxide pyridine complex (3.37 g) at 10° C. After stirring at ambient temperature for one hour, the reaction mixture was poured into water and extracted with ethyl acetate and hexane. The separated organic layer was washed in turn with aqueous hydrogen chloride (1N), aqueous sodium hydrogen carbonate and brine, and dried over magnesium sulfate. The solution was evaporated. The residue was chromatographed on silica gel (40 ml) eluted with ethyl acetate in hexane (5–10%) to give (3R)-4-allyloxycarbonyl-3-(2-methyl-3-oxo-1-butenyl)morpholine (971 mg).

NMR (CDCl$_3$,): 1.86 (3H, d, J=1 Hz), 2.35 (3H, s), 3.1–4.1 (6H, m), 4.4–4.7 (2H, m), 4.7–5.0 (1H, m), 5.0–5.3 (2H, m), 5.6–6.2 (1H, m), 6.88 (1H, dq, J=9 Hz, 1 Hz)

Preparation 45-(1)

To a solution of (3R,4R)-4-acetoxy-3-[(1R)-1-t-butyldimethylsilyloxyethyl]-2-oxoazetidine (2.90 g) and N-ethylpiperidine (1.35 ml) in dichloromethane (15 ml) was added trimethylsilyl trifluoromethanesulfonate (1.95 ml) at −20° C., and the resulting mixture was stirred at 0° C. for 1 hour (Solution A). To a solution of (2S,4R)-1-allyloxycarbonyl-4-methoxy-2-(2-methyl-3-oxo-1-butenyl)pyrrolidine (2.70 g) and N-ethylpiperidine (1.48 ml) in dichloromethane (50 ml) was added trimethylsilyl trifluoromethanesulfonate (2.93 ml) at −20° C. and the resulting mixture was stirred at 0° C. for 1 hour. To this mixture was added dropwise the above obtained Solution A at 0° C. and the resulting mixture was stirred for another 1 hour at 0° C. The reaction mixture was taken up into a mixture of ethyl acetate (300 ml) and water (300 ml) and the mixture was stirred at ambient temperature for 2 hours. After adjusting pH to around 6.5 with aqueous sodium hydrogen carbonate, the organic layer was separated, washed with brine, dried over magnesium sulfate and evaporated in vacuo. The residue was chromatographed on silica gel (120 ml) eluting with a mixture of n-hexane and ethyl acetate (1:1 V/V) to give (3S,4R)-4-[4-{(2S,4R)-1-allyloxycarbonyl-4-methoxypyrrolidin-2-yl}-3-methyl-2-oxo-3-butenyl]-3-[(1R)-1-t-butyldimethylsilyloxyethyl]-2-oxoazetidine (3.24 g).

IR (CH$_2$Cl$_2$): 3420, 1760, 1700, 1670 cm$^{-1}$

NMR (CDCl$_3$, δ): 0.10 (6H, s), 0.88 (9H, s), 1.21 (3H, d, J=6 Hz), 1.85 (3H, d, J=1 Hz), 1.48–2.52 (2H, m), 2.60–3.15 (3H, m), 3.33 (3H, s), 3.15–4.35 (5H, m), 4.40–4.95 (3H, m), 4.95–5.50 (2H, m), 5.50–6.25 (1H, m), 6.02 (1H, br. s), 6.41 (1H, dq, J=1, 8 Hz)

Preparation 45-(2)

To a solution of (3R,4R)-4-acetoxy-3-[(1R)-1-t-butyldimethylsilyloxyethyl]-2-oxoazetidine (1.48 g) and N-ethylpiperidine (0.69 ml) in dichloromethane (10 ml) was added trimethylsilyl trifluoromethanesulfonate (1.0 ml) at −20° C., and the resulting mixture was stirred at 0° C. for 1 hour (Solution A). To a solution of (2S,4R)-1-allyloxycarbonyl-4-(methylcarbamoyloxy)-2-(2-methyl-3-oxo-1-butenyl)pyrrolidine (1.60 g) and N-ethylpiperidine (1.50 ml) in dichloromethane (20 ml) was added trimethylsilyl trifluoromethanesulfonate (2.5 ml) at −20° C. and the resulting mixture was stirred at 0° C. for 1 hour. To this mixture was added dropwise the above obtained Solution A at 0° C. and the resulting mixture was stirred for another 1 hour at 0° C. The resulting mixture was taken up into a mixture of ethyl acetate (150 ml) and water (150 ml) and the mixture was stirred at ambient temperature for 2 hours. After adjusting pH to around 6.5 with aqueous sodium hydrogen carbonate, the organic layer was separated, washed with brine, dried over magnesium sulfate and evaporated in vacuo. The residue was chromatographed on silica gel (75 ml) eluting with a mixture of n-hexane and ethyl acetate (7:3–0:10 V/V) to give (3S,4R)-4-[4-{(2S,4R)-1-allyloxycarbonyl-4-(methylcarbamoyloxy)pyrrolidin-2-yl}-3-methyl-2-oxo-3-butenyl]-3-[(1R)-1-t-butyldimethylsilyloxyethyl]-2-oxoazetidine (2.00 g).

IR (CH$_2$Cl$_2$): 3450, 3410, 1760, 1720, 1700, 1670 cm$^{-1}$

NMR (CDCl$_3$, δ): 0.10 (6H, s), 0.91 (9H, s), 1.23 (3H, d, J=6 Hz), 1.87 (3H, s), 1.60–2.58 (2H, m), 2.68–3.31 (6H, m), 3.45–4.33 (4H, m), 4.42–4.95 (4H, m), 5.00–5.43 (3H, m), 6.09 (1H, br. s), 5.60–6.20 (1H, m), 6.30–6.52 (1H, m)

Preparation 45-(3)

(3S,4R)-4-[4-{(2S,4R)-1-Allyloxycarbonyl-4-dimethyl-carbamoyloxy)pyrrolidin-2-yl}-3-methyl-2-oxo-3-butenyl]-3-1[(1R)-1-t-butyldimethylsilyloxyethyl]-2-oxoazetidine was obtained in 81.9% yield in substantially the same manner as that of Preparation 45-(1).

IR (Neat): 3300, 1760, 1700 cm$^{-1}$

NMR (CDCl$_3$, δ): 0.07 (6H, s), 0.87 (9H, s), 1.21 (3H, d, J=6 Hz), 1.85 (3H, s), 1.45–2.56 (2H, m), 2.90 (6H, s), 2.56–3.40 (3H, m), 3.50–4.33 (4H, m), 4.40–4.97 (3H, m), 5.00–5.40 (3H, m), 6.02 (1H, br. s), 5.50–6.15 (1H, m), 6.40 (1H, d, J=8 Hz)

Preparation 45-(4)

(3S,4R)-4-[4-{(2S,4S)-1-Allyloxycarbonyl-4-(N-allyloxycarbonyl-N-methylamino)pyrrolidin-2-yl}-3-methyl-2-oxo-3-butenyl]-3-[1R)-1-t-butyldimethylsilyloxyethyl]-2-oxoazetidine was obtained in 64.0% yield in substantially the same manner as that of Preparation 45-(1).

IR (CH$_2$Cl$_2$): 3410, 1760, 1690 cm$^{-1}$

NMR (CDCl$_3$, δ): 0.10 (6H, s), 0.89 (9H, s), 1.22 (3H, d, J=6 Hz), 1.83 (3H, d, J=1 Hz), 1.60–2.56 (2H, m), 2.88 (3H, s), 2.56–3.15 (3H, m), 3.15–4.31 (4H, m), 4.35–4.85 (6H, m), 4.95–5.40 (4H, m), 5.50–6.20 (2H, m), 6.10 (1H, br. s), 6.25–6.55 (1H, m)

Preparation 45-(5)

(3S,4R)-4-[4-{(2S)-1-Allyloxycarbonyl-4-fluoropyrrolidin-2-yl}-3-methyl-2-oxo-3-butenyl]-3-[1R)-1-t-butyldimethylsilyloxyethyl]-2-oxoazetidine was obtained in 67.4% yield in substantially the same manner as that of Preparation 45-(1).

IR (CHCl$_3$): 3430, 1755, 1700, 1670 cm$^{-1}$

NMR (CDCl$_3$, δ): 0.08 (6H, s), 0.88 (9H, s), 1.20 (3H, d, J=7 Hz), 1.50–2.40 (2H, m), 1.85 (3H, s), 2.50–6.15 (12H, m), 4.57 (2H, d, J=6 Hz), 6.02 (1H, br. s), 6.58 (1H, d, J=9 Hz) $^{19}$F NMR (CDCl$_3$, CF$_3$CO$_2$H): −91.56 (m)

Preparation 45-(6)

(3S,4R)-4-[4-{(2R)-1-Allyloxycarbonylpyrrolidin-2-yl}-3-methyl-2-oxo-3-butenyl]-3-[(1R)-1-t-butyldimethylsilyloxyethyl]-2-oxoazetidine was obtained in 54.8% yield in substantially the same manner as that of Preparation 45-(1).

NMR (CDCl$_3$, δ): 0.09 (6H, s), 0.87 (9H, s), 1.21 (3H, d, J=6 Hz), 1.84 (3H, d, J=1 Hz), 1.50–2.43 (4H, m), 2.62–3.23 (3H, m), 3.35–4.30 (4H, m), 4.40–4.85 (3H, m), 5.05–5.44 (2H, m), 5.57–6.90 (2H, m), 6.40 (1H, dq, J=1, 8 Hz)

Preparation 45-(7)

To a solution of 1-allyloxycarbonyl-2-(2-methyl-3-oxy-1-butenyl)piperidine (9.9 g), (3R,4R)-4-acetoxy-3-[1R)-1-t-butyldimethylsilyloxyethyl]-2-oxoazetidine (17.0 g) and triethylamine (16.5 ml) in dichloromethane (100 ml) was added trimethylsilyl trifluoromethanesulfonate (28.6 ml) at −15° C. After stirring at 0° C. for 2 hours, the reaction mixture was taken up into a mixture of ethyl acetate (200 ml) and water (200 ml). The mixture was stirred for 2 hours at ambient temperature. After addition of sodium chloride (40 g), the organic layer was separated, washed with saturated sodium hydrogen carbonate and brine, dried over magnesium sulfate and evaporated. The residue was chromatographed on silica gel (300 ml) eluting with a mixture of n-hexane and ethyl acetate (5:1–7:3, V/V) to give (3S,4R)-4-[4-(1-allyloxycarbonyl-piperidin-2-yl)-3-methyl-2-oxo-3-butenyl]-3-[(1R)-1-t-butyldimethylsilyloxyethyl]-2-oxoazetidine (13.48 g).

IR (CHCl$_3$): 3430, 1760, 1700, 1680 cm$^{-1}$

NMR (CDCl$_3$, δ): 0.12 (6H, s), 0.91 (9H, s), 1.25 (3H, d, J=6 Hz), 1.90 (3H, br. s), 2.8–3.1 (3H, m), 3.9–4.3 (4H, m), 4.58 (2H, br. d, J=6 Hz), 5.1–5.4 (3H, m), 5.7–6.1 (1H, m), 6.10 (1H, br. s), 6.75 (1H, br. d, J=9 Hz)

Preparation 45-(8)

(3S,4R)-4-[4-{(2S)-1-(N-Allyloxycarbonyl-N-methylaminoacetyl)pyrrolidin-2-yl}-3-methyl-2-oxo-3-butenyl]-3-[(1R)-1-t-butyldimethylsilyloxyethyl]-2-oxoazetidine was obtained in 73.4% yield in substantially the same manner as that of Preparation 45-1).

IR (CHCl$_3$): 3430, 1760, 1700, 1665 cm$^{-1}$

NMR (CDCl$_3$, δ): 0.08 (6H, s), 0.89 (9H, s), 1.13 (3H, d, J=6 Hz), 1.80 (3H, br. s), 2.87 (3H, br. s), 2.6–3.1 (3H, m), 3.4–4.2 (6H, m), 4.4–4.9 (3H, m), 5.0–5.4 (2H, m), 5.6–6.1 (1H, m), 6.4–6.8 (1H, m)

Preparation 45-(9)

(3S,4R)-4-[4-{(1-Allyloxycarbonylazetidin-3-yl)-3-methyl-2-oxo-3-butenyl]-3-[(1R)-1-t-butyldimethylsilyloxyethyl]-2-oxoazetidine was obtained in 37.2% yield in substantially the same manner as that of Preparation 45-(1).

IR (Nujol): 1760, 1706, 1675 cm$^{-1}$

NMR (CDCl$_3$, δ): 0.07 (6H, s), 0.87 (9H, s), 1.22 (3H, d, J=6 Hz), 1.73 (3H, s), 2.64–3.15 (3H, m), 3.40–4.62 (9H, m), 5.05–5.40 (2H, m), 5.60–6.18 (2H, m), 6.60–6.88 (1H, d, J=7 Hz)

Preparation 45-(10)

(3S,4R)-4-[4-(1-Allyloxycarbonyl-5-methoxymethylpyrrolidin-2-yl)-3-methyl-2-oxo-3-butenyl]-3-[(1R)-1-t-butyldimethylsilyloxyethyl]-2-oxoazetidine was obtained in 68.4% yield in substantially the same manner as that of Preparation 45-(1).

IR (CHCl$_3$): 3420, 1750, 1685, 1660 cm$^{-1}$

NMR (CDCl$_3$, δ): 0.07 (6H, s), 0.88 (9H, s), 1.22 (3H, d, J=6 Hz), 1.50–2.40 (4H, m), 1.83 (3H, s), 2.65–3.20 (3H, m), 3.36 (3H, s), 3.50 (2H, d, J=4 Hz), 3.70–4.50 (3H, m), 4.50–5.45 (3H, m), 5.60–6.30 (2H, m), 6.53 (1H, d, J=8 Hz)

Preparation 45-(11)

(3S,4R)-4-[4-(1-Allyloxycarbonyl-5-t-butyldimethylsilyloxymethylpyrrolidin-2-yl)-3-methyl-2-oxo-3-butenyl]-3-[(1R)-1-t-butyldimethylsilyloxyethyl]-2-oxoazetidine was obtained in 66.9% yield in substantially the same manner as that of Preparation 45-(1).

IR (CHCl$_3$): 3430, 1760, 1700, 1675 cm$^{-1}$

NMR (CDCl$_3$, δ): 0.08 (12H, s), 0.90 (18H, s), 1.22 (3H, d, J=6 Hz), 1.83 (3H, s), 1.50–2.40 (4H, m), 2.70–3.30 (3H, m), 3.60–4.30 (6H, m), 4.46–4.80 (2H, m), 5.06–5.40 (2H, m), 5.50–6.35 (1H, m), 6.10 (1H, br. s), 6.45 (1H, d, J=8 Hz)

Preparation 45-(12)

(3S,4R)-4-[4-(1-Allyloxycarbonylpyrrolidin-3-yl)-3-methyl-2-oxo-3-butenyl]-3-[(1R)-1-t-butyldimethylsilyloxyethyl]-2-oxoazetidine was obtained in 71.5% yield in substantially the same manner as that of Preparation 45-(1).

IR (CH$_2$Cl$_2$): 1760–1750, 1695–1685 cm$^{-1}$

NMR (CDCl$_3$, δ): 0.08 (6H, s), 0.87 (9H, s), 1.20 (3H, d, J=6 Hz), 1.83 (3H, s), 4.5–4.7 (2H, m), 5.1–5.4 (2H, m), 5.7–6.1 (1H, m), 6.12 (1H, br s), 6.43 (1H, br. d, J=8 Hz)

Preparation 45-(13)

(3S,4R)-4-[4-{(2S)-5-Allyloxycarbonylimino-1-methylpyrrolidin-2-yl}-3-methyl-2-oxo-3-butenyl]-3-[(1R)-1-t-butyldimethylsilyloxyethyl]-2-oxoazetidine was obtained in 62.0% yield in substantially the same manner as that of Preparation 45-(1).

IR (CH$_2$Cl$_2$): 3400, 1760, 1735, 1685 cm$^{-1}$

NMR (CDCl$_3$, δ): 0.09 (6H, s), 0.89 (9H, s), 1.21 (3H, d, J=7 Hz), 1.88 (3H, d, J=1 Hz), 2.02 (3H, s), 2.89 (3H, s), 3.8–4.3 (2H, m), 4.5–4.7 (2H, m), 5.0–5.4 (2H, m), 5.7–6.4 (3H, m)

Preparation 45-(14)

(3S,4R)-4-[4-{(3R)-4-Allyloxycarbonylmorpholin-3-yl}-3-methyl-2-oxo-3-butenyl]-3-[(1R)-1-t-butyldimethylsilyloxyethyl]-2-oxoazetidine was obtained in 91.2% yield in substantially the same manner as that of Preparation 45-(1).

IR (CHCl₃): 3430, 1755, 1690, 1675 cm⁻¹

NMR (CDCl₃, δ): 0.07 (6H, s), 0.90 (9H, s), 1.23 (3H, d, J=6 Hz), 1.90 (3H, d, J=1 Hz), 2.6–4.4 (11H, m), 4.4–4.7 (2H, m), 4.7–5.0 (1H, m), 5.0–5.4 (2H, m), 5.6–6.2 (2H, m), 6.90 (1H, dq, J=9 Hz, 1 Hz)

Preparation 46-(1)

(3S, 4R)-4-[4-{(2S)-1-Allyloxycarbonyl-4-fluoropyrrolidin-2-yl}-3-methyl-2-oxo-3-butenyl]-3-[(1R)-1-hydroxyethyl]-2-oxoazetidine was obtained quantitatively in substantially the same manner as that of Preparation 15.

IR (CHCl₃): 3450, 3420, 1760, 1700, 1665 cm⁻¹

NMR (CDCl₃, δ): 1.30 (3H, d, J=7 Hz), 1.85 (3H, s), 1.95–2.35 (2H, m), 2.50–6.15 (13H, m), 4.58 (2H, d, J=5 Hz), 6.58 (1H, br s), 6.63 (1H, d, J=9 Hz) ¹⁹F NMR (CDCl₃, CF₃CO₂H): −91.56 (m)

Preparation 46-(2)

(3S,4R)-4-[4-{(2R)-1-Allyloxycarbonylpyrrolidin-2-yl}-3-methyl-2-oxo-3-butenyl]-3-[(1R)-1-hydroxyethyl]-2-oxoazetidine was obtained quantitatively in substantially the same manner as that of Preparation 15.

NMR (CDCl₃, δ): 1.32 (3H, d, J=6 Hz), 1.85 (3H, s), 1.5–2.4 (4H, m), 2.7–2.9 (1H, m), 2.9–3.2 (2H, m), 3.4–3.7 (2H, m), 3.7–4.0 (1H, m), 4.0–4.3 (1H, m), 4.4–4.8 (3H, m), 5.1–5.4 (2H, m), 5.6–6.2 (1H, m), 6.50 (1H, br. d, J=8 Hz)

Preparation 46-(3)

(3S,4P)-4-[4-(1-Allyloxycarbonyl-5-methoxymethylpyrrolidin-2-yl)-3-methyl-2-oxo-3-butenyl]-3-[(1R)-1-hydroxyethyl]-2-oxoazetidine was obtained in 99.3% yield in substantially the same manner as that of Preparation 15.

IR (CHCl₃) 3450, 3425, 1760, 1690, 1670 cm⁻¹

NMR (CDCl₃, δ): 1.30 (3H, d, J=7 Hz), 1.83 (3H, s), 1.50–2.40 (4H, m), 2.70–3.30 (3H, m), 3.36 (3H, s), 3.50 (2H, d, J=4 Hz), 3.70–4.40 (3H, m), 4.40–4.80 (3H, m), 5.05–5.40 (2H, m), 5.65–6.15 (1H, m), 6.85 (1H, br. s), 6.57 (1H, d, J=7 Hz)

Preparation 46-(4)

To a solution of (3S,4R)-4-[(E)-4-{(2S)-1-allyloxycarbonylpyrrolidin-2-yl}-3-methyl-2-oxo-3-butenyl]-3-(1R)-1-t-butyldimethylsilyloxyethyl]-2-oxoazetidine (33.90 g) in acetonitrile (68 ml) was added boron trifluoride etherate (19.74 ml) at 5–10° C. After stirring at 0° C. for 30 minutes, the reaction mixture was taken up into a mixture of ethyl acetate (170 ml), water (140 ml) and sodium bicarbonate (13.48 g). After stirring for 30 minutes, the organic layer was separated. The aqueous layer was extracted with ethyl acetate (70 ml). The combined organic portion was washed with brine (100 ml) and dried over magnesium sulfate. The solvent was removed in vacuo to give (3S,4R)-4-[(E)-4-{(2S)-1-allyloxycarbonylpyrrolidin-2-yl}-3-methyl-2-oxo-3-butenyl]-3-[(1R)-1-hydroxyethyl]-2-oxoazetidine.

IR (CHCl₃): 3420, 1755, 1680, 1660 cm⁻¹

NMR (CDCl₃, δ): 1.30 (3H, d, J=6 Hz), 1.5–2.3 (4H, m), 1.83 (3H, d, J=1 Hz), 2.82 (1H, dd, J=3, 7.5 Hz), 2.9–3.2 (2H, m), 3.2–3.7 (3H, m), 3.7–4.3 (2H, m), 4.4–4.8 (3H, m), 5.0–5.4 (2H, m), 5.5–6.1 (1H, m), 6.50 (1H, dq, J=1, 8 Hz), 6.53 (1H, br. s)

Preparation 46-(5)

(3S,4R)-4-[4-{(3R)-4-Allyloxycarbonylmorpholin-3-yl}-3-methyl-2-oxo-3-butenyl]-3-[(1R)-1-hydroxyethyl]-2-oxoazetidine was obtained quantitatively in substantially the same manner as that of Preparation 46(4).

IR (CHCl₃): 3500, 3420, 1760, 1690, 1670 cm⁻¹

NMR (CDCl₃, δ): 1.33 (3H, d, J=6 Hz), 1.90 (3H, d, J=1 Hz), 2.6–4.4 (11H, m), 4.4–4.7 (2H, m), 4.7–5.0 (11H, m), 5.1–5.4 (2H, m), 5.6–6.2 (1H, m), 6.35 (1H, br s), 6.93 (1H, dq, J=9 Hz, 1 Hz)

Preparation 47-(1)

Allyl 2-[(3S,4R)-4-[4-{(2S,4R)-1-allyloxycarbonyl-4-methoxypyrrolidin-2-yl}-3-methyl-2-oxo-3-butenyl]-3-{(1R)-1-t-butyldimethylsilyloxyethyl)-2-oxoazetidin-1-yl]-2 triphenylphosphoranylideneacetate was obtained in 44.0% yield in substantially the same manner as that of Preparation 3-(1).

IR (CH₂Cl₂): 1740, 1700 cm⁻¹

NMR (CDCl₃, δ): 0.80 (9H, s), 3.30 (3H, s), 7.10–8.00 (15H, m)

Preparation 47-(2)

Allyl 2-[(3S,4R)-4-[4-{(2S,4R)-1-allyloxycarbonyl-4--(dimethylcarbamoyloxy)pyrrolidin-2-yl)-3-methyl-2-oxo-3-butenyl]-3-{(1R)-1-t-butyldimethylsilyloxyethyl)-2-oxoazetidin-1-yl]-2-triphenylphosphoranylideneacetate was obtained in 56.5% yield in substantially the same manner as that of Preparation 3(1).

IR (CH₂Cl₂): 1740, 1700 cm⁻¹

NMR (CDCl₃, δ): 2.89 (6H, s), 7.20–7.95 (15H, m)

Preparation 48-(1)

To a solution of (3S,4R)-4-[4-{(2S,4R)-1-allyloxycarbonyl-4-(dimethylcarbamoyloxy)pyrrolidin-2-yl)-3-methyl-2-oxo-3-butenyl]-3-[(1R)-1-t-butyldimethylsilyloxyethyl]-2-oxoazetidine (0.33 g) and triethylamine (0.17 ml) in dichloromethane (10 ml) was added allyl oxalyl chloride (0.13 g) at −20° C. and the resulting mixture was stirred for 30 minutes at −20° C. The reaction mixture was taken up into a mixture of water (50 ml) and ethyl acetate (50 ml). The organic layer was separated, washed in turn with water, aqueous sodium hydrogen carbonate and brine, and dried over magnesium sulfate. Evaporation of the solvent gave allyl 2-[(3S,4R)-4-[4-{(2S,4R)-1-allyloxycarbonyl-4-(dimethylcarbamoyloxy)pyrrolidin-2-yl}-3-methyl-2-oxo-3-butenyl]- 3-{(1R)-1-t-butyldimethylsilyloxyethyl)-2-oxoazetidin-1-yl]glyoxylate (0.26 g).

IR (CH₂Cl₂): 1800, 1750, 1700 cm⁻¹

NMR (CDCl₃, δ): 0.02 (3H, s), 0.08 (3H, s), 0.84 (9H, s), 1.22 (3H, d, J=6 Hz), 1.84 (3H, d, J=1 Hz), 1.70–2.60 (2H, m), 2.89 (6H, s), 2.73–3.24 (2H, m), 3.50–3.82 (3H, m), 4.18–4.40 (1H, m), 4.45–4.95 (6H, m), 5.00–5.50 (5H, m), 5.60–6.17 (2H, m), 6.35–6.58 (1H, m)

Preparation 48-(2)

Allyl 2-[(3S,4R)-4-[4-(1-allyloxycarbonylpyrrolidin-3-yl)-3-methyl-2-oxo-3-butenyl]-3-{(1R)-1-t-butyldimethylsilyloxyethyl) -2-oxoazetidin-1-yl]glyoxylate was obtained in 97.7% yield in substantially the same manner as that of Preparation 48-(1).

IR (Neat): 1805–1795, 1755–1745, 1710–1665 cm⁻¹

NMR (CDCl₃, δ): 0.03 (3H, s), 0.06 (3H, s), 0.85 (9H, s), 1.25 (3H, d, J=6 Hz), 1.83 (3H, s), 6.50 (1H, br. d, J=8 Hz)

Preparation 49

To a solution of (3S,4R)-4-[(E)-4-{(2S)-1-allyloxycarbonylpyrrolidin-2-yl}-3-methyl-2-oxo-3-butenyl]-3-[(1R)-1-hydroxyethyl]-2-oxoazetidine obtained in Preparation 46-(4) and pyridine (18.88 ml) in dichloromethane (250 ml) was added trimethylsilyl chloride (9.26 ml) at −70° C. The reaction mixture was stirred at −50° C. for 10 minutes. To the reaction mixture was added allyl oxalyl chloride (12.54 ml) at −50° C. and the resultant mixture was stirred at −20° C. for 30 minutes. The reaction mixture was taken up into a mixture of ethyl acetate (150 ml), hexane (300 ml) and water (250 ml). The organic layer was separated, washed in turn with water, aqueous sodium hydrogen carbonate and brine, and dried over magnesium sulfate. Removal of the solvent gave allyl 2-[(3S,4R)-4-[(E)-4-[(2S)-1-allyloxycarbonylpyrrolidin-2-yl)-3-methyl-2-oxo-3-butenyl]-3-{(1R)-1-trimethylsilyloxyethyl)-2-oxoazetidin-1-yl]glyoxylate.

IR (CHCl$_3$): 1800, 1750, 1680

NMR (CDCl$_3$, δ): 0.10 (9H, s), 1.25 (3H, d, J=6 Hz), 1.6–2.3 (4H, m), 1.9 (3H, d, J=1 Hz), 1.8–2.2 (2H, m), 3.4–3.8 (3H, m), 4.2–4.4 (1H, m), 4.4–4.9 (6H, m), 5.0–5.6 (4H, m), 5.6–6.1 (2H, m), 6.3–6.7 (1H, m)

Preparation 50

To a solution of (3S,4R)-3-[(1R)-1-t-butyldimethylsilyloxyethyl]-4-carboxymethyl-2-oxoazetidine (302.6 mg) in dimethylformamide (10 ml) was added potassium carbonate (160 mg) at ° C. After 10 minutes, to the mixture was added dropwise methyl iodide (68.8 µl). After stirring at 0° C. for 1.5 hours, the reaction mixture was poured into a mixture of ethyl acetate (100 ml) and water (30 ml). The organic layer was separated, washed with brine and dried over magnesium sulfate. Evaporation of the solvent gave (3S,4R)-3-[(1R)-1-t-butyldimethylsilyloxyethyl]-4-methoxycarbonylmethyl-2-oxoazetidine (285.5 mg).

IR (Nujol): 1760–1740 cm$^{-1}$

NMR (CDCl$_3$, δ): 0.06 (6H, s), 0.87 (9H, s), 1.21 (3H, d, J=6 Hz), 2.50–2.90 (3H, m), 3.71 (3H, s), 3.84–4.32 (2H, m), 5.98–6.20 (1H, m)

Preparation 51

To a solution of methyl triphenylphosphonium bromide (690 mg) in tetrahydrofuran (2 ml) was added dropwise a solution of n-butyl lithium in n-hexane (1.59N, 1.21 ml) at room temperature and the mixture was stirred for one hour. The reaction mixture was added dropwise to a solution of (3S,4R)-3-[(1R)-1-t-butyldimethylsilyloxyethyl-4-methoxycarbonylmethyl-2-oxoazetidine (233 mg) in tetrahydrofuran (8 ml) at −78° C. The reaction mixture was allowed to warm to room temperature and stirred for one hour, and then poured into a mixture of ethyl acetate (50 ml) and phosphate buffer (20 ml). The organic layer was separated, washed with brine and dried over magnesium sulfate. Evaporation of the solvent gave a residue, which was chromatographed on silica gel (20 ml) eluting with ethyl acetate to give (3S,4R)-3-[(1R)-1-t-butyldimethylsilyloxyethyl]-4-(3-triphenylphosphoranylidene-2-oxopropyl)-2-oxoazetidine (157 mg).

IR (Nujol): 1760–1745 cm$^{-1}$

NMR (CDCl$_3$, δ): 0.06 (6H, s), 0.87 (9H, s), 1.23 (3H, d, J=6 Hz), 2.37–2.94 (3H, m), 3.84–4.33 (2H, m), 6.35–6.48 (1H, m), 7.30–7.80 (16H, m)

Preparation 52

A solution of (3S,4R)-3-[(1R)-1-t-butyldimethylsilyloxyethyl]-4-(3-triphenylphosphoranylidene-2-oxopropyl)-2-oxoazetidine (572 mg) and (2S)-1-allyloxycarbonyl-2-formylpyrrolidine (201.5 mg) in toluene (5 ml) was heated to reflux for three hours. Evaporation of the solvent gave a residue, which was taken up into ethyl acetate. The resultant precipitate was filtered off and washed with ethyl acetate. The filtrate and the washings were combined and evaporated in vacuo. The residue was chromatographed on silica gel (50 ml) eluting with a mixture of n-hexane and ethyl acetate (2:1–1:-1–1:3 V/V) to give (3S,4R)-4-[(E)-4-{(2S)-1-allyloxycarbonylpyrrolidin-2-yl}-2-oxo-3-butenyl]-3-[(1R)-1-t-butyldimethylsilyloxyethyl]-2-oxoazetidine (297.7 mg).

IR (Nujol) : 1760–1740, 1710–1670 cm$^{-1}$

NMR (CDCl$_3$, δ): 0.08 (6H, s), 0.87 (9H, s), 1.23 (3H, d, J=6 Hz), 1.64–2.20 (4H, m), 2.65–2.80 (3H, m), 3.38–3.60 (2H, m), 3.82–4.30 (2H, m), 4.40–4.64 (3H, m), 5.06–5.41 (2H, m), 5.64–6.23 (3H, m), 6.76 (1H, dd, J=15, 9 Hz)

Preparation 53

(3S,4R)-4-[(E)-4-{(2S)-1-Allyloxycarbonylpyrrolidin-2-yl}-2-oxo-3-butenyl]-3-[(1R)-1-hydroxyethyl]-2-oxo-azetidine (1.83 g) was obtained from (3S,4R)-4-[(E)-4-{(2S)-1-allyloxycarbonylpyrrolidin-2-yl}-2-oxo-3-buten-yl]-3-[(1R)-1-t-butyldimethylsilyloxyethyl]-2-oxoazetidine (4.5 g) in substantially the same manner as that of Preparation 46-(4).

IR (Nujol): 3450–3100, 1760–1730, 1690–1670 cm$^{-1}$

NMR (CDCl$_3$, δ): 1.34 (3H, d, J=7 Hz), 1.51–2.30 (5H, m), 2.73–3.03 (3H, m), 3.39–3.60 (2H, m), 3.77–4.30 (2H, m), 4.40–4.64 (3H, m), 5.07–5.42 (2H, m), 5.60–6.30 (3H, m), 6.76 (1H, dd, J=15, 9 Hz)

Preparation 54

Allyl 2-[(3S,4R)-4-[(E)-4-{(2S)-1-allyloxycarbonylpyrrolidin-2-yl}-2-oxo-3-butenyl]-3-{(1R)-1-trimethylsilyloxyethyl)-2-oxoazetidin-1-yl]-glyoxylate (2.17 g) was obtained from (3S,4R)-4-[(E)-4-{(2S)-1-allyloxycarbonylpyrrolidin-2-yl)-2-oxo-butenyl[-3nyl]-3-[(1R)-1-hydroxyethyl]-2-oxoazetidine (1.82 g) in substantially the same manner as that of Preparation 49.

IR (Nujol): 1800, 1760–1740, 1710–1670 cm$^{-1}$

NMR (CDCl$_3$, δ) : 0.09 (9H, s), 1.23 (3H, d, J=6 Hz), 1.70–2.30 (4H, m), 2.76–3.60 (5H, m), 4.18–4.83 (6H, m), 5.03–5.50 (4H, m), 5.70–6.20 (4H, m), 6.76 (1H, dd, J=15, 9 Hz)

Preparation 55

To a suspension of (2S)-2-carboxypyrrolidine (40 g) in a mixture of water (200 ml) and tetrahydrofuran (200 ml) was added a solution of allyl chloroformate (44 ml) in tetrahydrofuran (40 ml) at ° C. while adjusting pH to around 9 with 4N aqueous sodium hydroxide. After stirring at ° C. for 1 hour at pH 9, the aqueous layer was saturated with sodium chloride, and the mixture was diluted with ethyl acetate (200 ml). The aqueous layer was separated and washed with ethyl acetate. After adjusting pH to around 2 with 6N hydrochloric acid, the mixture was extracted with two portions of ethyl acetate (200 ml×2). The combined extract was dried over magnesium sulfate and evaporated in vacuo to give (2S)-1-allyloxycarbonyl-2-carboxypyrrolidine (72.49 g).

IR (CH$_2$Cl$_2$): 3100, 1760, 1700 cm$^{-1}$

Preparation 56

To a solution of (2S)-1-allyloxycarbonyl-2-carboxypyrrolidine (72.4 g) in N,N-dimethylformamide (250 ml) were added potassium carbonate (57.6 g) and methyl iodide (43.2 ml) at ° C. with stirring. The resulting mixture was allowed to warm to ambient temperature and stirring was continued for additional 1 hour. The reaction mixture was taken up into a mixture of ethyl acetate (1.2 l) and water (0.6 l). The organic layer was separated, washed in turn with water (1l×3), brine (1l), dried over magnesium sulfate, and evaporated to give (2S)-1-allyloxycarbonyl-2-methoxycarbonylpyrrolidine (66.21 g).

IR (CHCl$_3$): 1740, 1690 cm$^{-1}$

NMR (CDCl$_3$, δ): 1.80–2.36 (4H, m), 3.45–3.75 (5H, m), 4.30–4.42 (1H, m), 4.53–4.62 (2H, m), 5.10–5.37 (2H, m), 5.85–5.97 (1H, m)

Preparation 57

To a solution of (2S)-1-allyloxycarbonyl-2-methoxycarbonylpyrrolidine (2.0 g) in ethanol (30 ml) was added sodium borohydride (1.06 g) at 20° C. and the resulting mixture was allowed to stir for 18 hours at 20°–25° C. The reaction mixture was taken up into a mixture of brine (100 ml) and ethyl acetate (100 ml). The organic layer was washed with brine, dried over magnesium sulfate and evaporated. The residue was chromatographed on silica gel (50 ml) eluting with a mixture of dichloromethane and acetone (20:1) to give (2S)-1-allyloxycarbonyl-2-hydroxymethylpyrrolidine (769.2 mg).

IR (Neat): 3400, 1670 cm$^{-1}$

NMR (CDCl$_3$, δ): 1.45–2.20 (4H, m), 3.20–3.80 (4H, m), 3.80–4.46 (2H, m), 4.50–4.75 (2H, m), 5.10–5.52 (2H, m), 5.70–6.20 (1H, m)

Preparation 58

To a suspension of sodium borohydride (5 g) in ethanol (50 ml) was added (2S,4R)-1-allyloxycarbonyl-2-methoxycarbonyl-4-hydroxypyrrolidine (10 g) in ethanol (10 ml) at 5° C. and the resulting mixture was stirred at 40° C. for 4 hours. After cooling to 0° C., the reaction mixture was added dropwise to cooled acetone (20 ml) at 10° C. The mixture was evaporated in vacuo and the residue was extracted with ethyl acetate (200 ml×2). The organic layer was washed with brine, dried over magnesium sulfate, evaporated and chromatographed on silica gel (120 ml) eluting with a mixture of n-hexane and ethyl acetate (1:1 V/V) to give (2S,4R)-1-allyloxycarbonyl-4-hydroxy-2-hydroxymethylpyrrolidine (4.45 g).

NMR (CDCl$_3$, δ): 1.40–2.25 (2H, m), 3.30–4.50 (8H, m), 4.57 (2H, m), 5.00–5.45 (2H, m), 5.60–6.15 (1H, m)

Preparation 59

To a solution of (2S,4R)-1-allyloxycarbonyl-4-hydroxy-2-hydroxymethylpyrrolidine (1.0 g) in dichloromethane (15 ml) were added triethylamine (0.7 ml), t-butyldimethylsilyl chloride (0.57 g) and 1,8-diazabicyclo[5.4.0]-7-undecene (0.15 g). The resulting mixture was allowed to stand at ambient temperature for 5 hours. The mixture was diluted with ethyl acetate (150 ml), washed in turn with aqueous ammonium chloride and brine, dried over magnesium sulfate and evaporated. The residue was chromatographed on silica gel (40 ml) eluting with a mixture of n-hexane and ethyl acetate (3:1 V/V) to give (2S,4R)-1-allyloxycarbonyl-2-t-butyldimethylsilyloxymethyl-4-hydroxypyrrolidine (0.62 g).

NMR (CDCl$_3$, δ): 0.0 (6H, s), 0.85 (9H, s), 1.65–2.40 (2H, m), 3.30–4.25 (4H, m), 4.30–4.65 (2H, m), 5.00–5.40 (2H, m), 5.65–6.15 (1H, m)

Preparation 60

To a solution of oxalyl chloride (0.18 ml) in dichloromethane (10 ml) was added dropwise a solution of dimethyl sulfoxide (0.3 ml) in dichloromethane (2 ml) at −60° C. After stirring at −70° C. for 30 minutes, to the mixture was added dropwise a solution of (2S,4R)-1-allyloxycarbonyl-2-t butyldimethylsilyloxymethyl-4-hydroxypyrrolidine (0.6 g) in dichloromethane (5 ml) at −60° C. After stirring at −70° C. for 30 minutes, to the mixture was added dropwise triethylamine (1.3 ml) and the resulting mixture was allowed to warm to ° C. and diluted with ethyl acetate (150 ml) and brine. After adjusting pH to around 3 with 10% hydrochloric acid, the organic layer was separated, washed with brine, dried over magnesium sulfate and evaporated. The residue was chromatographed on silica gel (50 ml) eluting with 15% ethyl acetate in hexane to give (2S)-1-allyloxycarbonyl-2-t-butyldimethylsilyloxymethyl-4-oxo-pyrrolidine (0.54 g).

IR (Neat): 1763, 1705 cm$^{-1}$

NMR (CDCl$_3$, δ): 0.0 (6H, s), 0.83 (9H, s), 2.20–2.87 (2H, m), 3.40–4.50 (4H, m), 4.50–4.70 (2H, m), 5.05–5.40 (2H, m), 5.60–6.15.(1H, m)

Preparation 61

To a suspension of xethyl triphenylphosphonium bromide (7.29 g) in tetrahydrofuran (20 ml) was added a 0.5M solution of potassium t-butoxide (40.8 ml) at ° C. After stirring for 2 hours at 0° C., to this mixture was added a solution of (2S)-1-allyloxycarbonyl-2-(t-butyldimethylsilyloxymethyl)-4-oxopyrrolidine (3.20 g) in tetrahydrofuran (10 ml) at 10° C. After stirring at ambient temperature for 10 minutes, the reaction mixture was diluted with water (150 ml) and ethyl acetate (150 ml). The organic layer was separated, washed with brine, dried over magnesium sulfate and evaporated. The residue was chromatographed on silica gel (50 ml) eluting with a mixture of n-hexane and ethyl acetate (1:9–1:5 V/V) to give (2S)-1-allyloxycarbonyl-2-(t-butyldimethylsilyloxymethyl)-4-methylenepyrrolidine (2.89 g).

IR (CH$_2$Cl$_2$): 1690 cm$^{-1}$

NMR (CDCl$_3$, δ): 0.05 (6H, s), 0.89 (9H, s), 2.43–2.73 (2H, m), 3.30–4.25 (5H, m),
4.40–4.64 (2H, m), 4.80–5.05 (2H, m),
5.05–5.42 (2H, m), 5.70–6.16 (1H, m)

Preparation 62

To a solution of (2S)-1-allyloxycarbonyl-2-(t-butyldimethylsilyloxymethyl)-4-methylenepyrrolidine (2.88 g) in ethyl acetate (100 ml) was added 6N hydrochloric acid (3.0 ml) at ambient temperature. After stirring for 1 hour at ambient temperature, to the mixture were added potassium carbonate (2.54 g) and brine (30 ml) with stirring. The organic layer was separated, washed in turn with aqueous sodium hydrogen carbonate and brine, dried over magnesium sulfate and evaporated. The residue was chromatographed on silica gel (40 ml) eluting with a mixture of n-hexane and ethyl acetate (3:1 V/V) to give (2S)-1-allyloxycarbonyl-2-hydroxymethyl-4-methylenepyrrolidine (1.78 g).

IR (CH$_2$Cl$_2$): 3400, 1680 cm$^{-1}$

NMR (CDCl$_3$, δ): 2.15–2.90 (2H, m), 2.68 (1H, br. s), 3.61 (2H, d, J=5 Hz), 3.90–4.34 (3H, m), 4.45–4.70 (2H, m), 4.86–5.06 (2H, m), 06–5.41 (2H, m), 5.68–6.16 (1H, m)

Preparation 63

(2S)-1-Allyloxyoarbonyl-2-(2-methyl-3-oxobutenyl)-4-methylenepyrrolidine was obtained in 84.0% yield in substantially the same manner as that of Preparation 1-(1).

IR (Film): 1700 cm$^{-1}$

NMR (CDCl$_3$, δ): 1.89 (3H, d, J=1 Hz), 2.29 (3H, s), 2.11–3.15 (2H, m), 3.98–4.21 (2H, m), 4.46–4.67 (2H, m), 4.67–5.40 (5H, m), 5.65–6.11 (1H, m), 6.37 (1H, dq, J=1,8 Hz)

Preparation 64

(3S,4R)-4-[4-{(2S)-1-Allyloxycarbonyl-4-methylenepyrrolidin-2-yl}-3-methyl-2-oxo-3-butenyl]-3-[(1R)-1-t-butyldimethylsilyloxyethyl]-2-oxoazetidine was obtained in 78.0% yield in substantially the same manner as that of Preparation 2-(1).

IR (CH$_2$Cl$_2$): 3420, 1760, 1700 cm$^{-1}$

NMR (CDCl$_3$, δ): 0.09 (6H, s), 0.89 (9H, s), 1.23 (3H, d, J=6 Hz), 1.89 (3H, d, J=1 Hz), 2.05–2.50 (1H, m), 2.53–3.28 (4H, m), 3.84–4.33 (4H, m), 4.40–4.64 (2H, m), 4.66–5.45 (5H, m), 5.60–6.13 (1H, m), 6.00 (1H, br s), 6.36 (1H, dq, J=1,8 Hz)

Preparation 65

To a solution of (2S,4R)-1-allyloxycarbonyl-4-hydroxy-2-(2-methyl-3-oxo-1-butenyl)pyrrolidine (0.33 g), triphenylphosphine (0.52 g) and benzoic acid (0.24 g) in tetrahydrofuran (4 ml) was added diethyl azodicarboxylate (0.31 ml) at ambient temperature. After stirring at ambient temperature for 1 hour, the solution was evaporated. To the residue was added a mixture of n-hexane and ethyl acetate (2:1 V/V), and precipitated triphenylphosphine oxide was filtered off. The filtrate was evaporated, and the residue was chromatographed on silica gel (80 ml) eluting with a mixture of n-hexane and ethyl acetate (8:2–7:3 V/V) to give (2S,4S)-1-allyloxycarbonyl-4-benzoyloxy-2-(2-methyl-3-oxo-1-butenyl)pyrrolidine (0.42 g).

NMR (CDCl$_3$, δ): 1.83 (3H, s), 2.18 (3H, s), 3.84 (2H, d, J=3 Hz), 4.59 (2H, d, J=4 Hz), 4.73–5.00 (1H, m), 5.02–5.39 (2H, m), 5.47–5.65 (1H, m), 6.56–6.78 (1H, m), 7.16–7.70 (5H, m),

IR (CH$_2$Cl$_2$): 1720, 1700, 1670 cm$^{-1}$

Preparation 66

To a solution of (2S,4S)-1-allyloxycarbonyl-4-benzoyloxy-2-(2-methyl-3-oxo-1-butenyl)pyrrolidine (0.23 g) in methanol (5 ml) was added 28% solution of sodium methoxide in methanol (0.13 ml) at ° C. and the resulting mixture was stirred at the same temperature for 1 hour. To this solution was added acetic acid (0.04 ml), and the mixture was poured into a mixture of brine and ethyl acetate. The organic layer was separated, washed three times with brine, dried over magnesium sulfate and evaporated. The residue was chromatographed on silica gel (20 ml) eluting with a mixture of n-hexane and ethyl acetate (1:1 V/V) to give (2S,4S)-1-allyloxycarbonyl-4-hydroxy-2-(2-methyl-3-oxo-1-butenyl)pyrrolidine (0.14 g).

IR (CH$_2$Cl$_2$): 1700, 1670 cm$^{-1}$

NMR (CDCl$_3$, δ): 1.82 (3H, s), 2.30 (3H, s), 2.23–2.47 (2H, m), 3.54–3.72 (2H, m), 4.55–4.77 (4H, m), 5.15–5.35 (2H, m), 5.72–6.07 (1H, m), 6.77–6.82 (1H, m)

Preparation 67

To a solution of (2S,4S)-1-allyloxycarbonyl-4-hydroxy-2-(2-methyl-3-oxo-1-butenyl)pyrrolidine (4.00 g) in N,N-dimethylformamide (40 ml) were added imidazole (2.70 g) and t-butyldimethylsilyl chloride (4.80 g). The resulting mixture was allowed to stand at ambient temperature for 2 hours. The mixture was diluted with ethyl acetate (200 ml), washed in turn with water and brine, dried over magnesium sulfate and evaporated. The residue was chromatographed on silica gel (100 ml) eluting with a mixture of n-hexane and ethyl acetate (9:1–8:2 V/V) to give (2S,4S)-1-allyloxycarbonyl-4-t-butyldimethylsilyloxy-2-(2-methyl-3-oxo-1-butenyl)-pyrrolidine (3.67 g).

IR (CH$_2$Cl$_2$): 1685, 1660 cm$^{-1}$

NMR (CDCl$_3$, δ): 0.05 (6H, d, J=6 Hz), 0.89 (9H, s), 1.70–1.91 (4H, m), 2.17–2.43 (4H, m), 3.35–3.72 (2H, m), 4.40–4.89 (4H, m), 5.04–5.39 (2H, m), 5.74–6.04 (1H, m), 6.76 (1H, d, J=8 Hz)

Preparation 68

(3S,4R)-4-[4-{(2S,4S)-1-Allyloxycarbonyl-4-(t-butyldimethylsilyloxy)pyrrolidin-2-yl}-3-methyl-2-oxo-3-butenyl]-3-[(1R)-1-t-butyldimethylsilyloxyethyl]-2-oxoazetidine was obtained in 97.2% yield in substantially the same manner as that of Preparation 2-(1).

IR (CH$_2$Cl$_2$): 1760, 1700, 1670 cm$^{-1}$

NMR (CDCl$_3$, δ): 0.07 (6H, s), 0.09 (6H, s), 0.87 (9H, s), 0.90 (9H, s), 1.20 (3H, d, J=6 Hz), 1.58–2.28 (5H, m), 2.69–2.92 (2H, m), 3.05–3.32 (1H, m), 3.41–3.77 (2H, m), 3.93–4.06 (1H, m), 4.13–4.29 (1H, m), 4.39–4.52 (1H, m), 4.52–4.68 (2H, m), 4.71–4.93 (1H, m), 5.05–5.20 (2H, m), 5.74–6.18 (2H, m), 6 69–6.88 (1H, m)

Preparation 69

To a solution of (2S,4S)-1-allyloxycarbonyl-4-hydroxy-2-(2-methyl-3-oxo-1-butenyl)pyrrolidine (4.00 g) in iodomethane (20 ml) was added silver oxide (20 g), and the mixture was allowed to stand at ambient temperature for 2 days. The resulting precipitate was removed by filtration and the filtrate was evaporated in vacuo. The residue was chromatographed on silica gel (50 ml) eluting with a mixture of n-hexane and ethyl acetate (6:4 V/V) to give (2S,4S)-1-allyloxycarbonyl-4-methoxy-2-(2-methyl-3-oxo-1-butenyl)pyrrolidine (2.31 g).

IR (CH$_2$Cl$_2$): 1690, 1660 cm$^{-1}$

NMR (CDCl$_3$, δ): 1.73–2.12 (4H, m), 2.17–2.42 (4H, m), 3.32 (3H, s), 3.51–3.75 (2H, m), 3.96–4.05 (1H, m), 4.42–4.92 (3H, m), 5.08–5.42 (2H, m), 5.71–6.03 (1H, m), 6.67 (1H, d, J=8 Hz)

Preparation 70

(3S,4R)-4-[4-{(2S,4S)-1-Allyloxycarbonyl-4-methoxypyrrolidin-2-yl}-3-methyl-2-oxo-3-butenyl]-3-[(1R)-1-t-butyldimethylsilyloxyethyl]-2-oxoazetidine was obtained in 70.4% yield in substantially the same manner as that of Preparation 2-(1).

IR (CH$_2$Cl$_2$): 1755, 1695, 1660 cm$^{-1}$

NMR (CDCl$_3$, δ): 0.05 (6H, s), 0.85 (9H, s), 1.20 (2H, d, J=6 Hz), 1.62–2.41 (5H, m), 2.73–3.17 (3H, m), 3.32 (3H, s), 3.48–3.79 (2H, m), 3.89–4.28 (3H, m), 4.49–4.66 (2H, m), 4.66–4.86 (1H, m), 5.06–5.39 (2H, m), 5.77–6.00 (1H, m), 6.00–6.19 (1H, m), 6.66 (2H, d, J=8 Hz)

EXAMPLE 1-(1)

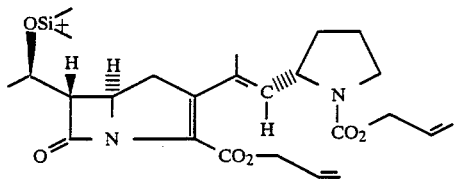

Allyl 2-[(3S,4R)-4-[(E)-4-{(2S)-1-allyloxycarbonylpyrrolidin2-yl}-3-methyl-2-oxo-3-butenyl]-3-{(1R)-1-t-butyldimethylsilyloxyethyl)-2-oxoazetidin-1-yl]-2 triphenylphosphoranylideneacetate (9.78 g) was dissolved in degassed xylene (150 ml) and the solution was heated to 150° C. for 10 hours. Evaporation of the mixture gave a residue, which was chromatographed on silica gel (250 ml) eluting with a mixture of n-hexane and ethyl acetate (2:8–7:3 V/V) to give allyl (5R,6S)-3-[(E)-2-{(-2S)-1-allyloxycarbonylpyrrolidin-2-yl}-1-methylethenyl]-6-]((1R)-1-t-butyldimethylsilyloxyethyl]-7-oxo-1-azabicyclo[3.2.0]hept-2-ene-2-carboxylate (5.36 g).

IR (CH$_2$Cl$_2$): 1775, 1690 cm$^{-1}$

NMR (CDCl$_3$, δ): 0.06 (6H, s), 0.87 (9H, s), 1.23 (3H, d, J=7 Hz), 1.40–2.30 (4H, m), 1.88 (3H, br s), 2.77–3.15 (3H, m), 3.24–3.66 (2H, m), 3.85–4.29 (2H, m), 4.40–4.90 (5H, m), 5.00–5.60 (5H, m), 5.60–6.20 (2H, m)

EXAMPLE 1-(2)

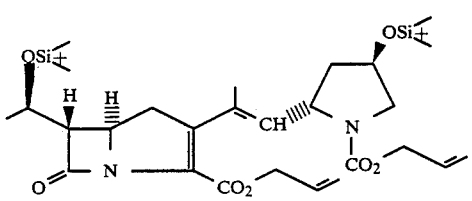

Allyl (5R,6S)-3-[2-{(2S,4R)-1-allyloxycarbonyl-4-t-butyldimethylsilyloxypyrrolidin-2-yl}-1-methylethenyl]-6-[(1R)-1-t-butyldimethylsilyloxyethyl]-7-oxo-1-azabicyclo[3.2.0]hept-2-ene-2-carboxylate (6.11 g) was obtained in 77.8% yield in substantially the same manner as that of Example 1(1).

IR (CH$_2$Cl$_2$) 1770, 1690 cm$^{-1}$

NMR (CDCl$_3$, δ): 0.09 (12H, s), 0.90 (18H, s), 1.25 (3H, d, J=6 Hz), 1.42–2.30 (2H, m), 1.90 (3H, d, J=1 Hz), 2.82–3.26 (3H, m), 3.48 (2H, d, J=4 Hz), 3.93–4.47 (3H, m), 4.47–4.93 (5H, m), 5.05–5.55 (5H, m), 5.68–6.22 (2H, m)

EXAMPLE 2

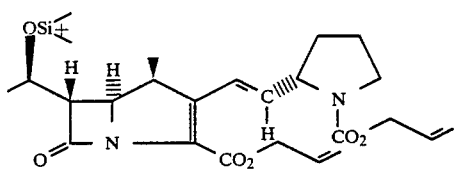

A solution of allyl 2-[(3S,4R)-4-[(1R)-4-{(2S)-1-allyloxycarbonylpyrrolidin-2-yl)-4-hydroxy-1-methyl-2 oxobutyl]-3-{(1R)-1-t-butyldimethylsilyloxyethyl]-2-oxoazetidin-1-yl]-2-triphenylphosphoranylideneacetate (2.36 g) in degassed toluene (120 ml) was heated to reflux for 8 hours. After cooling, the toluene was evaporated to give a residue of allyl (4S,5R,6S)-3-[2-{(2S)-1-allyloxycarbonylpyrrolidin-2-yl)-2-hydroxyethyl]-6-[(1R)-1-t-butyldimethylsilyloxyethyl]-4-methyl-7-oxo-1-azabicyclo[3.2.0]hept-2-ene-2-carboxylate and the residue was taken up into dichloromethane (90.0 ml). To the mixture were added dropwise triethylamine (1.02 ml) and methane sulfonyl chloride (0.52 ml) at 5° C. with stirring and the stirring was continued for 30 minutes at 5° C. To the resultant mixture was added 1,8-diazabicyclo-[5.4.0]-7-undecene (3.36 ml) and the resultant mixture was allowed to warm to around 40° C. After stirring at 40° C. for 2 hours, the mixture was diluted with ethyl acetate and washed in turn with aqueous ammonium chloride, water and brine, and dried over magnesium sulfate. Removal of the solvent gave a residue, which was chromatographed on silica gel (150 ml) eluting with a mixture of n-hexane and ethyl acetate (9:1–4:1 V/V) to give allyl (4S,5R,6S)-3-[(E)-2-{(2S)-1-allyloxycarbonylpyrrolidin-2-yl}-ethenyl]-6-[(1R)-1-t-butyldimethylsilyloxyethyl]-4-methyl-7-oxo-1-azabicyclo[3.2.0]-hept-2-ene-2-carboxylate (1.12 g).

IR (CH$_2$Cl$_2$): 1770, 1710, 1690 cm$^{-1}$

NMR (CDCl$_3$, δ): 0.12 (6H, s), 0.91 (9H, s), 1.19 (3H, d, J=8 Hz), 1.29 (3H, d, J=6 Hz), 1.64–2.32 (4H, m), 3.07–3.62 (2H, m), 3.95–4.32 (2H, m), 4.32–4.64 (3H, m), 4.64–4.79 (2H, m), 5.04–5.57 (4H, m), m), 7.12 (1H, d, J=17 Hz)

EXAMPLE 3-1)

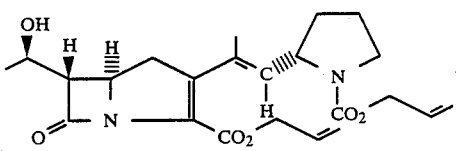

To a solution of allyl (5R,6S)-3-[(E)-2-{(2S)-1-allyloxycarbonylpyrrolidin-2-yl}-1-methylethenyl]-6-[(1R)-1-t-butyldimethylsilyloxyethyl]-7-oxo-1-azabicyclo[3.2.0]hept-2-ene-2-carboxylate (5.36 g) in tetrahydrofuran (60 ml) were added acetic acid (5.6 ml) and a 1M solution of tetrabutylammonium fluoride in tetrahydrofuran (49 ml) at ° C. After standing at ambient temperature for 7 hours and at 5° C. for 14 hours, the reaction mixture was taken up into a mixture of ethyl acetate (200 ml) and water (200 ml). After adjusting pH to around 7 with aqueous sodium hydrogen carbonate, the organic layer was separated, washed in turn with water and brine, and dried over magnesium sulfate. Removal of the solvent gave a residue, which was chromatographed on silica gel (150 ml) eluting with a mixture of n-hexane and ethyl acetate (8:2–3:7 V/V) to give allyl (5R,6S)-3-[(E)-2-(12S)-1-allyloxycarbonyl-pyrrolidin-2-yl)-1-methylethenyl]-6-[(1R)-1-hydroxyethyl]-7-oxo-1-azabicyclo[3.2.0]hept-2-ene-2-carboxylate (2.82 g).

IR (CH$_2$Cl$_2$): 3600, 1780, 1690 cm$^{-1}$

NMR (CDCl$_3$, δ): 1.32 (3H, d, J=7 Hz), 1.47–2.28 (4H, m), 1.86 (3H, br s), 2.80–3.23 (3H, m), 3.23.3.60 (2H, m), 3.85–4.30 (2H, m), 4.36–4.84 (5H, m), 5.03–5.50 (5H, m), 5.60–6.20(2H, m)

EXAMPLE 3-(2)

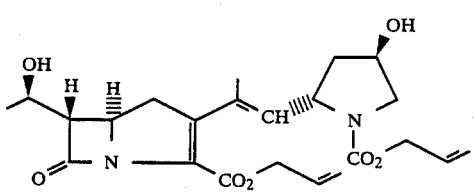

Allyl (5R,6S)-3-[2-{(2S,4R)-1-allyloxycarbonyl-4-hydroxypyrrolidin-2-yl}-1-methylethenyl]-6-[(1R)-1-hydroxyethyl]-7-oxo-1-azabicyclo[3.2.0]hept-2-ene-2-carboxylate (2.72 g) was obtained by reacting allyl (5R,6S)-3-[-{(2S,4R)-1-allyloxycarbonyl-4-t-butyldimethylsilyloxypyrrolidin- 2-yl)-1-methylethenyl]-6-[(1R)-1-t-butyldimethylsilyloxyethyl]-7-oxo-1-azabicyclo[3.2.0]hept-2-ene-2-carboxylate (6.10 g) with tetrabutylammonium fluoride in substantially the same manner as that of Example 3-(1).

IR (CH$_2$Cl$_2$): 3700, 1770, 1690 cm$^{-1}$)

NMR (CDCl$_3$, δ): 1.33 (3H, d, J=6 Hz), 1.90 (3H, d, J=1 Hz), 1.53–2.40 (4H, m), 2.84–3.26 (3H, m), 3.47–3.65 (2H, m), 3.92–4.30 (2H, m), 4.30–5.00 (6H, m), 5.00–5.60 (5H, m), 5.60–6.22 (2H, m)

EXAMPLE 3-3)

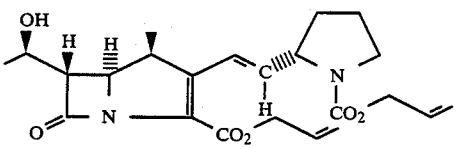

Allyl (4S,5R,6S)-3-[(E)-2-{(2S)-1-allyloxycarbonylpyrrolidin-2-yl}ethenyl]-6-[(1R)-1-hydroxyethyl]-4-methyl-7-oxo-1-azabicyclo[3.2.0]hept-2-ene-2-carboxylate (650 mg) was obtained by reacting allyl (4S,5R,6S)-3-{(E)-2 (2S)-1-allyloxycarbonylpyrrolidin-2-yl)ethenyl]-6-[(1R)-1-t-butyldimethylsilyloxyethyl]-4-methyl-7-oxo-1-azabicyclo[3.2.0]hept-2-ene-2-carboxylate (1.12 g) in substantially the same manner as that of Example 3-(1).

IR (CH$_2$Cl$_2$): 1770, 1710, 1690 cm$^{-1}$

NMR (CDCl$_3$, δ): 1.22 (3H, d, J=7 Hz), 1.37 (3H, d, J=6 Hz), 1.55–2.50 (4H, m), 2.29 (1H, br s), 3.23 (1H, dd, J=3, 6 Hz), 3.33–3.65 (3H, m), 4.05–4.33 (2H, m), 4.33–4.66 (3H, m), 4.66–4.85 (2H, m), 5.05–5.65 (4H, m), 5.65–6.25 (3H, m), 7.16 (1H, d, J=16 Hz)

Example 4-(1)

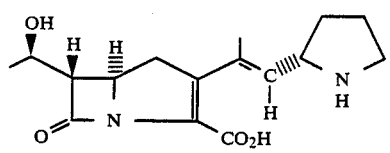

To a solution of allyl (5R,6S)-3-[(E)-2-{(2S)-1-allyloxycarbonylpyrrolidin-2-yl}-1-methylethenyl]-6-[(1R)-1-hydroxyethyl]-7-oxo-1-azabicyclo[3.2.0]hept-2-ene-2-carboxylate (2.82 g) in a mixture of tetrahydrofuran (28 ml) and ethanol (14 ml) were added successively triphenylphosphine (0.51 g), 5,5-dimethyl-1,3cyclohexanedione (dimedone) (1.79 g), and tetrakis-(triphenylphosphine) palladium (0) (220 mg). Stirring at ambient temperature for 1 hour gave a precipitate, which was collected by filtration, washed with tetrahydrofuran (40 ml) and dissolved in water (150 ml). The solution was washed with ethyl acetate (50 ml×2), concentrated in vacuo and lyophilized to give (5R,6S)-6-[(1R)-1-hydroxyethyl]-7-oxo-3-[(E)-2-(2S)-pyrrolidin-2-yl}-1-methylethenyl]-1-azabicyclo[b 3.2.0]hept-2-ene-2-carboxylic acid (1.52 g).

IR (Nujol)): 3250, 1760, 1580 cm$^{-1}$

NMR (D$_2$O, δ): 1.25 (3H, d, J=7Hz), 1.50—2.37 (4H, m), 1.88 (3H, d, J=1Hz), 2.60–3.53 (5H, m), 3.95–4.59 (3H, m), 5.45 (1H, dq, J=1, 9Hz)

Example 4-(2)

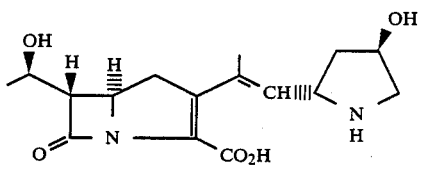

(5R,6S)-6-[(1R)-1-Hydroxyethyl]-3-[2-{(2S,4R)-4-hydroxypyrrolidin-2-yl)-1-methylethenyl]-7-oxo-1-azabicyclo [3.2.0]hept-2-ene-2-carboxylic acid (1.75 g) was obtained in 89.6% yield in substantially the same manner as that of Example 4-(1).

IR (Nujol): 3250, 1760, 1590 cm$^{-1}$

NMR (D$_2$O, δ): 1.27 (3H, d, J=6Hz), 1.93 (3H, d, J=1Hz), 1.55–2.45 (2H, m), 2.65–3.70 (5H, m), 3.95–4.38 (2H, m), 4.38–4.99 (2H, m), 5.30–5.56 (1H, m)

Example 4-(3)

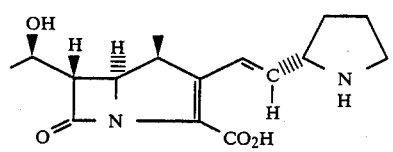

(4S,5R,6S)-6-[(1R)-1-Hydroxyethyl]-4-methyl-7-oxo-3-[(E)-2{(2S)-pyrrolidin-2-yl}ethenyl]-1-azabicyclo-[3.2.0]hept-2-ene-2-carboxylic acid (380 mg) was obtained in 82.1% yield in substantially the same manner as that of Example 4-(1).

IR (Nujol): 3300, 1750 cm$^{-1}$

NMR (D$_2$O, δ): 1.00 (3H, d, J=7Hz), 1.15 (3H, d, J=6Hz), 1.50–2.40 (4H, m), 3.00–3.50 (4H, m), 3.90–4.25 (3H, m), 5.83 (1H, dd, J=8,16Hz), 7.09 (1H, d, J=16Hz)

Example 5-(1)

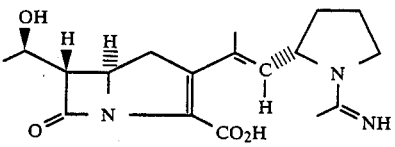

A solution of (5R,6S)-6-[(1R)-1-hydroxyethyl]-7-oxo-3-[(E)-2-{(2S)-pyrrolidin-2-yl]-1-methylethenyl]-1-azabicyclo [3.2.0]hept-2-ene-2-carboxylic acid (0.44 g) in water (30 ml) was adjusted to pH 8.5 with aqueous potassium carbonate at 0° C. and ethyl acetimidate hydrochloride (5.4 g) was added in portions while adjusting around pH 8.5 with addition of aqueous potassium carbonate. After stirring for 15 minutes at pH 8.5, the reaction mixture was washed with a mixture of ethyl acetate and tetrahydrofuran (9:1 V/V, 150 ml), and concentrated in vacuo. The residue was chromatographed on nonionic adsorption resin "Diaion HP-20" (Trademark, made by Mitsubishi Chemical Industries) (80 ml) eluting successively with water (200 ml) and 5% aqueous isopropyl alcohol (200 ml). The fractions containing the desired compound were collected and lyophilized to give (5R,6S)-3-[(E)-2-{(2S) 1-acetimidoylpyrrolidin-2-yl}-1-methylethenyl]-6-[(1R)-1-hydroxyethyl]-7-oxo-1-azabicyclo [3.2.0]hept-2-ene-2-carboxylic acid (241 mg).

IR (Nujol): 3200, 1760, 1670, 1590 cm⁻¹

NMR (D₂O, δ): 1.27 (3H, d, J=6Hz), 1.45-2.45 (10H, m), 2.60-3.80 (5H, m), 3.93-4.90 (3H, m), 5.23-5.60 (1H, m)

Example 5-(2)

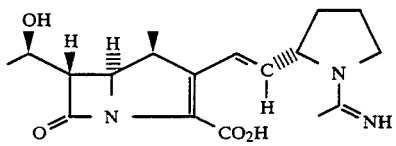

(4S,5R,6S)-3-[(E)-2-{(2S)-1-Acetimidoylpyrrolidin-2-yl}ethenyl]-6-[(1R)-1-hydroxyethyl]-4-methyl-7-oxo-1-azabicyclo [3.2.0]hept-2-ene-2-carboxylic acid (237 mg) was obtained in 83.6% yield in substantially the same manner as that of Example 5-(1).

IR (Nujol): 3300, 1740, 1590 cm⁻¹

NMR (D₂O, δ): 1.15(3H, d, J=7Hz), 1.31 (3H, d, J=6Hz),

| 1.73-2.50 (4H, m), 2.26 (S) | 3H, |
| 2.33 (s) | |

3.14-4.00 (5H, m), 4.00-4.41 (2H, m), 5.70-6.15 (1H, m), 6.75-7.50 (1H, m)

Example 6-(1)

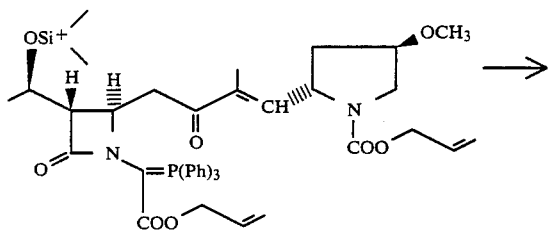

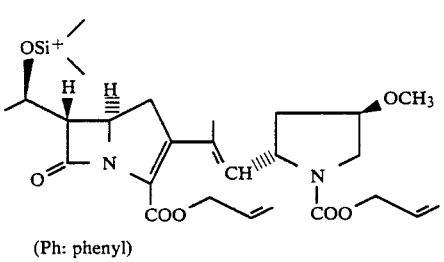

(Ph: phenyl)

Allyl (5R,6S)-3-[2-{(2S,4R)-1-allyloxycarbonyl-4-methoxypyrrolidin-2-yl}-1-methylethenyl]-6-[(1R)-1-t-butyldimethylsilyloxyethyl]-7-oxo-1-azabicyclo [3.2.0]hept-2-ene-2-carboxylate was obtained in 86.1% yield in substantially the same manner as that of Example 1-(1).

IR (neat): 1780, 1700 cm⁻¹

NMR (CDCl₃, δ): 0.10 (6H, s), 0.90 (9H, s), 1.25 (3H, d, J=6Hz), 1.88 (3H, d, J=1Hz), 1.55-2.45 (2H, m), 2.80-4.35 (8H, m), 3.31 (3H, s), 4.44-4.90 (5H, m), 5.00-5.58 (5H, m), 5.60-6.18 (2H, m)

Example 6-(2)

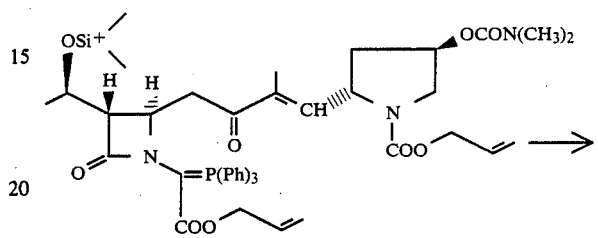

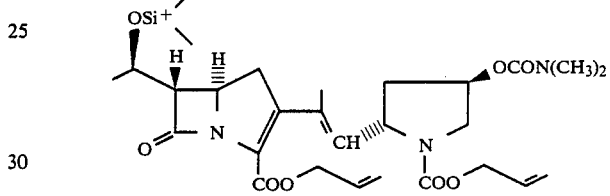

Allyl (5R,6S)-3-[2-[(2S,4R)-1-allyloxycarbonyl-4-(dimethylcarbamoyloxy) pyrrolidin-2-yl}-1-methylethenyl]-6-(1R)-1-t-butyldimethylsilyloxyethyl]-7-oxo-1-azabicyclo [3.2.0]hept-2-ene-2-carboxylate was obtained in 56.3% yield in substantially the same manner as that of Example 1-(1).

IR (CH₂Cl₂): 1780, 1700 cm⁻¹

NMR (CDCl₃, δ): 0.10 (6H, s), 0.90 (9H, s), 1.25 (3H, d, J=6Hz), 1.43-2.60 (2H, m), 1.91 (3H, d, J=1Hz), 2.89 (6H, s), 2.74-3.25 (3H, m), 3.44-3.90 (2H, m), 3.90-4.32 (2H, m), 4.45-4.86 (5H, m), 5 03-5.54 (6H, m), 5.60-6.18 (2H, m)

Example 7-(1)

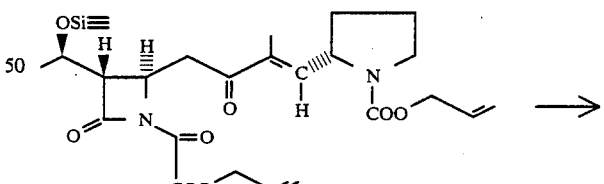

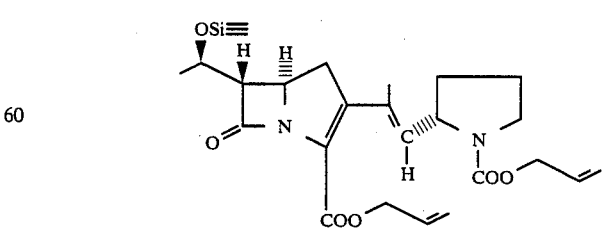

To a solution of allyl 2-[(3S,4R)-4-[(E)-4-{(2S)-1-allyloxycarbonylpyrrolidin-2-yl}-3-methyl-2-oxo-3-butenyl]-3{(1R)-1-trimethylsilyloxyethyl}-2-oxoazetidin-1-yl]glyoxylate obtained in Preparation 49 in toluene (39 ml) was added triethyl phosphite (43.78 ml). The resulting mixture was heated at 70°–80° C. for 2 hours under nitrogen atmosphere. To the reaction mixture were added toluene (350 ml) and hydroquinone (12.0 g) at room temperature. After refluxing for 9 hours under nitrogen atmosphere, the reaction mixture was washed in turn with aqueous potassium carbonate and brine, and dried over magnesium sulfate. Removal of the solvent gave a crude oil of allyl (5R,6S)-3-[(E)-2-{(2S)-1-allyloxycarbonylpyrrolidin-2-yl}-1-methylethenyl]-6[ (1R)-1-trimethylsilyloxyethyl]-7-oxo-1-azabicyclo 3.2.0]hept-2-ene-2-carboxylate.

IR $(CH_2Cl_2)$: 1765, 1715, 1680 cm$^{-m}$

NMR $(CDCl_3, \delta)$: 0.13 (9H, s), 1.26 (3H, d, J=6Hz), 1.5–2.3 (4H, m), 1.90 (3H, s), 2.8–3.2 (3H, m), 3.2–3.6 (2H, m), 3.8–4.3 (2H, m), 4.4–4.8 (5H, m), 5.0–5.5 (5H, m), 5.6–6.2 (2H, m)

Example (7-2)

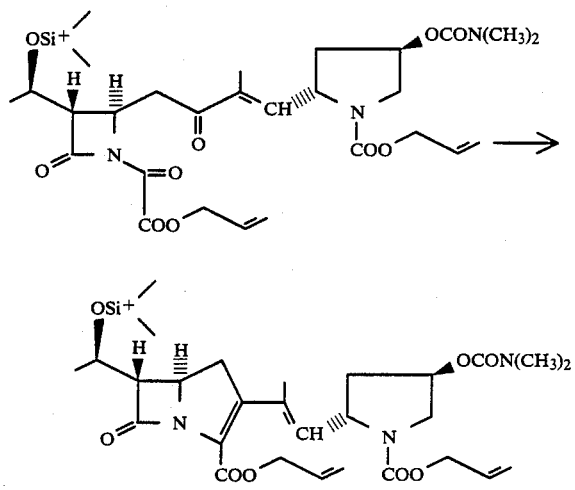

To a solution of allyl 2-[(3S,4R)-4-[4-{(2S,4R)-1-allyloxycarbonyl-4-(dimethylcarbamoyloxy) pyrrolidin-2-yl}-3-methyl-2-oxo-3-butenyl]-3-{(1R)-1-t-butyldimethylsilyloxyethyl}-2-oxoazetiin-1-yl]glyoxylate (0.44 g) in toluene (15 ml) was added triethyl phosphite (0.61 ml) and the resulting mixture was heated to 90° C. for 15 hours under nitrogen atmosphere. After evaporation of the solvent in vacuo, to the residue were added xylene (20 ml) and hydroquinone (20 mg) and the resulting mixture was heated to reflux for 10 hours under nitrogen atmosphere. Evaporation of the solvent gave a residue, which was chromatographed on silica gel (50 ml) eluting with a mixture of n-hexane and ethyl acetate (8:2–1:1 V/V) to give allyl (5R,6S)-3-[2-{(2S,4R)-1-allyloxycarbonyl-4-(dimethylcarbamoyloxy) pyrrolidin-2-yl}-1methylethenyl]-6-[(1R)-1-t-butyldimethylsilyloxyethyl]-7-oxo-1-azabicyclo [3.2.0]hept-2-ene-2-carboxylate (0.26 g).

IR $(CH_2Cl_2)$: 1780, 1700 cm$^{l1}$

NMR $(CDCl_3, \delta)$: 0.10 (6H, s), 0.90 (9H, s), 1.25 (3H, d, J=6Hz), 1.43–2.60 (2H, m), 1.91 (3H, d, J=1hz), 2.89 (6H, s), 2.74–3.25 (3H, m), 3.44–3.90 (2H, m), 3.90–4.32 (2H, m), 4.45–4.86 (5H, m), 5.03–5.54 (6H, m), 5.60–6.18 (2H, m)

Example 7-(3)

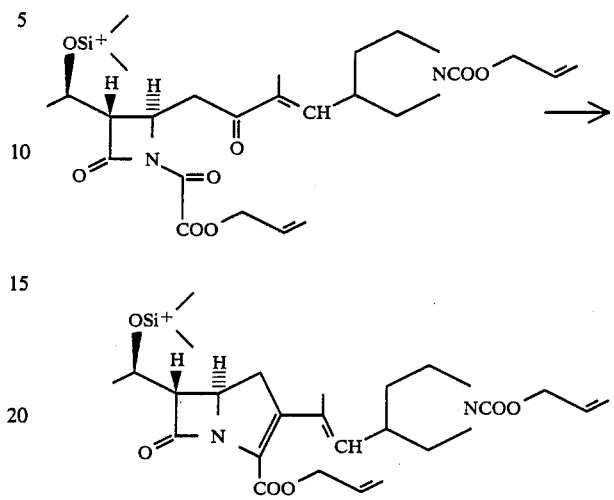

Allyl (5R,6S)-3-[2-{1-allyloxycarbonylpyrrolidin-3-yl}-1-methylethenyl]-6-[(1R)-1-t-butyldimethylsilyloxyethyl]-7-oxo-1-azabicyclo [3.2.0]hept-2-ene-2-carboxylate was obtained in 53.0% yield in substantially the same manner as that of Example 7-(1).

IR (Neat): 1780–1770, 1710–1695 cm$^{-1}$

NMR $(CDCl_3, \delta)$: 0.80 (6H, s), 0.90 (9H, s), 1.21 (3H, d, J=6Hz), 1.80 (3H, s), 4.5–4.8 (4H, m), 5.1–5.5 (4H, m), 5.8–6.2 (2H, m)

Example 7-(4)

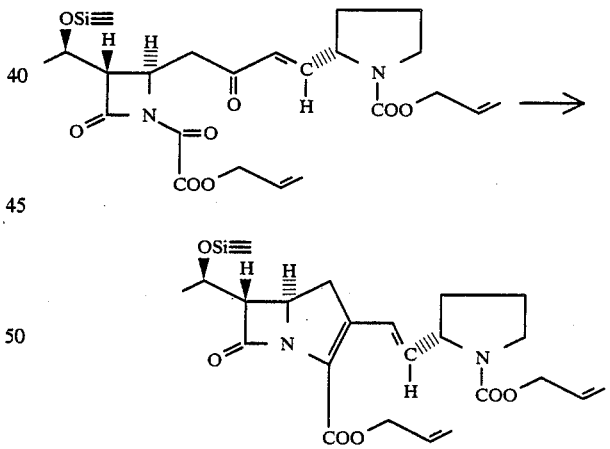

Allyl (5R,6S)-3-[(E)-2-{(2S)-1-allyloxycarbonylpyrrolidin-2-yl}ethenyl]-6-[(1R)-1-trimethylsilyloxyethyl]-7-oxo-1-azabicyclo [3.2.0]hept-2-ene-2-carboxylate was obtained in 95.0% yield in substantially the same manner as that of Example 7-(1).

IR (Nujol): 1780, 1715–1700 cm$^{-1}$

NMR $(CDCl_3, \delta)$: 0.14 (9H, s), 1.27 (3H, d, J=0.7Hz), 1.60–2.20 (4H, m), 2.84–3.17 (3H, m), 3.37–3.57 (2H, m), 3.92–4.26 (2H, m), 4.37–4.81 (5H, m), 5.06–5.53 (4H, m), 5.61–6.20 (3H, m), 7.11 (1H, d, J=14Hz)

Example 8-(1)

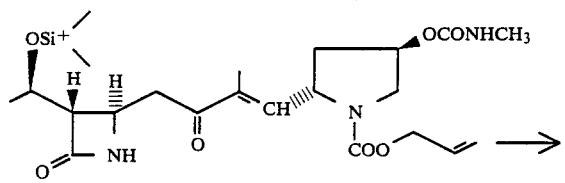

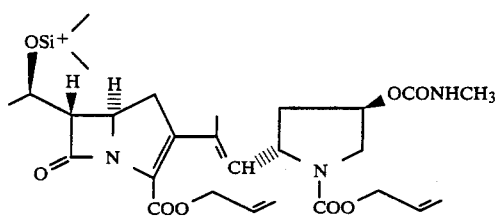

Allyl (5R,6S)-3-[2-{(2S,4R)-1-allyloxycarbonyl-4-methylcarbamoyloxy) pyrrolidin-2-yl}-1-methylethenyl]-6-[(1R)-1-t-butyldimethylsilyloxyethyl]-7-oxo-1-azabicyclo-[ 3.2.0]hept-2-ene-2-carboxylate was obtained in 90.4% yield in substantially the same manner as those of Preparation 48-(1) and Example 7-(2).

IR (Neat): 1780, 1710 cm$^{-1}$

NMR (CDCl$_3$, δ): 0.95 (6H, s), 0.89 (9H, s), 1.24 (3H, d, J=6Hz), 1.89 (3H, s), 1.60-2.47 (2H, m), 2.77-3.20 (3H, m), 3.51-3.74 (2H, m), 3.90-4.34 (2H, m), 4.40-4.88 (6H, m), 5.00-5.49 (6H, m), 5.65-6.19 (2H, m)

Example 8-(2)

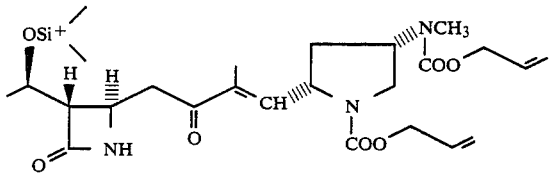

Allyl (5R,6S)-3-[2-{(2S,4S)-1-allyloxycarbonyl-4-(N-allyloxycarbonyl-N-methylamino) pyrrolidin-2-yl}-1-methylethenyl]-6-[(1R)-1-t-butyldimethylsilyloxyethyl]-7-oxo-1-azabicyclo [3.2.0]hept-2-ene-2-carboxylate was obtained in 45.3% yield in substantially the same manner as those of Preparation 48-(1) and Example (7-2).

IR (Neat): 1780, 1700 cm$^{-1}$

NMR (CDCl$_3$, δ): 0.10 (6H, s), 0.90 (9H, s), 1.23 (3H, d, J=6Hz), 1.87 (3H, d, J=1Hz), 1.60-2.50 (2H, m), 2.83 (3H, s), 2.75-4.30 (7H, m), 4.40-4.90 (8H, m), 5.03-5.50 (7H, m), 5.61-6.16 (3H, m)

Example 8-(3)

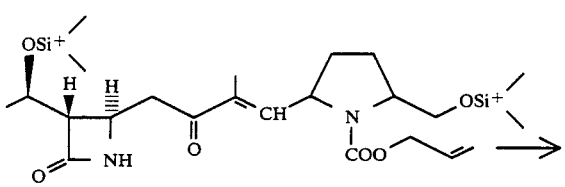

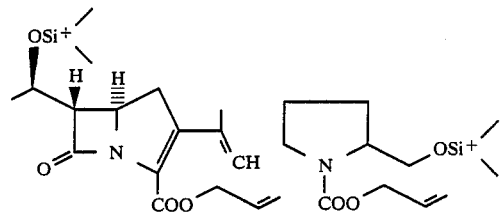

Allyl (5R,6S)-3-[2-{1-allyloxycarbonyl-5-(t-butyldimethylsilyloxymethyl) pyrrolidin-2-yl}-1methylethenyl]-6-[(1R)-1-t-butyldimethylsilyloxyethyl]-7-oxo-1-azabicyclo [3.2.0]hept-2-ene-2-carboxylate was obtained in 63.1% yield in substantially the same manner as those of Preparation 48-(1) and Example (7-2).

IR (CHCl$_3$): 1770, 1690 cm$^{-1}$

NMR (CDCl$_3$, δ): 0.07 (12H, s), 0.90 (18H, s), 1.25 (3H, d, J=6Hz), 1.50-2.50 (4H, m), 1.85 (3H, s), 2.80-3.30 (3H, m), 3.40-4.35 (6H, m), 4.45-4.80 (4H, m), 4.98-5.50 (5H, m), 5.60-6.20 (2H, m)

Example 8-(4)

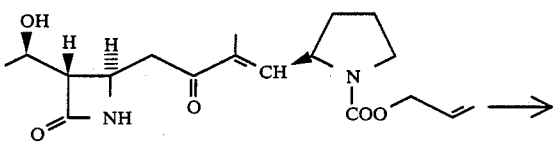

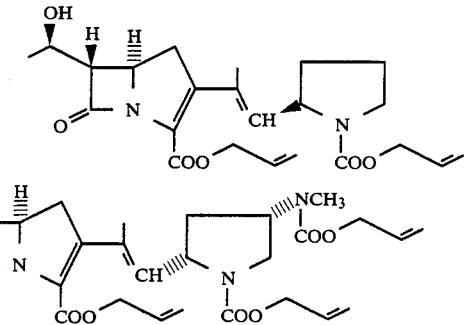

Allyl (5R,6S)-3-[2-{(2R)-1-allyloxycarbonylpyrrolidin-2yl}-1-methylethenyl]-6[(1R)-1-hydroxyethyl]-7-oxo-1-azabicyclo [3.2.0]hept-2-ene-2-carboxylate (2.56 g) was obtained in substantially the same manner as those of Preparation 49 and Examples 7-(1) and 10-(1).

NMR (CDCl$_3$, δ): 1.32 (3H, d, J=7), 1.88 (3H, s), 1.6-2.3 (4H, m), 2.8-3.2 (3H, m), 3.3-3.6 (2H, m), 4.0-4.3 (2H, m), 4.4-4.8 (5H, m), 5.1-5.5 (5H, m), 5.7-6.2 (2H, m)

Example 8-(5)

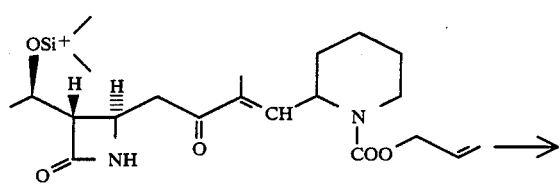

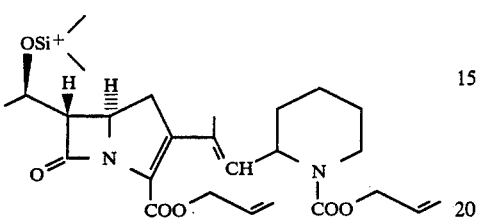

Allyl (5R,6S)-3-[2-(1-allyloxycarbonylpiperidin-2-yl)-1-methylethenyl]-6-[(1R)-1-t-butyldimethylsilyloxyethyl]-7-oxo-1-azabicyclo [3.2.0]hept-2-ene-2-carboxylate was obtained in 58.6% yield in substantially the same manner as those of Preparation 48-(1) and Example 7-(2).

IR (CHCl$_3$): 1770, 1720, 1680 cm$^{-1}$

NMR (CDCl$_3$, δ): 0.12 (6H, s), 0.92 (9H, s), 1.28 (3H, d, J=7Hz), 1.5-2.0 (6H, m), 1.88 (3H, br, s), 2.7-3.2 (3H, m), 3.9-4.3 (4H, m), 4.5-4.7 (4H, m), 5.0-5.5 (5H, m), 5.7-6.1 (3H, m)

Example 8-(6)

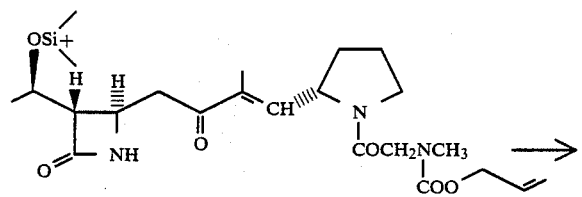

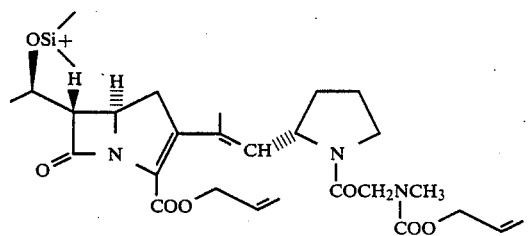

Allyl (5R,6S)-3-[2-{(2S)-1-(N-allyloxycarbonyl-N-methylaminoacetyl) pyrrolidin-2-yl}-1-methylethenyl]-6-[(1R)-1-t-butyldimethylsilyloxyethyl]-7-oxo-1azabicyclo[3.2.0]hept-2-ene-2-carboxylate (3.46 g) was obtained from the compound prepared in Preparation 45-(8) in substantially the same manner as those of Preparation 48-(1) and Example 7-(2).

IR (CHCl$_3$): 1775, 1700, 1650 cm$^{-1}$

NMR (CDCl$_3$, δ): 0.08 (6H, s), 0.88 (9H, s), 1.88 (3H, br. s), 3.00 (3H, s), 2.8-3.1 (3H, m), 3.4-3.7 (2H, m), 3.9-4.3 (4H, m), 4.5-4.8 (5H, m), 5.0-5.5 (5H, m), 5.6-6.1 (2H, m)

Example 8-(7)

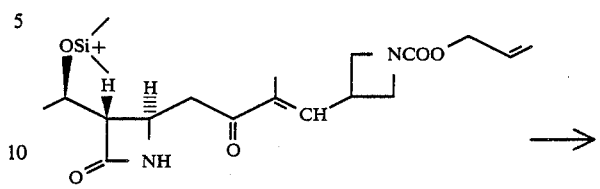

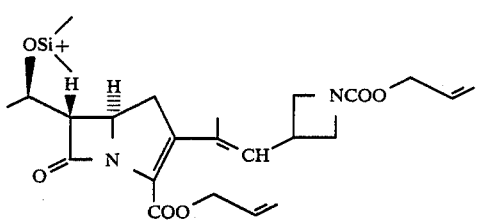

Allyl (5R,6S)-3-[2-(1-allyloxycarbonylazetidin-3-yl)-1-methylethenyl]-6[(1R)-1-butyldimethylsilyloxyethyl]-7-oxo-1-azabicyclo [3.2.0]hept-2-ene-2-carboxylate was obtained in 71.5% yield in substantially the same manner as those of Preparation 48-(1) and Example 7-(2).

IR (Nujol): 1775, 1720, 1705, 1685 cm$^{-1}$

NMR (CDCl$_3$, δ): 0.08 (6H, s), 0.88 (9H, s), 1.22 (6H, d, J=6Hz), 1.74 (3H, d, J=1Hz), 2.83-3.18 (3H, m), 3.31-3.86 (3H, m), 3.96-4.35 (4H, m), 4.45-4.77 (4H, m), 5.08-5.48 (4H, m), 5.60-6.18 (3H, m)

Example 8-(8)

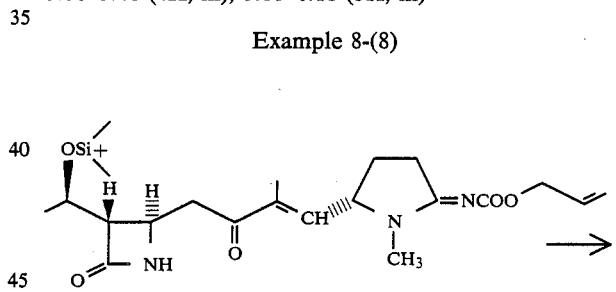

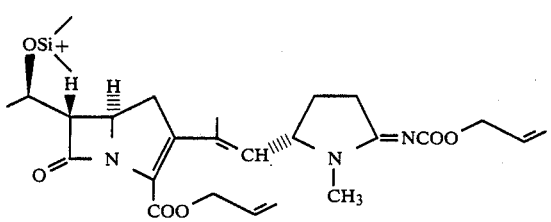

Allyl (5R,6S)-3-[2-{(2S)-5-allyloxycarbonylimino-1-methylpyrrolidin-2-yl}-1-methylethenyl]-6-[(1R)-1-t-butyldimethylsilyloxyethyl]-7-oxo-1-azabicyclo [3.2.0]hept-2-ene-2-carboxylate was obtained in 90.3% yield in substantially the same manner as those of Preparation 48-(1) and Example 7-(2).

IR (CH$_2$Cl$_2$): 1775, 1720, 1675 cm$^{-1}$

NMR (CDCl$_3$, δ): 0.08 (6H, s), 0.89 (9H, s), 1.81 (3H, d, J=1Hz), 2.81 (3H, s), 2.8-3.2 (3H, m), 4.4-4.7 (4H, m), 5.0-5.4 (4H, m), 5.6-6.2 (2H, m)

Example 9-(1)

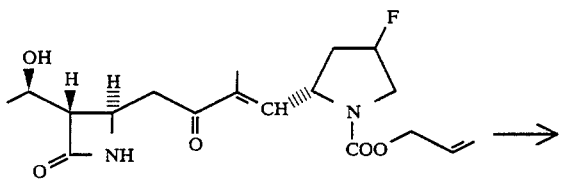

Allyl (5R,6S)-3-[2-{(2S)-1-allyloxycarbonyl-4-fluoropyrrolidin-2-ylo}-1-methylethenyl]-6-[(1R)-1trimethylsilyloxyethyl]-7-oxo-1-azabicyclo [3.2.0]hept-2-ene-2-carboxylate was obtained quantitatively in substantially the same manner as those of Preparation and Example 7-(1).

IR (CHCl₃) 1770, 1690 cm⁻¹

Example 9-(2)

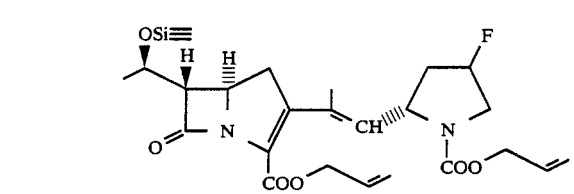

Allyl (5R,6S)-3-[2-(1-allyloxycarbonyl-5-methoxymethylpyrrolidin-2-yl)-1-methylethenyl]-6-[(1R)-1-trimethylsilyloxyethyl]-7-oxo-1-azabicyclo[3.2.0]hept-2-ene-2-carboxylate was obtained quantitatively in substantially the same manner as those of Preparation 49 and Example 7-(1).

IR (Nujol): 3420, 1760, 1690 cm⁻¹

Example 9-(3)

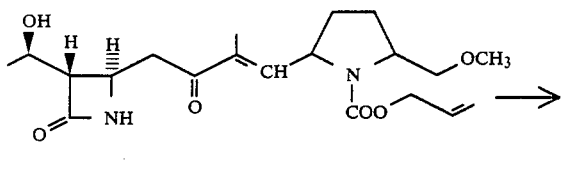

Allyl (5R,6S)-3-[2-{(3R)-4-allyloxycarbonylmorpholin-3-yl}-1-methylethenyl]-6-[(1R)-1-trimethylsiloloxyethyl]-7-oxo-1-azabicyclo [3.2.0]hept-2-ene-2-carboxylate was obtained in 62.6% yield in substantially the same manner as those of Preparation 49 and Example 7-(1).

IR (CHCl₃): 1770, 1710, 1690 cm⁻¹

NMR (CDCl₃, δ): 0 06 (9H, s), 1.18 (3H, d, J=6Hz), 1.80 (3H, d, J=]Hz), 2.7–4.2 (11H, m), 4.3–4.8 (5H, m), 4.8–5.4 (4H, m), 5.5–6.1 (3H, m)

Example 10-(1)

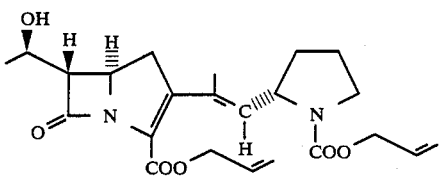

To a solution of allyl (5R,6S)-3-[(E)-2-{(2 S)-1-allyloxycarbonylpyrrolidin-2-yl}-1-methylethenyl]-6-[(1R)-1-trimethylsilyloxyethyl]-7-oxo-1-azabicyclo[3.2.0]-hept-2-ene-2-carboxylate obtained in Example 7-(1) in ethyl acetate (73 ml) were added acetic acid (12.5 ml) and a 1M solution of tetrabutylammonium fluoride in tetrahydrofuran (51.1 ml) at 0° C. After stirring at 0° C. for 30 minutes, the reaction mixture was taken up into a mixture of ethyl acetate (300 ml) and water (175 ml). The organic layer was separated, washed in turn with water, brine, aqueous sodium hydrogen carbonate and brine. The organic layer was dried over magnesium sulfate and evaporated. The residue was chromatographed on silica gel (315 ml) eluting with a mixture of n-hexane and ethyl acetate (9 1-2:5 V/V) to give allyl (5R,6S)-3-[(E)-2-{(2S)-1-allyloxycarbonylpyrrolidin-2-yl}-1-methylethenyl]-6-[(1R)-1-hydroxyethyl]-7-oxo-1-azabicyclo[3.2.0]hept-2-ene-2-carboxylate (20.40 g).

IR (CH₂Cl₂): 3600, 1780, 1690 cm⁻¹

NMR (CDCl₃, δ): 1.32 (3H, d, J=7Hz), 1.5–2.3 (4H, m), 1.86 (3H, br. s), 2.8–3.2 (3H, m), 3.2–3.6 (2H, m), 3.8–4.3 (2H, m), 4.3–4.8 (5H, m), 5.0–5.5 (5H, m), 5.6–6.2 (2H, m)

Example 10-(2)

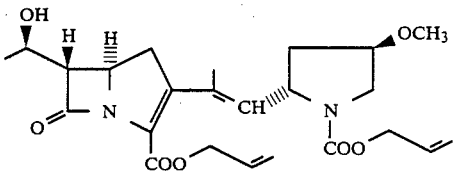

Allyl (5R,6S)-3-[2-{(2S,4R)-1-allyloxycarbonyl-4-methoxypyrrolidin-2-yl}-1-methylethenyl]-6-[(1R)-1hydroxyethyl]-7-oxo-1-azabicyclo 3.2.0]hept-2-ene-2carboxylate was obtained in 67.6% yield in substantially the same manner as that of Example 3-(1).

IR (CH₁Cl₂): 3350, 1760, 1690 cm⁻¹

NMR (CDCl₃, δ): 1.32 (3H, d, J=6Hz), 1.88 (3H, d, J=1Hz), 1.55–2.43 (3H, m), 2.85–4.30 (8H, m), 3.32 (3H, s), 4.45–4.90 (5H, m), 5.04–5.60 (5H, m), 5.60–6.19 (2H, m)

Example 10-(3)

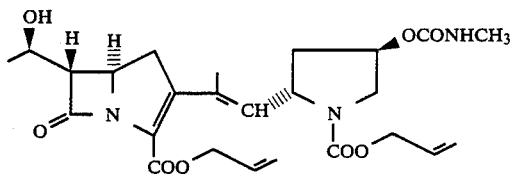

Allyl (5R,6S)-3-[2-{(2S,4R)-1-allyloxycarbonyl-4-(methylcarbamoyloxy) pyrrolidin-2-yl}-1-methylethenyl]-6[(1R)-1-hydroxyethyl]-7-oxo-1-azabicyclo[3.2.0]hept-2-ene-2-carboxylate was obtained in 50.5% yield in substantially the same manner as that of Example 3-(1).

NMR (CDCl$_3$, δ): 1.32 (3H, d, J=6Hz), 1.87 (3H, d, J=1Hz), 1.60–2.50 (3H, m), 2.76–3.28 (6H, m), 3.38–3.86 (2H, m), 3.92–4.30 (2H, m), 4.37–4.92 (6H, m), 4.95–5.47 (6H, m), 5.61–6.42 (2H, m).

Example 10-(4)

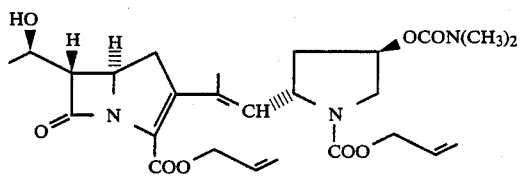

Allyl (5R,6S)-3-[2-{(2S,4R)-1-allyloxycarbonyl-4-(dimethylcarbamoyloxy) pyrrolidin-2-yl}-1-methylethenyl]-6-[(1R)-1-hydroxyethyl]-7-oxo-1-azabicyclo[3.2.0]hept-2-ene-2-carboxylate was obtained in 75.6% yield in substantially the same manner as that of Example 3-(1).

IR (CH$_2$Cl$_2$): 3370, 1740, 1700 cm$^{-1}$

NMR (CDCl$_3$, δ): 1.34 (3H, d, J=6Hz), 1.90 (3H, d, J=1Hz), 1.60–2.65 (3H, m), 2.90 (6H, s), 2.85–3.24 (3H, m), 3.42–3.85 (2H, m), 3.90–4.35 (2H, m), 4.43–4.86 (5H, m), 5.00–5.49 (6H, m), 5.58–6.20 (2H, m)

Example 10-(5)

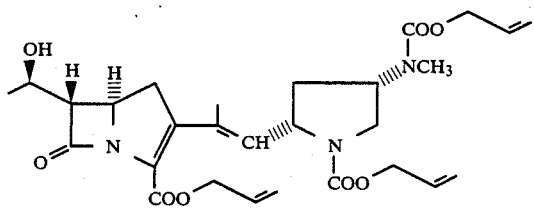

Allyl (5R,6S)-3-[2-{(2S,4S)-1-allyloxycarbonyl-4-(N-allyloxycarbonyl-N-methylamino) pyrrolidin-2-yl}-1-methylethenyl]-6-[(1R)-1-hydroxyethyl]-7-oxo-1azabicyclo[3.2.0]hept-2-ene-2-carboxylate was obtained in 55.0% yield in substantially the same manner as that of Example 3-(1).

IR (CH$_2$Cl$_2$): 1770, 1690 cm$^{-1}$

NMR (CDCl$_3$, δ): 1.33 (3H, d, J=6Hz), 1.87 (3H, d, J=1Hz), 1.60–2.48 (3H, m), 2.85 (3H, s), 2.75–3.40 (4H, m), 3.55–4.33 (3H, m), 4.36–4.92 (8H, m), 4.98–5.56 (7H, m), 5.60–6.19 (3H, m)

Example 10-(6)

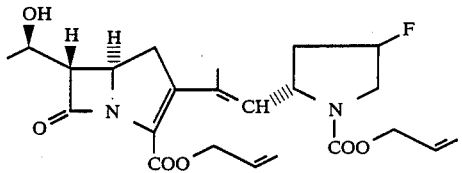

Allyl (5R,6S)-3-[2-{(2S)-1-allyloxycarbonyl-4-fluoropyrrolidin-2-yl}-1-methylethenyl]-6-[(1R)-1-hydroxyehtyl]-7-oxo-1-azabicyclo [3.2.0]hept-2-ene-2carboxylate was obtained in 57.2% yield in substantially the same manner as that of Example 3-(1).

IR (CHCl$_3$): 3430, 1770, 1690 cm$^{-1}$

NMR (CDCl$_3$, δ): 1.30 (3H, d, J=7Hz), 1.90 (3H, s), 1.60–2.30 (2H, m), 2.70–3.22 (3H, m), 3.30–6.20 (14H, m), 4.58 (2H, d, J=5Hz), 4.70 (2H, d, J=5Hz),

19 FNMR (CDCl$_3$, CF$_3$CO$_2$H) −91.9 ppm (m)

Example 10-(7)

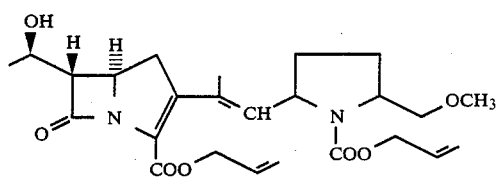

Allyl (5R,6S)-3-[2-(1-allyloxycarbonyl-5-methoxymethylpyrrolidin-2-yl)-1-methylethenyl]-6-[(1R)-1-hydroxyethyl]-7-oxo-1-azabicyclo [3.2.0]hept-2-ene-2-carboxylate was obtained in 60.8% yield in substantially the same manner as that of Example 3-(1).

IR (Nujol): 3400, 1770, 1720, 1690 cm$^{-1}$

Example 10-(8)

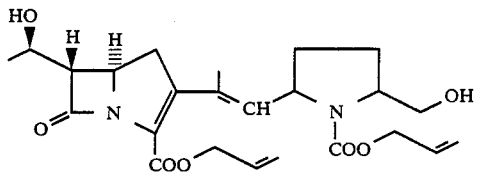

Allyl (5R,6S)-3-[2-(1-allyloxycarbonyl-5-hydroxymethylpyrrolidin-2-yl)-1-methylethenyl]-6-[(1R)-1-hydroxyethyl]-7-oxo-1-azabicyclo [3.2.0]hept-2-ene-2carboxylate was obtained in 50.2% yield in substantially the same manner as that of Example 3-(1).

IR (CHCl$_3$): 3400, 1775, 1720, 1670 cm$^{-1}$

Example 10-(9)

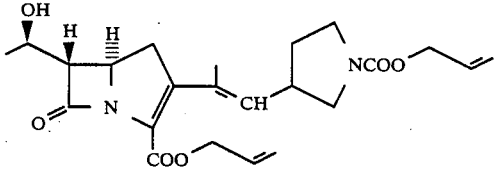

Allyl (5R,6S)-3-[2-(1-allyloxycarbonylpyrrolidin-3-yl)-1-methylethenyl]-6-[(1R)-1-hydroxyethyl]-7-oxo-1azabicyclo[3.2.0]hept-2-ene-2-carboxylate was obtained in 68.2% yield in substantially the same manner as that of Example 3-(1).

IR (Neat): 3450–3250, 1780–1765, 1710–1675 cm$^{-1}$

NMR (CDCl$_3$, δ): 1.31 (3H, d, J=6Hz), 1.83 (3H, s)

Example 10-(10)

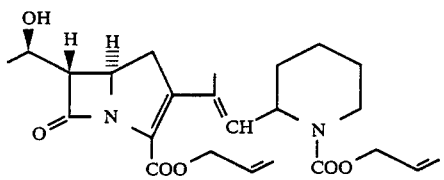

Allyl (5R,6S)-3-[2-(1-allyloxycarbonylpiperidin-2-yl)-1-methylethenyl]-6-[(1R)-1-hydroxyethyl]-7-oxo-1azabicyclo[3.2.0]hept-2-ene-2-carboxylate was obtained in 37.6% yield in substantially the same manner as that of Example (3-1).

IR (CHCl$_3$): 3400, 1770, 1720, 1690 cm$^{-1}$

NMR (CDCl$_3$, δ): 1.35 (3H, d, J=6Hz), 1.5–2.1 (6H, m),
1.88 (3H, br. s), 2.7–3.3 (3H, m), 3.9–4.3 (4H, m), 4.5–4.8 (4H, m), 5.0–5.5 (5H, m), 5.7–6.2 (3H, m)

Example 10-(11)

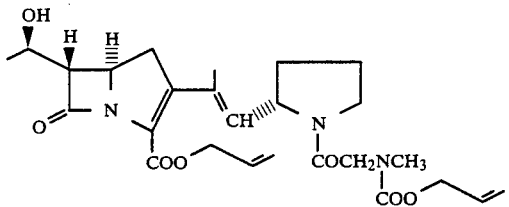

Allyl (5R,6S)-3-[2-{(2S)-1-(N-allyloxycarbonyl-N-methylaminoacetyl) pyrrolidin-2-yl}-1-methylethenyl]-6-[ [(1R)-1-hydroxyethyl]-7-oxo-1-azabicyclo[3.2.0-]hept-2-ene-2-carboxylate was obtained in 33.2% yield in substantially the same manner as that of Example 3-(1).

NMR (CDCl$_3$, δ): 1.34 (3H, d, J=7Hz), 1.90 (3H, br s), 3.01 (3h, s), 2.8–3.2 (3H, m), 3.3–3.7 (2H, m), 3.9–4.3 (4H, m), 4.5–4.8 (5H, m), 5.1–5.5 (5H, m), 5.6–6.1 (2H, m)

Example 10-(12)

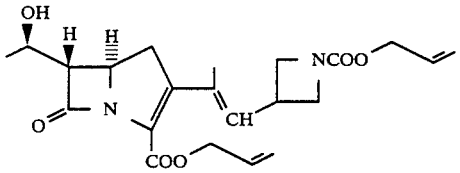

Allyl (5R,6S)-3-[2-(1-allyloxycarbonylazetidin-3-yl)-1-methylethenyl]-6-[(1R)-1-hydroxyethyl]-7-oxo-1-azabicyclo [3.2.0]hept-2-ene-2-carboxylate was obtained in 43.0% yield in the same manner as that of Example (3-1).

IR (Nujol): 1765, 1700 cm$^{-1}$

NMR (CDCl$_3$, δ): 1.33 (3H, d, J=7Hz), 1.74 (3H, S), 2.88–3.23 (2H, m), 3.20–3.85 (3H, m), 3.95–4.37 (5H, m), 4.42–4.80 (4H, m), 5.06–5.40 (4H, m), 5.62–6.18 (3H, m)

Example 10-(13)

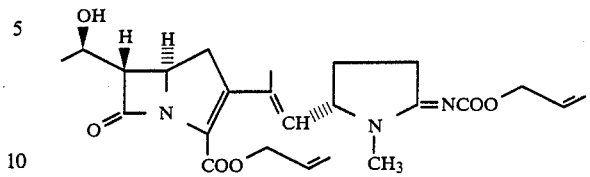

Allyl (5R,6S)-3-[2-{(2S)-5-allyloxycarbonylimino-1-methylpyrrolidin-2-yl)-1-methylethenyl]-6-[(1R)-1-hydroxyethyl]-7-oxo-1-azabicyclo [3.2.0]hept-2-ene-2-carboxylate was obtained in 26.8% yield in substantially the same manner as that of Example 3-(1).

IR (CH$_2$Cl$_2$): 1800, 1730, 1680 cm$^{-1}$

NMR (CDCl$_3$, δ): 1.35 (3H, d, J=6Hz), 2.92 (3H, d, J=1Hz), 2.97 (3H, s), 2.8–3.4 (5H, m), 4.0–4.8 (7H, m), 5.1–5.6 (5H, m), 5.7–6.2 (2H, m)

Example 10-(14)

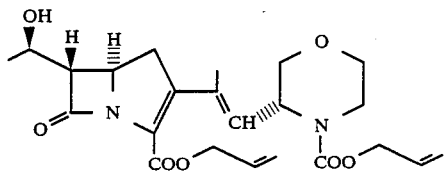

Allyl (5R,6S)-3-[2-{(3R)-4-allyloxycarbonylmorpholin-3-yl}-1-methylethenyl]-6-[(1R)-1-hydroxyethyl]-7-oxo-1azabicyclo[3.2.0]hept-2-ene-2-carboxylate was obtained in 90.8% yield in substantially the same manner as that of Example 3-(1).

IR (CHCl$_3$): 3400, 1770, 1720, 1690 cm$^{-1}$

NMR (CDCl$_3$, δ): 1.33 (3H, d, J=6Hz), 1.90 (3H, d, J=1Hz), 2.30 (1H, br. s), 2.8–4.4 (11H, m), 4.4–4.9 (5H, m), 5.0–5.5 (4H, m), 5.6–6.2 (3H, m)

Example 10-(15)

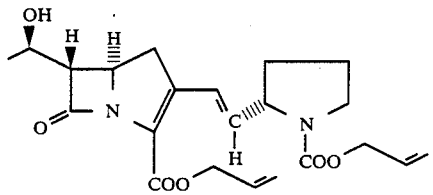

Allyl (5R,6S)-3-[(E)-2-{(2S)-1-allyloxycarbonylpyrrolidin-2-yl}ethenyl]-6-[(1R)-1-hydroxyethyl]-7-oxo-1-azabicyclo [3.2.0]hept-2-ene-2-carboxylate was obtained in 73.0% yield in substantially the same manner as that of Example 3-(1).

IR (Nujol): 3350–3100, 1790–1665, 1745 cm$^{-1}$

NMR (CDCl$_3$, δ): 1.35 (3H, d, J=7Hz), 1.70–2.27 (5H, m), 2.92–3.21 (3H, m), 3.37–3.60 (2H, m), 3.97–4.35 (2H, m), 4.35–4.83 (5H, m), 5.00–5.54 (4H, m), 5.61–6.23 (3H, m), 7.11 (1H, d, J=14Hz)

Example 11-(1)

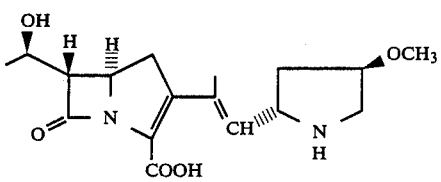

(5R,6S)-6-[(1R)-1-Hydroxyethyl]-3-[2-{(2S,4R)-4-methoxypyrrolidin-2-yl}-1-methylethenyl[-7-oxo-1-azabicyclo-[3.2.0]hept-2-ene-2-carboxylic acid was obtained in 67.1% yield in substantially the same manner as that of Example 4 -(1).

IR (Nujol): 3300, 1760 cm$^{-1}$

NMR (D$_2$O, δ): 1.27 (3H, d, J=6Hz), 1.90 (3H, d, J=1Hz), 1.63–2.64 (2H, m), 2.64–3.65 (5H, m), 3.35 (3H, s), 3.92–4.80 (4H, m), 5.42 (1H, dq, J=1,8Hz)

Example 11-(2)

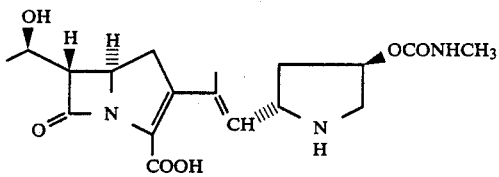

(5R,6S)-6-[(1R)-1-Hydroxyethyl]-3-[2-{(2S,4R)-4-(methylcarbamoyloxy) pyrrolidin-2-yl}-1-methylethenyl]-7-oxo-1-azabicyclo [3.2.0]hept.2-ene-2-carboxylic acid was obtained in 81.7% yield in substantially the same manner as that of Example 4-(1).

IR (Nujol): 3350, 1760, 1710 cm$^{-1}$

NMR (D$_2$O, δ): 1.28 (3H, d, J=6Hz), 1.95 (3H, d, J=1Hz), 2.72 (3H, s), 1.60–3.25 (4H, m), 3.25–3.92 (3H, m), 4.00–4.45 (2H, m), 4.45–5.05 (1H, m), 5.20–5.70 (2H, m)

Example 11-(3)

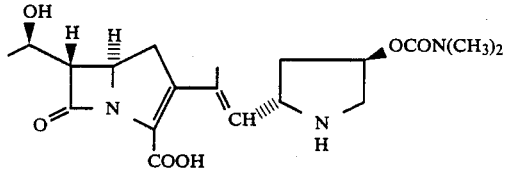

(5R,6S)-3-[2-{(2S,4R)-4-(Dimethylcarbamoyloxy)-pyrrolidin-2-yl)-1-methylethenyl]-6-[(1R)-1-hydroxyethyl]-7-oxo-1-azabicyclo 3.2.0]hept-2-ene-2-carboxylic acid was obtained in 66.4% yield in substantially the same manner as that of Example 4-(1).

IR (Nujol): 3350, 1760, 1690 cm$^{-1}$

NMR (D$_2$O, δ): 1.28 (3H, d, J=6Hz), 1.94 (3H, d, J=1Hz), 1.80–2.65 (2H, m), 2.65–3.87 (5H, m), 2.92 (6H, s), 3.96–5.10 (3H, m), 5.19–6.59 (2H, m)

Example 11-(4)

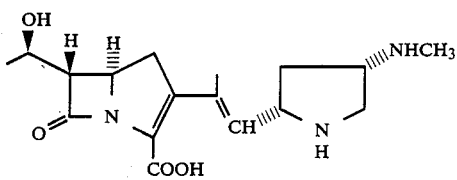

To a solution of allyl (5R,6S)-3-[2-{(2S,4S)-1-allyloxycarbonyl-4-(N-allyloxycarbonyl-N-methylamino)-pyrrolidin-2-yl}-1-methylethenyl]-6-[(1R)-1hydroxyethyl]-7-oxo-1-azabicyclo [3.2.0]hept-2-ene-2-carboxylate (0.495 g) in a mixture of tetrahydrofuran (5 ml) and ethanol (2.5 ml) were added successively triphenylphosphine (96 mg), 5.5-dimethyl-1,3-cyclohxanedione (dimedone)(0.38 g), acetic acid (54.7 μl), and tetrakis(-triphenylphosphine)palladium(0) (85 mg). Stirring at ambient temperature for 1 hour gave a precipitate, which was coolected by filtration, washed with ethyl acetate and dissolved in water (70 ml). The solution was washed with ethyl acetate (30 ml×3) and concentrated in vacuo. The residue was chromatographed on non-ionic adsorption resin "Diaion HP-20" (Trademark, made by Mitsubishi Chemical Industries)(70 ml) eluting with aqueous isopropyl alcohol (3%-20%). The fractions containing the desired compound were collected and lyophilized to give (5R,6S)-6-[(1R)-1-hydroxyethyl]-3-[2-{(2S,4S)-4-(methylamino)-pyrrolidin-2-yl}-1-methylethenyl]-7-oxo-1-azabicyclo-[3.2.0]hept-2-ene-2-carboxylic acid (135 mg).

IR (Nujol): 3350, 1760, 1580 cm$^{-1}$

NMR (D$_2$O, δ): 2.25 (3H, d, J=6Hz), 1.60–2.53 (2H, m), 1.90 (3H, d, J=1Hz), 2.55–4.85 (9H, m), 2.75 (3H, s), 5.44 (1H, dq, J=1,8Hz)

Example 11-(5)

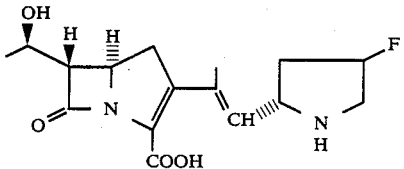

To a solution of allyl (5R,6S)-3-[2-{(2S)-1-allyloxycarbonyl-4-fluoropyrrolidin-2-yl}-1-methylethenyl]-6-[(1R)-1-hydroxyethyl]-7-oxo-1-azabicyclo[3.2.0]hept-2-ene-2-carboxylate (1.7 g), morpholine (694 μl), and triphenylphosphine (199 mg) in tetrahydrofuran (30 ml) and ethanol (10 ml) was added tetrakis(triphenylphosphine)palladium(0) (263 mg) at room temperature. After stirring for an hour, the precipitate was filtered, washed in turn with dichloromethane (3 times) and acetone (twice), and dried under reduced pressure to give (5R,6S)-3-[2-{(2S)-4-fluoropyrrolidin-2-yl}-1-methylethenyl]-6-[(1R)-1hydroxyethyl]-7-oxo-1-azabicyclo 3.2.0]hept-2-ene-2carboxylic acid (248 mg).

IR (Nujol): 3400, 1760, 1590 cm$^{-1}$

NMR (D$_2$O, δ): 1.23 ( 3H, d, J=7Hz), 1.85 (3H, s), 1.60–2.55 (2H, m), 2.55–5.30 (8H, m), 2.95 (2H, t, J=8Hz), 3.37 (1H, dd, J=6Hz, 3Hz), 5.30–5.90 (2H, m)

19 F NMR (D$_2$O, CF$_3$CO$_2$H) −91.5 ppm (m)

Example 11-(6)

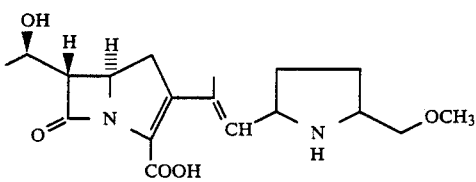

(5R,6S)-6-[(1R)-1-Hydroxyethyl]-3-[2-(5-methoxymethylpyrrolidin-2-yl)-1-methylethenyl]-7-oxo-1-azabicyclo [3.2.0]hept-2-ene-2-carboxylic acid was obtained in 18.6% yield in substantially the same manner as that of Example 4-(1).

IR (Nujol): 3320, 1760, 1630, 1580 cm$^{-1}$
NMR (D$_2$O, δ): 1.27 ( 3H, d, J=7Hz), 1.40–2.50 (4H, m), 1.90 (3H, s), 2.75–3.20 (2H, m), 3.20–5.00 (10H, m), 3.40 (3H, s), 5.43 (1H, d, J=9Hz)
FAB MASS: (M+H)$^+$ m/z=351

Example 11-(7)

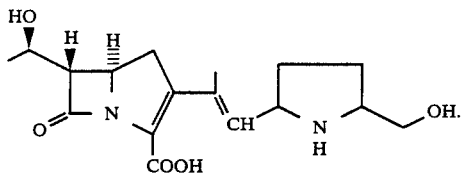

(5R,6S)-3-[2-(5-Hydroxymethylpyrrolidin-2-yl)-1methylethenyl]-6-[(1R)-1-hydroxyethyl]-7-oxo-1-azabicyclo-[ 3.2.0]hept-2-ene-2-carboxylic acid was obtained in 66.4% yield in substantially the same manner as that of Example 4-(1).

IR (Nujol): 3300, 1760, 1580 cm$^{-1}$
NMR (D$_2$O, δ): 1.26 (3H, d, J=7Hz), 1.90 (3H, s), 1.60–2.45 (4H, m), 2.50–3.30 (2H, m), 3.40 (1H, dd, J=3 and 6Hz), 3.55–4.80 (6H, m), 5.45 (1H, d, J=9Hz)
FAB MS: m/z 337 (M+H)$^+$

Example 11-(8)

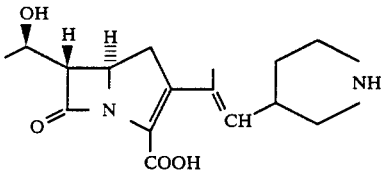

(5R,6S)-6-[(1R)-1-Hydroxyethyl]-7-oxo-3-[2-(pyrrolidin-3-yl)-1-methylethenyl]-1-azabicyclo [3.2.0]hept-2-ene-2-carboxylic acid was obtained in 97.3% yield in substantially the same manner as that of Example 4-(1).
mp: 190° C. (dec.)
IR (KBr): 1755–1735, 1590–1560 cm$^{-1}$
NMR (D$_2$O, δ): 1.28 (3H, d, J=6Hz), 1.85 (3H, s), 5.36 (1H, d, J=8Hz)
FABMS: 307 (M$^+$)

Example 11-(9)

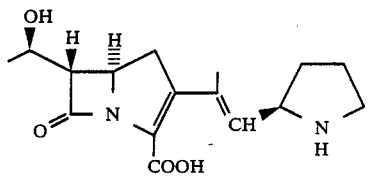

(5R,6S)-6-[(1R)-1-Hydroxyethyl]-7-oxo-3-[2-{(2R)-pyrrolidin-2-yl}-1-methylethenyl]-1-azabicyclo [3.2.0]hept-2-carboxylic acid was obtained in 73.0% yield in substantially the same manner as that of Example 4-1).

IR (CHCl$_3$): 3600, 1760, 1580 cm$^{-1}$
NMR (CDCl$_3$, δ): 1.23 (3H, d, J=7Hz), 1.88 (3H, s), 2.8–3.1 (2H, m), 3.2–3.5 (3H, m), 4.0–4.5 (3H, m), 5.42 (1H, br. d, J=9Hz)

Example 11-(10)

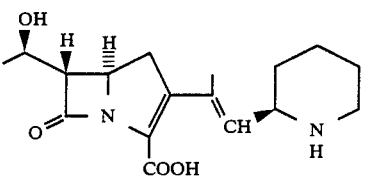

(5R,6S)-6-[(1R)-1-Hydroxyethyl]-7-oxo-3-[2-(piperidin-2-yl)-1-methylethenyl]-1-azabicyclo [3.2.0]hept-2-ene-2carboxylic acid was obtained in 47.2% yield in substantially the same manner as that of Example 4-(1).

IR (Nujol): 3350, 1750, 1580 cm$^{-1}$
NMR (D$_2$O, δ): 1.27 (3H, d, J=6Hz), 1.89 (3H, br s), 1.5–2.0 (4H, m), 2.8–3.5 (5H, m), 3.9–4.4 (3H, m), 5.32 (1H, br, d, J=9Hz)

Example 11-(11)

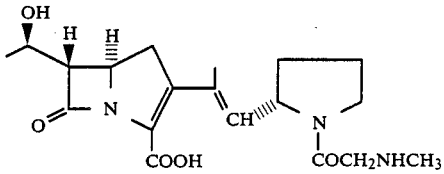

(5R,6S)-3-[2-{(2S)-1-(N-Methylaminoacetyl)pyrrolidin-2-yl}-1-methylethenyl]-6-[(1R)-1-hydroxyethyl]-7-oxo-1azabicyclo[3.2.0]hept-2-ene-2-carboxylic acid was obtained in 49.1% yield in substantially the same manner as that of Example 4-(1).

IR (CHCl$_3$): 3450, 1770, 1650 cm$^{-1}$
NMR (CDCl$_3$, δ): 1.30 (3H, d, J=6Hz), 1.90 (3H, s), 2.80 (3H, s), 1.7–2.3 (4H, m), 2.7–3.2 (3H, m), 3.3–4.8 (5H, m), 5.3–5.7 (1H, m)

Example 11-(12)

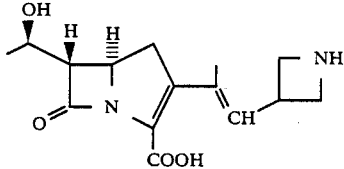

(5R,6S)-3-[2-(Azetidin-3-yl)-1-methylethenyl]-6-[(1R)-1-hydroxyethyl]-7-oxo-1-azabicyclo[3.2.0]hept-2-ene-2-carboxylic acid was obtained in 64.6% yield in substantially the same manner as that of Example 4-(1).

IR (Nujol): 1750, 1615 cm⁻¹

NMR (D₂O, δ): 1.05–1.37 (6H, m), 1.45–1.88 (3H, m), 2.22–2.70 (1H, m), 2.78–3.15 (1H, m), 3.48–4.50 (5H, m), 5.45–5.85 (1H, m)

Example 11-(13)

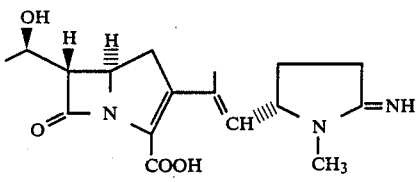

(5R,6S)-6-[(1R)-1-Hydroxyethyl]-3-[2-{(2S)-5-imino-1-methylpyrrolidin-2-yl}-1-methylethenyl]-7-oxo-1-azabicyclo 3.2.0]hept-2-ene-2-carboxylic acid was obtained in 60.4% yield in substantially the same manner as that of Example 4-(1).

IR (Nujol): 1750 cm⁻¹

NMR (D₂O, δ): 1.28 (3H, d, J=6Hz), 1.92 (3H, s), 2.7–3.7 (3H, m), 2.91 (3H, s).

MS: 334 (M⁺+1)

Example 11-(14)

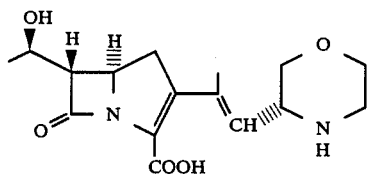

(5R,6S)-6-[(1R)-1-Hydroxyethyl]-3-[2-{(3R)-morpholin-3-yl}-1-methylethenyl]-7-oxo-1-azabicyclo [3.2.0]-hept-2-ene-2-carboxylic acid was obtained in 50.0% yield in substantially the same manner as that of Example 4-(1).

NMR (D₂O, δ): 1.27 (3H, d, J=6Hz), 1.93 (3H, d, J=1Hz), 2.3–4.4 (12H, m), 5.25 (1H, dd, J=7Hz, 1Hz)

Example 11-(15)

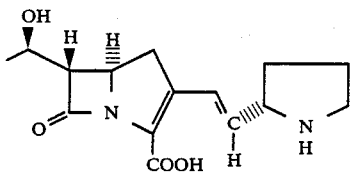

(5R,6S)-6-[(1R)-1-Hydroxyethyl]-7-oxo-3-[(E)-2-{(2S)-pyrrolidin-2-yl}ethenyl]-1-azabicyclo [3.2.0]hept-2-ene-2-carboxylic acid was obtained in 69.0% yield in substantially the same manner as that of Example 4-(1).

IR (Nujol): 3350–3100, 1760–1740 cm⁻¹

NMR (D₂O, δ): 1.23 (3H, d, J=7Hz), 1.60–2.40 (5H, m), 2.83–4.40 (8H, m), 5.56–6.20 (2H, m), 7.28 (1H, d, J=17Hz)

Example 12

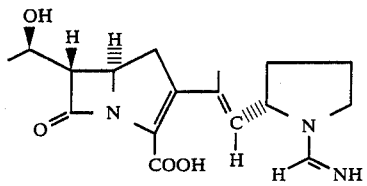

A solution of (5R,6S)-6-[(1R)-1-hydroxyethyl]-7-oxo-3-[(E)-2-{(2S)-pyrrolidin-2-yl}-1-methylethenyl]-1-azabicyclo [3.2.0]hept-2-ene-2-carboxylic acid (0.48 g) in water (30 ml) was adjusted to pH 8.5 with aqueous potassium carbonate at 0° C. and benzyl formimidate hydrochloride (2.7 g) was added in portions while adjusting around pH 8.5 with addition of aqueous potassium carbonate. After stirring for 15 minutes at pH 8.5, the reaction mixture was washed with ethyl acetate and concentrated in vacuo. The residue was chromatographed on nonionic adsorption resin "Diaion HP-20" (50 ml) eluting successively with water and 3% aqueous acetone. The fractions containing the desired compound were collected and lyophilized to give (5S,6S)-3-[(E)-2-{(2S)-1-formimidoylpyrrolidin-2-yl}-1-methylethenyl]-6-[(1R)-1-hydroxyethyl]-7-oxo-1-azabicyclo [3.2.0]hept-2-ene-2-carboxylic acid (170 mg).

IR (Nujol): 1750 cm⁻¹

NMR (D₂O, δ): 1.19 (3H, d, J=6Hz), 1.5-2.5 (7H,m), 5.2–5.5 (1H, m), 7.63 (1H, brs)

Example 13-(1)

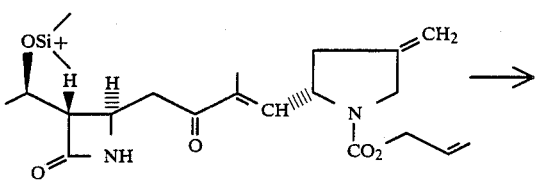

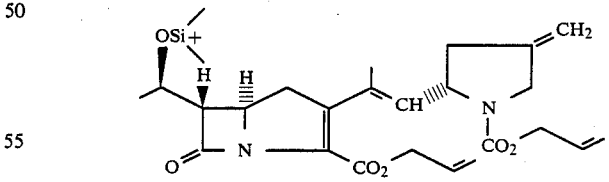

(5R,6S)-3-[2-{(2S)-1-allyloxycarbonyl-4-methylenepyrrolidin-2-yl}-1-methylethenyl]-6[(1R)-1-t-butyldimethylsilyloxyethyl]-7-oxo-1-azabicyclo [3.2.0]-hept-2-ene-2-carboxylate was obtained in 51.7% yield in substantially the same manner as that of Example 8-(1).

NMR (CDCl₃, δ): 0.07 (6H, s), 0.87 (9H, s), 1.24 (3H, d, J=6Hz), 1.92 (3H, br.s), 2.25–2.34 (1H, m), 2.72–3.11 (4H, m), 3.93–4.22 (4H, m), 4.55–4.85 (5H, m), 4.98–5.13 (2H, m), 5.15–5.44 (5H, m), 5.84–6.10 (2H, m)

Example 13-(2)

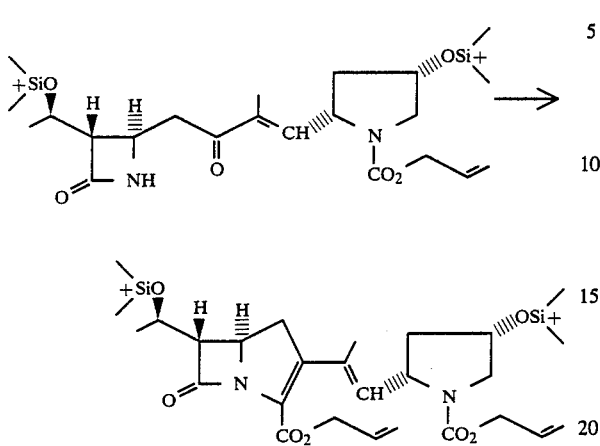

Allyl (5R,6S)-3-[2-{(2S,4S)-1-allyloxycarbonyl-4-(t-butyldimethylsilyloxy) pyrrolidin-2-yl}-1-methylethenyl]-6-[(1R)-1-t-butyldimethylsilyloxyethyl]-7-oxo-1-azabicyclo[3.2.0]hept-2-ene-2-carboxylate was obtained in 44.8% yield in substantially the same manner as that of Example 8-(1).

IR (CH₂Cl₂): 1780, 1695 cm⁻¹

NMR (CDCl₃, δ): 0.06 (12H, s), 0.86 (9H, s), 0.88 (9H, s), 1.25 (3H, d, J=6Hz), 1.56–2.32 (5H, m), 2.88–3.11 (3H, m), 3.28–3.71 (2H, m), 3.90–4.26 (2H, m), 4.48–4.79 (6H, m), 5.10–5.41 (4H, m), 5.72 (1H, d, J=9Hz), 5.79–6.02 (2H, m)

Example 14

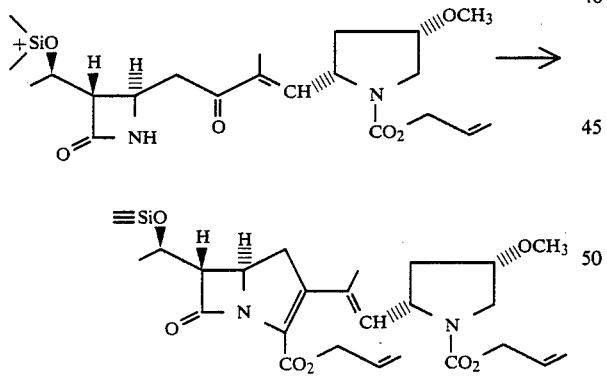

Allyl (5R,6S)-3-[2-{(2S,4S)-1-allyloxycarbonyl-4-methoxypyrrolidin-2-yl}-1-methylethenyl]-6-[(1R)-1-t-butyldimethylsilyloxyethyl]-7-oxo-1-azabicyclo[3.2.0]hept-2-ene-2-carboxylate was obtained in 57.7% yield in substantially the same manner as those of Preparations 46-(4) and 49, and Example 7-(1).

IR (CH₂Cl₂): 1775, 1695 cm⁻¹

NMR (CDCl₃, δ): 0.13 (9H, s), 1.36 (3H, d, J=6Hz), 1.65–2.04 (5H, m), 2.84–3.18 (3H, m), 3.30 (3H, s), 3.49–3.68 (2H, m), 4.46–4.86 (6H, m), 5.12–5.49 (4H, m), 5.61 (1H, d, J=9Hz), 5.78–6.08 (2H, m)

Example 15

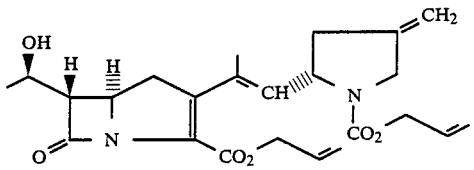

Allyl (5R,6S)-3-[2-{(2S)-1-allyloxycarbonyl-4-methylenepyrrolidin-2-yl}-1-methylethneyl]-6-[(1R)-1hydroxyethyl]-7-oxo-1-azabicyclo [3.2.0]hept-2-ene-2-carboxylate was obtained in 61.1% yield in substantially the same manner as that of Example 10-(1).

NMR (CDCl₃, δ): 1.32 (3H, d, J=6Hz), 1.91 (3H, d, J=1Hz), 2.13–2.50 (1H, m), 2.66–3.30 (4H, m), 3.90–4.35 (4H, m), 4.40–4.93 (5H, m), 4.93–5.52 (7H, m), 5.69–6.20 (2H, m)

Example 16

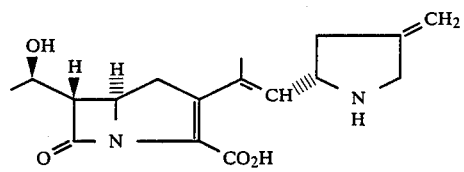

(5R,6S)-6-[(1R)-1-Hydroxyethyl]-3-[2-{(2S)-4-methylenepyrrolidin-2-yl}-1-methylethenyl]-7-oxo-1-azabicyclo [3.2.0]hept-2-ene-2-carboxylic acid was obtained in 20.0% yield in substantially the same manner as that of Example 3-(1).

IR (Nujol): 3300, 1760 cm⁻¹

NMR (D₂O, δ): 1.28 (3H, d, J=6Hz), 1.92 (3H, d, J=1Hz), 2.16–3.23 (4H, m), 3.42 (1H, dd, J=6,3Hz), 3.84–4.80 (5H, m), 5.00–5.32 (2H, m), 5.46 (1H, dq, J=1,9Hz)

Example 17-(1)

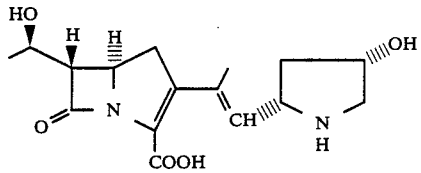

To a solution of allyl (5R,6S)-3-[2-{(2S,4S)-1-allyloxycarbonyl-4-(t-butyldimethylsilyloxy) pyrrolidin-2-yl}-1-methylethenyl]-6-[(1R)-1-t-butyldimethylsilyloxyethyl]-7-oxo-1-azabicyclo 3.2.0]hept-2-ene-2-carboxylate (2.85 g) in tetrahydrofuran (20 ml) were added acetic acid (2.9 ml) and 1.0M solution of tetrabutylammonium fluoride in tetrahydrofuran (25.3 ml) in turn at ambient temperature. After stirring at ambient temperature for 9 hours, the solution was poured into a mixture of water (230 ml) and ethyl acetate (230 ml). The organic layer was separated, washed 5 times with water (100 ml), washed two times with brine (50 ml) dried over magnesium sulfate, and evaporated. To this residue were added tetrahydrofuran (10 ml), ethanol (3.5 ml) and triphenylphosphine (0.08 g). To this solution were added morpholine (0.28 ml) and tetrakis(triphenylphosphine)palladium(0) (0.11 g) successively at ambient temperature. Stirring at ambient temperature for 1 hour gave a precipitate, which was collected by filtration, washed with dichloromethane and dissolved in water (80 ml). The solution was washed with ethyl acetate (40 ml×3) and lyophilized to give (5R,6S)-6-[(1R)-1-hydroxyethyl]-3-[2-{(2S,4S)-4-hydroxypyrrolidin-2-yl}-1-methylethenyl]-7-oxo-1-azabicyclo[3.2.0]hept-2-ene-2-carboxylic acid (155 mg).

IR (Nujol): 1760, 1580 cm$^{-1}$

NMR (D$_2$O, δ): 1.28 (3H, d, J=6Hz), 1.88 (3H, s), 5.51 (1H, d, J=9Hz)

Example 17-(2)

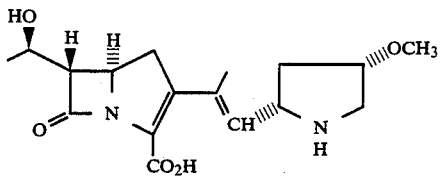

To a solution of allyl (5R,6S)-3-[2-{(2S,4S)-1-allyloxycarbonyl-4-methoxypyrrolidin-2-yl}-1-methylethenyl]-6-[(1R)-1-t-butyldimethylsilyoxyethyl]-7-oxo-1azabicyclo[3.2.0]hept-2-ene-2-carboxylate (1.81 g) in ethyl acetate (3.6 ml) were added acetic acid (0.58 ml) and 1.0M solution of tetrabutylammonium fluoride in tetrahydrofuran (2.4 ml) in turn below 10° C. After stirring for 30 minutes below 10° C., the solution was poured into a mixture of water (10 ml) and ethyl acetate (20 ml). The organic layer was separated, washed 5 times with water (10 ml), washed two times with brine (10 ml), dried over magnesium sulfate, and evaporated. To this residue were added tetrahydrofuran (22 ml), ethanol (7 ml) and triphenylphosphine (0.18 g).

To this solution were added morpholine (0.62 ml) and tetrakis(triphenylphosphine)palladium(0) (0.24 g) successively at ambient temperature. Stirring at ambient temperature for 1.5 hours gave a precipitate, which was collected by filtration, washed with dichloromethane and dissolved in water (200 ml). The solution was washed with ethyl acetate (80 ml×3) and concentrated in vacuo. The residue was chromatographed on nonionic adsorption resin "Diaion HP-20" (100 ml) eluting with aqueous acetonitrile (1%-20%). The fractions containing the desired compound were collected and lyophilized to give (5R,6S)-6-[(1R)-1-hydroxyethyl]-3-[2-{(2S,4S)-4-methoxypyrrolidin-2-yl}-1-methylethenyl]-7-oxo-1-azabicyclo [3.2.0]hept-2-ene-carboxylic acid (37 mg).

IR (Nujol): 1760, 1600 cm$^{-1}$

NMR (D$_2$O, δ): 1.28 (3H, d, J=6Hz), 1.90 (3H, s), 5.44 (1H, d, J=9Hz)

What we claim is:

1. A compound of the formula:

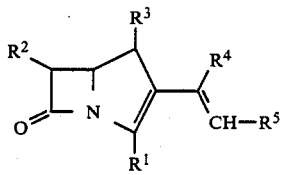

in which
R$^1$ is carboxy or protected carboxy,
R$^2$ is hydoxy(lower)alkyl or protected hydroxy(lower)alkyl,
R$^3$ and R$^4$ are each hydrogen or lower alkyl, and
R$^5$ is saturated 4 to 6-membered heteromonocyclic group containing 1 to 4 nitrogen atom(s), saturated 5 or 6-membered heteromonocyclic group containing 1 to 2 oxygen atom(s) and 1 to 3 nitrogen atom(s) or saturated 5 or 6-membered heteromonocyclic group containing 1 to 2 sulfur atom(s) and 1 to 3 nitrogen atom(s), wherein said aliphatic heterocyclic group may be substituted by one or more suitable substituent(s) selected from a group consisting of hydroxy, protected hydroxy, hydroxy(lower)alkyl, protected hydroxy(lower)alkyl, halogen, lower alkoxy, lower alkyl, lower alkoxy(lower)alkyl, imino, protected imino, lower alkylamino, protected lower alkylamino, mono(or di)(lower)alkylcarbamoyloxy, lower alkylidene, lower alkanimidoyl and imino-protective group, or pharmaceutically acceptable salts thereof.

2. A compound of claim 1, wherein R$^5$ is azetidinyl, N-protected azetidinyl, pyrrolidinyl, N-protected pyrrolidinyl, piperidinyl, N-protectede piperidinyl, morpholinyl or protected morpholinyl, each of which may be substituted by one or two suitable substituent(s) selected from a group consisting of hydroxy, protected hydroxy, hydroxy(lower)alkyl, protected hydroxy(lower)alkyl, halogen, lower alkoxy, lower alkyl, lower alkoxy(lower)alkyl, imino, protected imino, lower alkylamino, protected lower alkylamino, mono(or di)(lower)alkylcarbamoyloxy, lower alkylidene, lower alkanimidoyl and imino-protective group.

3. A compound of claim 2, wherein R$^1$ is carboxy or esterified carboxy, R$^2$ is hydroxy(lower)alkyl, acyloxy(lower)alkyl, C$_6$–C$_{10}$ ar(lower)alkyloxy(lower)alkyl, tri(lower)alkylsilyloxy(lower)alkyl, tri(C$_6$–C$_{10}$)arylsilyloxy(lower)alkyl or tris[(C$_6$–C$_{10}$)-ar(lower)alkyl]silyloxy(lower)alkyl, and R$^5$ is azetidinyl, 1-(lower alkenyloxycarbonyl)azetidinyl, pyrrolidinyl, 1-(lower alkenyloxycarbonyl)-pyrrolidinyl, piperidinyl, 1-(lower alkenyloxycarbonyl)piperidinyl, morpholinyl or 4-(lower alkenyloxycarbonyl)morpholinyl, each of which may be substituted by one or two suitable substituent(s) selected from a group consisting of hydroxy, tri(lower)alkylsilyloxy, hydroxy(lower)-alkyl, tri(lower)alkylsilyloxy(lower)alkyl, halogen, lower alkoxy, lower alkyl, lower alkoxy(lower)alkyl, imino, lower alkenyloxycarbonylimino, lower alkylamino, N-(lower alkenyloxycarbonyl)-N-(lower)-alkylamino, mono(or di)(lower)alkylcarbamoyloxy, lower alkylidene, lower alkanimidoyl and acyl.

4. A compound of claim 3, wherein R$^1$ is carboxy, lower alkenyloxycarbonyl or phenyl(or nitrophenyl)-(lower)alkoxycarbonyl, R$^2$ is hydroxy(lower)alkyl, lower alkenyloxycarbonyloxy(lower)alkyl, phenyl(or nitrophenyl)(lower)alkoxycarbonyloxy(lower)alkyl or tri(lower)alkylsilyloxy(lower)alkyl, and R$^5$ is pyrrolidinyl, 1-(lower)alkenyloxycarbonylpyrrolidinyl, 1-(lower)alkanimidoylpyrrolidinyl, hydroxyprrolidinyl, 1-(lower alkenyloxycarbonyl)(hydroxy)pyrrolidinyl, 1-(lower alkenyloxycarbonyl)[tri(lower)alkylsilyloxy]-pyrrolidinyl, lower alkoxypyrrolidinyl, 1-(lower alkenyloxycarbonyl)(lower alkoxy)pyrrolidinyl, [di(lower)alkylcarbamoyloxy]pyrrolidinyl, 1-(lower alkenyloxycarbonyl)[di(lower)alkylcarbamoyloxy]pyrrolidinyl, (lower alkylcarbamoyloxy)pyrrolidinyl, 1-(lower alkenyloxycarbonyl)(lower alkylcarbamoyloxy)pyrrolidinyl, (lower alkylamino)pyrrolidinyl, 1-(lower alkenyloxycarbonyl)[N-(lower)alkenyloxycarbonyl-N-(lower)alkylamino]pyrrolidinyl, halopyrrolidinyl, 1-(lower alkenyloxycarbonyl)halopyrrolidinyl, [lower alkoxy(lower)alkyl]pyrrolidinyl, 1-(lower alkenyloxycarbonyl)[lower alkoxy(lower)alkyl]pyrrolidinyl, [hydroxy(lower)alkyl]pyrrolidinyl, 1-(lower alkenyloxycarbonyl)[hydroxy(lower)alkyl]pyrrolidinyl, 1-[lower alkylamino(lower)alkanoyl]pyrrolidinyl, 1-[N-(lower)alkenyloxy-carbonyl-N-(lower) alkylamino(lower)alkanoyl]pyrrolidinyl, (lower alkyl)(imino)pyrrolidinyl,, 1-(lower alkyl)(lower alkenyloxycarbonylimino)pyrrolidinyl, piperidinyl, 1-(lower alkenyloxycarbonyl)piperidinyl, azetidinyl, 1-(lower alkenyloxycarbonyl)azetidinyl, morpholinyl, 4-(lower)alkenyloxycarbonylmorpholinyl, lower alkylidenepyrrolidinyl or 1-(lower)alkenyloxycarbonyl(lower alkylidene)pyrrolidinyl.

5. A compound of claim 4, wherein $R^1$ is carboxy, $R^2$ is hydroxy($C_1$–$C_4$)alkyl, $R^3$ is hydrogen, $R^4$ is hydrogen or $C_1$–$C_4$ alkyl, and $R^5$ is pyrrolidinyl, hydroxypyrrolidinyl, $C_1$–$C_4$ alkoxypyrrolidinyl, [di($C_1$–$C_4$)alkylcarbamoyloxy]pyrrolidinyl, ($C_1$–$C_4$ alkylcarbamoyloxy)pyrrolidinyl, $C_1$–$C_4$ alkylaminopyrrolidinyl, halopyrrolidinyl, [$C_1$–$C_4$ alkoxy($C_1$–$C_4$)alkyl]pyrrolidinyl, [hydroxy($C_1$–$C_4$)alkyl]pyrrolidinyl, 1-[$C_1$–$C_4$ alkylamino($C_1$–$C_4$)alkanoyl]pyrrolidinyl or 1-[($C_1$–$C_4$)alkyl]iminopyrrolidinyl or $C_1$–$C_4$ alkylidenepyrrolidinyl.

6. A compound of claim 5, which is selected from a group consisting of
(5R,6S)-6-[(1R)-1-hydroxyethyl]-7-oxo-3[(E)-2-{(2S)-pyrrolidin-2-yl}-1-methylethenyl]-1azabicyclo[3.2.0]hept-2-ene-2-carboxylic acid,
(5R,6S)-6-[(1R)-1-hydroxyethyl]-3-[2-{(2S,4R)-4-hydroxypyrrolidin-2-yl}-1-methylethenyl]-7oxo-1-azabicyclo[3.2.0]hept-2-ene-2-carboxylic acid,
(5R,6S)-3-[(E)-2-{(2S)-1-acetimidoylpyrrolidin-2-yl}-1-methylethenyl]-6-[(1R)-1-hydroxyethyl]-7-oxo-1azabicyclo[3.2.0]hept-2-ene-2-carboxylic acid,
(5R,6S)-6-[(1R)-1-hydroxyethyl]-3-[2-{(2S,4R)-4-methoxypyrrolidin-2-yl}-1-methylethenyl]-7-oxo-1-azabicyclo[3.2.0]hept-2-ene-2-caroxylic acid,
(5R,6S)-6-[(1R)-1-hydroxyethyl]-3-[2-{(2S,4R)-4-(methylcarbamoyloxy) pyrrolidin-2-yl}-1-methylethenyl]-7-oxo-1-azabicyclo[3.2.0]hept-2-ene-2carboxylic acid,
(5R,6S)-3-[2-{(2S,4R)-4-(dimethylcarbamoyloxy)-pyrrolidin-2-yl}-1-methylethenyl]- 6[(1R)-1hydroxyethyl]7-oxo-1-azabicyclo[3.2.0]hept-2-ene-2carboxylic acid,
(5R,6S)-6-[(1R)-1-hydroxyethyl]-3-[2-{(2S,4S)-4-(methylamino) pyrrolidin-2-yl}-1-methylethenyl]-7-oxo-1-azabicyclo[3.2.0]hept-2-ene-2-carboxylic acid,
(5R,6S)-3-[2-{(2S)-4-fluoropyrrolidin-2-yl}-1methylethenyl]-6-[(1R)-1-hydroxyethyl]-7-oxo-1azabicyclo[3.2.0]hept-2-ene-2-carboxylic acid,
(5R,6S)-6-[(1R)-1-hydroxyethyl]-3-[2-(5-methoxymethylpyrrolidin-2-yl-1-methylethenyl]- 7-oxo-1-azabicyclo[3.2.0]hept-2-ene-2-carboxylic acid,
(5R,6S)-3-[2-(5-hydroxymethylpyrrolidin-2-yl)-1methylethyl]-6-[(1R)-1-hydroxyethyl]-7-oxo-1azabicyclo[3.2.0]hept-2-ene-2-carboxylic acid,
(5R,6S)-6-[(1R)-1-hydroxyethyl]-7-oxo-3-[2-(pyrrolidin-3-yl)-1-methylethenyl]-1-azabicyclo[3.2.0]hept-2-ene-2-carboxylic acid,
(5R,6S)-6-[(1R)-1-hydroxyethyl]-7-oxo-3-[2-yl]-1-methylethenyl]-1-azabicyclo[3.2.0]hept-2-ene-2-carboxylic acid,
(5R,6S)-6-[(1R)-1-hydroxyethyl]-3-[2-{(2S)-1-(N-methyaminoacetyl) pyrrolidin-2-yl}-1-methylethenyl]-7-oxo-1-azabicyclo[ 3.2.0]hept-2-ene-2-carboxylic acid,
(5R,6S)-6-[(1R-1-hydroxyethyl]-3-[2-{(2S)-5-imino-1-methylpyrrolidin-2-yl}-1-methylethenyl]-7-oxo-1-azabicyclo[3.2.0]hept-2-ene-2-carboxylic acid,
(5R,6S)-6-[(1R)-1-hydroxyethyl]-7-oxo-3-[(E)-2-{(2S)-pyrrolidin-2-yl}-1-ethenyl]-1-azabicyclo[3.2.0]hept-2-ene-2-carboxylic acid,
(5R,6S)-3-[(E)-2-{(2S)-1-formimidoylpyrrolidin-2-yl}-1-methylethenyl]- 6-[(1R)-1-hydroxyethyl]-7-oxo-1azabicyclo[3.2.0]hept-2-ene-2-carboxylic acid,
(5R,6S)-6-[(1R)-1-hydroxyethyl]-3-[2-{(2S,4S)-4-hydroxypyrrolidin-2yl}-1-methylethenyl]-7-oxo-1-azabicyclo[[3.2.0]hept-2-ene-2-carboxylic acid,
(5R,6S)-6-[(1R)-1-hydroxyethyl]-3-[2-{(2S)-4-methylenepyrrolidin-2-yl}1-methylethenyl]-7-oxo-1-azabicyclo[3.2.0]hept-2-ene-2-carboxylic acid and
(5R,6S)-6-[(1R)-1-hydroxyethyl]-3-[2-{(2S,4S)-4-methoxypyrrolidin-2-yl}-1-methylethenyl]-7-oxo-1-azabicyclo[3.2.0]hept-2-ene-carboxylic acid.

7. An antimicrobial composition comprising, an effective amount of a compound of claim 1, in admixture with a pharmaceutically acceptable carrier or excipient.

8. A method for the treatment of infectious diseases caused by pathogenic bacteria which comprises administering an effective amount of a compound of claim 1 to a human being or animal.

* * * * *

UNITED STATES PATENT AND TRADEMARK OFFICE
CERTIFICATE OF CORRECTION

PATENT NO. : 4,923,857
DATED : MAY 8, 1990
INVENTOR(S) : Masayoshi MURATA, et al.

It is certified that error appears in the above-identified patent and that said Letters Patent is hereby corrected as shown below:

| COLUMN | LINE | | |
|---|---|---|---|
| 76 | 21 | Change "N-protectede" to | --N-protected--. |
| 76 | 22 | Change "protected" to | --N-protected--. |
| 78 | 16 | Change "[2-yl}" to | -- [2-{(2R)-pyrrolidin-2-yl} --. |
| 78 | 20 | Change "methyamino---" to | -- methylamino--- --. |
| 78 | 23 | Change "(1R-" to | -- (1R)- --. |
| 78 | 34 | Change "[[3.2.0]" to | -- [3.2.0] |

Signed and Sealed this

Twenty-first Day of July, 1992

*Attest:*

DOUGLAS B. COMER

*Attesting Officer*   Acting Commissioner of Patents and Trademarks